(12) United States Patent
Kaila et al.

(10) Patent No.: US 7,994,333 B2
(45) Date of Patent: Aug. 9, 2011

(54) METHODS AND COMPOSITIONS FOR SELECTIN INHIBITION

(75) Inventors: Neelu Kaila, Lexington, MA (US); Silvano L. Debarnardo, Verona, NJ (US); Kristin M. Janz, Arlington, MA (US); Raymond T. Camphausen, Wayland, MA (US); Patricia Ward Bedard, Mansfield, MA (US); Adrian Huang, Lexington, MA (US)

(73) Assignee: Wyeth LLC, Madison, NJ (US)

( * ) Notice: Subject to any disclaimer, the term of this patent is extended or adjusted under 35 U.S.C. 154(b) by 488 days.

(21) Appl. No.: 12/267,051

(22) Filed: Nov. 7, 2008

(65) Prior Publication Data

US 2009/0069564 A1 Mar. 12, 2009

Related U.S. Application Data

(62) Division of application No. 10/984,522, filed on Nov. 9, 2004, now Pat. No. 7,465,798.

(60) Provisional application No. 60/518,939, filed on Nov. 10, 2003, provisional application No. 60/542,986, filed on Feb. 9, 2004.

(51) Int. Cl.
C07D 221/00 (2006.01)
C07D 213/04 (2006.01)
C07D 213/62 (2006.01)
C07D 211/68 (2006.01)
A61K 31/4725 (2006.01)

(52) U.S. Cl. ........ 546/285; 546/194; 546/255; 546/261; 546/326; 514/293

(58) Field of Classification Search .................. None
See application file for complete search history.

(56) References Cited

U.S. PATENT DOCUMENTS

| | | | |
|---|---|---|---|
| 5,840,679 A | 11/1998 | Larsen et al. | |
| 6,232,320 B1 | 5/2001 | Stewart et al. | |
| 2008/0125454 A1* | 5/2008 | Bedard et al. | 514/292 |
| 2008/0255192 A1* | 10/2008 | Kaila et al. | 514/312 |

FOREIGN PATENT DOCUMENTS

| | | |
|---|---|---|
| EP | 1 422 782 A | 5/2004 |
| JP | 2005-108720 | 4/2005 |
| WO | WO 99/29705 A | 6/1999 |
| WO | WO 03/001968 A | 1/2003 |
| WO | WO 2005/004251 | 1/2005 |
| WO | 2005/047258 | 5/2005 |

OTHER PUBLICATIONS

Waters M. et al., Tetrahedron Letters, Elsevier, Amsterdam, NL; vol. 41, No. 2; Thiol Addition to Aryl Propargyl Alcohols Under Miled Conditions: An Accelerating Neighboring Group Effect; pp. 141-144; 2000.

Bumagin et al., "A Convenient Synthesis of Substituted Propargyl Alcohols and Terminal Acetylenes," *Synthesis*, (9), pp. 728-729 (1984).
Kaila et al., "2-(4-Chlorobenzyl)-3-Hydoroxy-7,8,9,10-Tetrahydrobenzo[H]-Quinoloine-4-Carboxylic Acid (PSI-697): Identification of a Clinical Candidate from the Quinoline Salicylic Acid Series of P-Selectin Antagonists," *J. Med. Chem.*, (50), pp. 40-64 (2007).
Kondoh et al., "Stereoselective Hydrothiolation of Alkynes Catalyzed by Cesium Base: Facile Access to (Z)-I-Alkenyl Sulfides," *J. Org. Chem.*, 70 (16), pp. 6468-6473 (2005).
Okuro et al., "Synthesis of Aryl- and Vinylacetylene Derivatives by Copper-Catalyzed Reaction of Aryl and Vinyl Iodides with Terminal Alkynes," *J. Org. Chem.*, 58 (17), pp. 4716-4721 (1993).
Shvekhgeimer, "The Pfitzinger Reaction. (Review)," *Chemistry of Heterocyclic Compounds*, 40 (3), pp. 257-294 (2004).
Boschelli et al., "Inhibition of E-selectin-, ICAM-1-, and VCAM-1-mediated cell adhesion by benzo[b]thiophene-, benzofuran-, indole-, and naphthalene-2-carboxamides: Identification of PD 144795 as an anti-inflammatory agent," *Journal of Medicinal Chemistry* (1995) 38(22):4597-4614.
International Search Report dated May 11, 2005 for International Application No. PCT/US2004/037441.
Cragoe et al., *J. Org. Chem.* (1953) 18:561.
Frenette et al., "Insights into selectin function from knockout mice" *Thromb. Haemost* (1997) 78(1)60-64.
Huo "Highly efficient, general procedure for the preparation of alkylzinc reagents from unactivated alkyl bromides and chlorides" *Organic Letters* (2003) 5(4):423-425.
Johnson et al., "Absence of P-selectin delays fatty streak formation in mice" *J. Clin. Invest.* (1997) 99:1037-1043.
Kumar et al., "Recombinant soluble form of PSGL-1 accelerates thrombolysis and prevents reocclusion in a porcine model" *Circulation* (1999) 99(10):1363-1369.
Lisowski et al., "Efficient synthesis of novel 3-(Het)arylanthranilic acids via a suzuki cross-coupling reaction of 7-iodoisatin with (Het)arylboronic acids in water" *J. Org. Chem.* (2000) 65:4193-4194.
Molenaar et al., "P-selectin as a candidate target in atherosclerosis" *Biochem. Pharmacol.* (2003) 66:859-866.
Pouyani et al., "PSGL-1 recognition of P-selectin is controlled by a tyrosine sulfation consensus at the PSGL-1 amino terminus" *Cell* (1995) 83(2):333-343.

(Continued)

*Primary Examiner* — Kamal Saeed
*Assistant Examiner* — Nyeemah A Grazier
(74) *Attorney, Agent, or Firm* — Ram W. Sabnis

(57) ABSTRACT

The present invention relates to the field of anti-inflammatory substances, and more particularly to novel compounds that act as antagonists of the mammalian adhesion proteins known as selectins. In some embodiments, methods for treating selectin mediated disorders are provided which include administration of compound of Formula I:

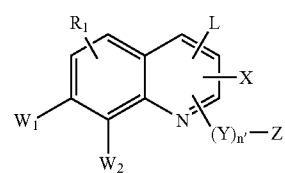

wherein the constituent variables are defined herein.

6 Claims, No Drawings

OTHER PUBLICATIONS

Rewcastle et al., "Potential antitumor agents. 61. Structure-activity relationships for in vivo colon 38 activity among disubstituted 9-oxo-9H-xanthene-4-acetic acids." *J. Med. Chem.* (1991) 34:217-222.

Sako et al., "A sulfated peptide segment at the amino terminus of PSGL-1 is critical for P-selectin binding" *Cell* (1995) 83(2):323-331.

Scalia et al., "Effect of recombinant soluble P-selectin glycoprotein ligand-1 on leukocyte-endothelium interaction in vivo. Role in rat traumatic shock" *Circ. Res.* (1999) 84(1):93-102.

Somers et al., "Insights into the molecular basis of leukocyte tethering and rolling revealed by structures of P- and E-selectin bound to SLe(X) and PSGL-1," *Cell* (2000) 103:467-479.

Takada et al., "The cytokine-adhesion molecule cascade in ischemia/reperfusion injury of the rat kidney. Inhibition by a soluble P-selectin ligand," *J. Clin. Invest.* (1997) 99(11):2682-2690.

Wilkins et al., "Tyrosine sulfation of P-selectin glycoprotein ligand-1 is required for high affinity binding to P-selectin," *J. Biol. Chem.* (1995) 270(39):22677-22680.

Yang et al., "Induction of a Ferroelectric Sc* Liquid Crystal Phase by an Atropisomeric Dopant Derived from 4,4'-Dihydroxy-2,2'-dimethyl-6,6'-dinitrobiphenyl" *J. Am. Chem. Soc.* (1996) 118(40):9557-9561.

Berge et al., "Pharmaceutical Salts," *Journal of Pharmaceutical Sciences* (1977) 66(1): 1-19.

Greene et al., *Productive Groups in Organic Synthesis* (1991) 2d ed, John Wiley & Sons, New York.

Marvel and Hiers *Org. Synth. Coll.* vol. II (1944) 2d ed. (Blatt, A.H., ed.), John Wiley & Sons, New York, pp. 165-167.

Marvel and Hiers *Org. Synth. Coll.* vol. I, (1941) 2d ed. (Blatt, A.H., ed.), John Wiley & Sons, New York, p. 327.

*Remington's Pharmaceutical Sciences* (1980) Mack Pub. Co., Easton, PA.

* cited by examiner

US 7,994,333 B2

METHODS AND COMPOSITIONS FOR SELECTIN INHIBITION

CROSS-REFERENCE TO RELATED APPLICATIONS

This application claims priority to U.S. application Ser. No. 10/984,522 filed on Nov. 9, 2004 claiming the benefit under 35 USC 119(e) to U.S. provisional application Ser. No. 60/518,939 filed Nov. 10, 2003 and Ser. No. 60/542,986 filed on Feb. 9, 2004, which are incorporated herein by reference in their entirety.

FIELD OF INVENTION

The present invention relates to the field of anti-inflammatory substances, and more particularly to novel compounds that act as antagonists of the mammalian adhesion proteins known as selecting.

BACKGROUND OF THE INVENTION

During the initial phase of vascular inflammation, leukocytes and platelets in flowing blood decrease velocity by adhering to the vascular endothelium and by exhibiting rolling behavior. This molecular tethering event is mediated by specific binding of a family of calcium dependent or "C-type" lectins, known as selecting, to ligands on the surface of leukocytes. There are also several disease states that can cause the deleterious triggering of selectin-mediated cellular adhesion, such as autoimmunity disorders, thrombotic disorders, parasitic diseases, and metastatic spread of tumor cells.

The extracellular domain of a selectin protein is characterized by an N-terminal lectin-like domain, an epidermal growth factor-like domain, and varying numbers of short consensus repeats. Three human selectin proteins have been identified, including P-selectin (formerly known as PADGEM or GMP-140), E-selectin (formerly known as ELAM-1), and L-selectin (formerly known as LAM-1). E-selectin expression is induced on endothelial cells by proinflammatory cytokines via its transcriptional activation. L-selectin is constitutively expressed on leukocytes and appears to play a key role in lymphocyte homing. P-selectin is stored in the alpha granules of platelets and the Weibel-Palade bodies of endothelial cells and therefore can be rapidly expressed on the surface of these cell types in response to proinflammatory stimuli. Selectins mediate adhesion through specific interactions binds to carbohydrates having the terminal structure:

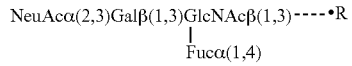

and also to carbohydrates having the terminal structures:

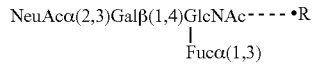

where R is the remainder of the carbohydrate chain. These carbohydrates are known blood group antigens and are commonly referred to as Sialyl Lewis x and Sialyl Lewis a, respectively. The presence of the Sialyl Lewis x antigen alone on the surface of an endothelial cell may be sufficient to promote binding to an E-selectin expressing cell. E-selectin also binds to carbohydrates having the terminal structures:

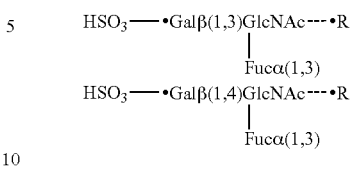

As with E-selectin, each selectin appears to bind to a range of carbohydrates with varying affinities. The strength of the selectin mediated adhesive event (binding affinity) may also depend on the density and context of the selectin on the cell surface.

Structurally diverse glycoprotein ligands, including GlyCAM-1, CD34, ESL-1 and PSGL-1 can bind to selectins with apparent high affinity. PSGL-1 is a mucin-like homodimeric glycoprotein expressed by virtually all subsets of leukocytes and is recognized by each of the three selecting However PSGL-1 appears to be unique in that it is the predominant high affinity P-selectin ligand on leukocytes. High affinity P-selectin binding to PSGL-1 requires both a SLex containing O-glycan and one or more tyrosine sulfate residues within the anionic N-terminus of the PSGL-1 polypeptide (See Sako, D., et al. *Cell* 1995; 82(2): 323-331; Pouyani, N., et al., *Cell* 1995; 82(2): 333-343; Wilkins, P. P., et al., *J. Biol. Chem.* 1995; 270:39 22677-22680, each of which is incorporated herein by reference in its entirety). L-Selectin also recognizes the N-terminal region of PSGL-1 and has similar sulfation-dependent binding requirements to that of P-selectin. The ligand requirements of E-selectin appear to be less stringent as it can bind to the SLex containing glycans of PSGL-1 and other glycoproteins. Despite the fact that P-selectin knockout and P/E selectin double knockout mice show elevated levels neutrophils in the blood, these mice show an impaired DTH response and delayed thioglycolate induced peritonitis (TIP) response (See Frenette, P. S., et al., *Thromb Haemost* 1997; 78:1, 60-64, incorporated herein by reference in its entirety). Soluble forms of PSGL-1 such as rPSGL-Ig have shown efficacy in numerous animal models (See Kumar, A., et. al., *Circulation.* 1999, 99(10) 1363-1369; Takada, M., et. al. *J. Clin. Invest.* 1997, 99(11), 2682-2690; Scalia, R., et al., *Circ Res.* 1999, 84(1), 93-102, each of which is incorporated herein by reference in its entirety.

In addition, P-selectin ligand proteins, and the gene encoding the same, have been identified. See U.S. Pat. No. 5,840,679, incorporated herein by reference in its entirety. As demonstrated by P-selectin/LDLR deficient mice, inhibition of P-selectin represents a useful target for the treatment of atherosclerosis (See Johnson, R. C., et al., *J. Clin. Invest.* 1997 99 1037-1043, incorporated herein by reference in its entirety). An increase in P-selectin expression has been reported at the site of atherosclerotic lesions, and the magnitude of the P-selectin expression appears to correlate with the lesion size. It is likely that the adhesion of monocytes, mediated by P-selectin, contributes to atherosclerotic plaque progression (See Molenaar, T. J. M., et al., *Biochem. Pharmacol.* 2003 (66) 859-866, incorporated herein by reference in its entirety). Given the role of selectins in numerous important biological processes, including inflammation and adhesion processes, and in disorders such as atherlosclerosis, it can be seen that there is a continuing need for new selectin inhibitors that can be useful in the treatment of a variety of diseases and disorders that are characterized by, or that involve selectin activity. This invention is directed to these, as well as other, important ends.

SUMMARY OF THE INVENTION

In one aspect, the present invention provides compounds and methods for treating mammals having conditions characterized by selectin mediated intercellular adhesion processes. In one aspect, the invention provides compounds useful in the methods, that have the Formula I:

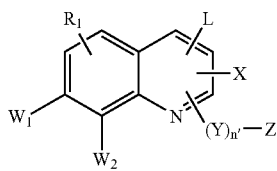

wherein:

$W_1$ and $W_2$ taken together with the atoms to which they are attached form a 5 or 6 member carbocyclic or heterocyclic ring that can be saturated, partially saturated or aromatic, and that can be substituted with up to three groups independently selected from hydrogen, $C_{1-6}$ alkyl, $C_{1-6}$ perhaloalkyl, $OC_{1-6}$ alkyl, $OC_{1-6}$ perhaloalkyl, halogen, thioalkyl, CN, OH, SH, $(CH_2)_nOSO_3H$, $(CH_2)_nSO_3H$, $(CH_2)_nCO_2R_6$, $OSO_3R_6$, $SO_3R_6$, $SO_2R_6$, $PO_3R_6R_7$, $(CH_2)_nSO_2NR_8R_9$, $(CH_2)_nC(=O)NR_8R_9$, $NR_8R_9$, $C(=O)R_{12}$, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl, alkynyl, and $NHCOR_8$, wherein any of said alkyl, Oalkyl, aryl, heterocyclo, $C(=O)$aryl, $C(=O)$heterocyclo, $O-C(=O)$aryl, $O-C(=O)$heterocyclo, O-aryl, O-heterocyclo, arylalkyl, $C(=O)$arylalkyl, $O-C(=O)$arylalkyl, O-arylalkyl, alkenyl or alkynyl can optionally be substituted with up to three substituents selected from halogen, $C_{1-6}$ alkyl, $OC_{1-6}$ alkyl and CN;

L is $CO_2H$, an ester thereof, or a pharmaceutically acceptable acid mimetic;

Y is O, $(CR_3R_4)_p$ or $NR_5$;

n' is 0 or 1;

p is 1 to 3;

X is hydrogen, OH, $OR_3$, $OC_{1-6}$ alkyl, $OC(=O)$-aryl, $OC(=O)C_{1-6}$ alkyl, $OC(=O)OC_{1-6}$ alkyl, or $NR_3R_3$;

each $R_1$, $R_3$, and $R_4$ is independently hydrogen, $C_{1-6}$ alkyl, $C_{1-6}$ perhaloalkyl, $OC_{1-6}$ alkyl, $OC_{1-6}$ perhaloalkyl, halogen, thioalkyl, CN, OH, SH, $(CH_2)_nOSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)NR_8R_9$, $NR_8R_9$, $C(=O)R_{12}$, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl, alkynyl, or $NHCOR_8$, wherein any of said alkyl, Oalkyl, aryl, heterocyclo, $C(=O)$aryl, $C(=O)$heterocyclo, $O-C(=O)$aryl, $O-C(=O)$heterocyclo, O-aryl, O-heterocyclo, arylalkyl, $C(=O)$arylalkyl, $O-C(=O)$arylalkyl, O-arylalkyl, alkenyl or alkynyl can optionally be substituted with up to three selected from halogen, $C_{1-6}$ alkyl, $OC_{1-6}$ alkyl and CN;

each $R_6$ and $R_7$ is independently hydrogen or $C_{1-6}$ alkyl that is optionally substituted with up to three substituents selected from OH, $CF_3$, SH and halogen;

each $R_5$, $R_8$ and $R_9$ is independently hydrogen, $C_{1-6}$ alkyl, $C_{1-6}$ haloalkyl, thioalkyl, OH, $(CH_2)_lOSO_3H$, $(CH_2)_lSO_3R_{10}$, $(CH_2)_nCO_2R_{10}$, $SO_3R_{10}$, $PO_3R_{10}R_{11}$, $(CH_2)_nSO_2(CH_2)_nNR_{10}R_{11}$, $(CH_2)_nCONR_{10}R_{11}$, $COR_{10}$, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl, or alkynyl, wherein any of said alkyl, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl or alkynyl can optionally be substituted with up to three substituents selected from halogen, $C_{1-6}$ alkyl, $OC_{1-6}$ alkyl and CN;

each n is an independently selected integer from 0 to 6;

each l is an independently selected integer from 1 to 6;

each $R_{10}$ and $R_{11}$ is independently selected from hydrogen and $C_{1-6}$ alkyl that is optionally substituted with up to three substituents selected from OH, $CF_3$, SH and halogen;

each $R_{12}$ is independently hydrogen, $C_{1-6}$ alkyl, $C_{1-6}$ perhaloalkyl, OC 06 alkyl, $OC_{1-6}$ perhaloalkyl, thioalkyl, OH, $(CH_2)_lOSO_3H$, $(CH_2)_lSO_3H$, $(CH_2)_lCO_2R_6$, $(CH_2)_lSO_2NR_8R_9$, $(CH_2)_lC(=O)NR_8R_9$, $NR_8R_9$, alkenyl, alkynyl, or $NHCOR_8$, wherein any of said alkyl, Oalkyl, alkenyl or alkynyl can optionally be substituted with up to three substituents selected from halogen, $C_{1-6}$ alkyl, $OC_{1-6}$ alkyl and CN; and Z is aryl, heteroaryl, arylalkyl or heterocyclo, wherein each of said aryl, heteroaryl, arylalkyl and heterocyclo is optionally substituted.

In some preferred embodiments, the compounds have the Formula II:

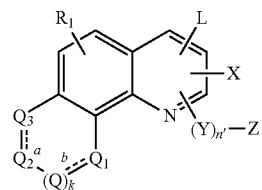

wherein:

bond a and bond b can each independently be a single bond or a double bond;

$Q_1$, $Q_2$, $Q_3$ and Q are each independently $CR_{2'}$, $CHR_{2'}$, N or $NR_{13}$;

k is 0 or 1;

each $R_{2'}$ is independently hydrogen, $C_{1-6}$ alkyl, $C_{1-6}$ perhaloalkyl, $OC_{1-6}$ alkyl, $OC_{1-6}$ perhaloalkyl, halogen, thioalkyl, CN, OH, SH, $(CH_2)_nOSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)NR_8R_9$, $NR_8R_9$, $C(=O)R_{12}$, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl, alkynyl, or $NHCOR_8$, wherein any of said alkyl, Oalkyl, aryl, heterocyclo, $C(=O)$aryl, $C(=O)$heterocyclo, $O-C(=O)$aryl, $O-C(=O)$heterocyclo, O-aryl, O-heterocyclo, arylalkyl, $C(=O)$arylalkyl, $O-C(=O)$arylalkyl, O-arylalkyl, alkenyl or alkynyl can optionally be substituted with up to three substituents selected from halogen, $C_{1-6}$ alkyl, $OC_{1-6}$ alkyl and CN; and each $R_{13}$ is each independently hydrogen, $C(=O)R_{20}$, $SO_2R_{20}$, $C_{1-6}$ alkyl, $C_{1-6}$ haloalkyl, thioalkyl, OH, $(CH_2)_lOSO_3H$, $(CH_2)_lSO_3R_{10}$, $(CH_2)_nCO_2R_{10}SO_3R_{10}$, $PO_3R_{10}R_{11}$, $(CH_2)_nSO_2(CH_2)_nNR_{10}R_{11}$, $(CH_2)_n$ $CONR_{10}R_{11}$, $COR_{10}$, aryl, heterocyclo, C(=O)aryl, C(=O) heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl, or alkynyl, wherein any of said alkyl, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl or alkynyl can optionally be substituted with up to three substituents selected from halogen, $C_{1-6}$ alkyl, $OC_{1-6}$ alkyl and CN;

each $R_{20}$ is independently selected from the group consisting of $C_{1-10}$ alkyl, $OC_{1-10}$ alkyl and $NR_6R_7$;

and $R_1$, L, X, Y, n', and Z have the meaning described above.

In some preferred embodiments, substituents $(Y)_{n'}-Z$, X and L are attached at the 2-, 3- and 4-positions of the quinoline, respectively, as shown below in Formula III:

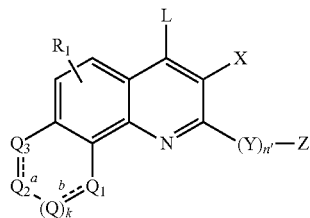

II

I

In some embodiments, k is 1, and bonds a and b are each single bonds. In further embodiments, k is 1, bonds a and b are each single bonds, and Q, $Q_1$, $Q_2$ and $Q_3$ are each independently $CHR_{2'}$, preferably $CH_2$.

In some embodiments, k is 0, bond a is a single bond, and $Q_1$, $Q_2$ and $Q_3$ are each independently $CHR_{2'}$, preferably $CH_2$.

In some embodiments, k is 0, bond a is a single bond, and $Q_1$ is $NR_{13}$, preferably NH, preferably wherein $Q_2$ and $Q_3$ are each $CH_2$.

In some embodiments, k is 1, bond a and bond b are each double bonds, and Q, $Q_1$, $Q_2$ and $Q_3$ are each $CR_{2'}$, preferably $CH_2$.

In some embodiments, $Q_1$, $Q_2$ and $Q_3$ are $CH_2$; k is 1, and Q is $NR_{13}$.

In some embodiments, n' is 0. In other embodiments, n' is 1. In some embodiments wherein n' is 1, Y is $CR_3R_4$, preferably $CH_2$, preferably wherein X is OH. Preferably, L is $CO_2H$ or an ester thereof.

In some embodiments, n' is 0 and X is OH, preferably wherein L is $CO_2H$ or an ester thereof.

In some embodiments, Z is selected from:

(a) a five-membered heterocyclic ring containing one to three ring heteroatoms selected from N, S or O; wherein said five-membered heterocyclic ring is optionally substituted by from 1 to 3 substituents selected from halogen, $C_{1-10}$ alkyl, $OC_{1-10}$ alkyl, $NO_2$, $NH_2$, CN, $CF_3$, and $CO_2H$;

(b) a six-membered heterocyclic ring containing one to three ring heteroatoms selected from N, S or O; wherein said six-membered heterocyclic ring is optionally substituted by from 1 to 3 substituents selected from halogen, $C_{1-10}$ alkyl, $OC_{1-10}$ alkyl, CHO, $CO_2H$, C(=O)$R_{20}$, $SO_2R_{20}$, $NO_2$, $NH_2$, CN, $CF_3$ and OH;

(c) a bicyclic ring moiety optionally containing from 1 to 3 ring heteroatoms selected from N or O; wherein said bicyclic ring moiety is optionally substituted by from 1 to 3 substituents selected from halogen, $C_{1-6}$ alkyl, $OC_{1-6}$ alkyl, CHO, $NO_2$, $NH_2$, CN, $CF_3$, $CO_2H$, C(=O)$R_{20}$, $SO_2R_{20}$, and OH; and (d) a benzyl, naphthyl, or phenyl ring, each of which is optionally substituted by from 1 to 3 substituents selected from halogen, $C_{1-6}$ alkyl, phenyl, benzyl, Ophenyl, Obenzyl, $SO_2NH_2$, $SO_2NH(C_{1-6}$ alkyl), $SO_2N(C_{1-6}$ alkyl$)_2$, $CH_2COOH$, $CO_2H$, $CO_2Me$, $CO_2Et$, $CO_2iPr$, C(=O)$NH_2$, C(=O)NH($C_{1-6}$ alkyl), C(=O)N($C_{1-6}$ alkyl$)_2$, OH, $SC_{1-6}$ alkyl, $OC_{1-6}$ alkyl, $NO_2$, $NH_2$, $CF_3$, and CN.

In further embodiments, $R_1$ and each $R_2$ are independently hydrogen, $C_{1-6}$ alkyl, $C_{1-6}$ perhaloalkyl, $OC_{1-6}$ alkyl, $CO_16$ perhaloalkyl, halogen, thioalkyl, CN, OH, SH, $(CH_2)_nOSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)$ $NR_8R_9$, $NR_8R_9$, aryl, heterocyclo, C(=O)$R_{12}$, C(=O)aryl, C(=O)heterocyclo, OC(=O)aryl, OC(=O)heterocyclo, Oaryl, Oheterocyclo, C(=O)arylalkyl, OC(=O)arylalkyl, Oarylalkyl, alkenyl, alkynyl, or $NHCOR_8$.

In some preferred embodiments, Z is phenyl or substituted phenyl.

In further preferred embodiments, the compounds of the invention have the Formula IV:

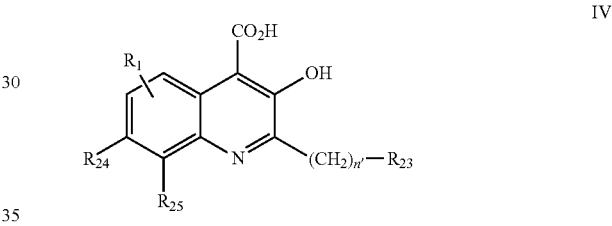

IV wherein:

n' is 0 or 1;

$R_1$ is hydrogen, halogen, OH, CN, SH, $C_{1-6}$ alkyl, $OC_{1-6}$ alkyl, $C_{1-6}$ perhaloalkyl, $C_{1-6}$ thioalkyl, aryl or heteroaryl;

wherein said aryl and said heteroaryl can each optionally be substituted with up to three substituents selected from halogen, OH, CN, SH, $NH_2$, $C_{1-6}$ alkyl, $OC_{1-6}$ alkyl, $C_{1-6}$ perhaloalkyl and $C_{1-6}$ thioalkyl; and wherein said $C_{1-6}$ alkyl, $OC_{1-6}$ alkyl and $C_{1-6}$ thioalkyl can each optionally be substituted with up to three substituents selected from halogen, OH, CN, SH, $NH_2$, $OC_{1-6}$ alkyl, $C_{1-6}$ perhaloalkyl and $C_{1-6}$ thioalkyl;

$R_{23}$ is aryl or heteroaryl, wherein said aryl and said heteroaryl can each optionally be substituted with up to three substituents selected from halogen, OH, CN, SH, $NH_2$, $C_{1-6}$ alkyl, $OC_{1-6}$ alkyl, $C_{1-6}$ perhaloalkyl and $C_{1-6}$ thioalkyl; and wherein $R_{24}$ and $R_{25}$ together form $-(CH_2)_3-$, $-(CH_2)_4-$, $-(CH_2)_2-NH-$, $-(CH_2)_2-NH-CH_2-$ or $-CH=CH-CH=CH-$, any of which can be substituted with up to three substituents selected from the group consisting of halogen, OH, CN, SH, $NH_2$, $OC_{1-6}$ alkyl, $C_{1-6}$ perhaloalkyl, C(=O)$R_{20}$, $SO_2R_{20}$ and $C_{1-6}$ thioalkyl.

In some embodiments, $R_{23}$ is optionally substituted aryl, preferably optionally substituted phenyl. Preferably, the phenyl is substituted at the 4-position thereof, preferably by a substituent selected from halogen, OH, CN, SH, $NH_2$, $CH_3$, $OCH_3$, $CF_3$ and $OCF_3$, preferably halogen and $OCF_3$, more preferably Cl and $OCF_3$.

In some embodiments, $R_{24}$ and $R_{25}$ together form unsubstituted $-(CH_2)_3-$, $-(CH_2)_4-$, $-(CH_2)_2-NH-$, $-(CH_2)_2-NH-CH_2-$ or $-CH=CH-CH=CH-$.

In some preferred embodiments, $R_1$ is H; and $R_{24}$ and $R_{25}$ together form unsubstituted —$(CH_2)_3$—. In further preferred embodiments, $R_1$ is H; and $R_{24}$ and $R_{25}$ together form unsubstituted —$(CH_2)_4$—. In further preferred embodiments, $R_1$ is H; and $R_{24}$ and $R_{25}$ together form unsubstituted —$(CH_2)_2$—NH—. In still further preferred embodiments, $R_1$ is H; and $R_{24}$ and $R_{25}$ together form unsubstituted —CH═CH—CH═CH—. In some further embodiments, $R_1$ is H; and $R_{24}$ and $R_{25}$ together form optionally substituted —$(CH_2)_2$—NH—$CH_2$—.

In some preferred embodiments, the present invention provides the compounds 2-(4-Chloro-phenyl)-3-hydroxy-benzo[h]quinoline-4-carboxylic acid; 2-(4-Chloro-phenyl)-3-hydroxy-7,8,9,10-tetrahydro-benzo[h]quinoline-4-carboxylic acid; 3-Hydroxy-2-(4-trifluoromethoxy-benzyl)-7,8,9,10-tetrahydro-benzo[h]quinoline-4-carboxylic acid; 8-(4-Chloro-benzyl)-7-hydroxy-2,3-dihydro-1H-aza-cyclopenta[a]naphthalene-6-carboxylic acid; 8-(4-Chloro-benzyl)-7-hydroxy-2,3-dihydro-1H-pyrrolo[3,2-h]quinoline-6-carboxylic acid; f) 2-(4-Chloro-benzyl)-3-hydroxy-7,8,9,10-tetrahydro-benzo[h]quinoline-4-carboxylic acid; Triethylammonium 7,8-benzo-2-(4-chlorophenyl)-3-hydroxyquinoline-4-carboxylate; 2-(3,4-Dichlorobenzyl)-3-hydroxy-7,8,9,10-tetrahydrobenzo[h]quinoline-4-carboxylic acid; 3-Hydroxy-2-(thiophen-2-ylmethyl)-7,8,9,10-tetrahydrobenzo[h]quinoline-4-carboxylic acid; 2-(Benzo[b]thiophen-3-ylmethyl)-3-hydroxy-7,8,9,10-tetrahydrobenzo[h]quinoline-4-carboxylic acid; 2-(2-Chlorobenzyl)-3-hydroxy-7,8,9,10-tetrahydrobenzo[h]quinoline-4-carboxylic acid; 2-(3-Chlorobenzyl)-3-hydroxy-7,8,9,10-tetrahydrobenzo[h]quinoline-4-carboxylic acid; 3-Hydroxy-2-[2-(3-methylbenzo[b]thiophen-2-ylmethyl)]-7,8,9,10-tetrahydrobenzo[h]quinoline-4-carboxylic acid; 3-Hydroxy-2-(thiophen-3-ylmethyl)-7,8,9,10-tetrahydrobenzo[h]quinoline-4-carboxylic acid; 3-Hydroxy-2-(indol-3-ylmethyl)-7,8,9,10-tetrahydrobenzo[h]quinoline-4-carboxylic acid; 2-(5-Chlorobenzo[b]thiophen-3-ylmethyl)-3-hydroxy-7,8,9,10-tetrahydrobenzo[h]quinoline-4-carboxylic acid; 3-Hydroxy-2-phenyl-7,8,9,10-tetrahydro-benzo[h]quinoline-4-carboxylic acid; 2-(4-Cyano-benzyl)-3-hydroxy-7,8,9,10-tetrahydro-benzo[h]quinoline-4-carboxylic acid; 2-(4-Carboxy-benzyl)-3-hydroxy-7,8,9,10-tetrahydro-benzo[h]quinoline-4-carboxylic acid; 2-(4-Carbamoyl-benzyl)-3-hydroxy-7,8,9,10-tetrahydro-benzo[h]quinoline-4-carboxylic acid; 2-Benzyl-3-hydroxy-7,8,9,10-tetrahydro-benzo[h]quinoline-4-carboxylic acid; 3-Hydroxy-2-phenethyl-7,8,9,10-tetrahydro-benzo[h]quinoline-4-carboxylic acid; 2-(4-Chloro-benzyl)-3-hydroxy-7,8,9,10-tetrahydro-[1,9]phenanthroline-4-carboxylic acid; 2-(4-Chloro-benzyl)-3-hydroxy-9-isopropyl-7,8,9,10-tetrahydro-[1,9]phenanthroline-4-carboxylic acid; 9-Benzyl-2-(4-chlorobenzyl)-3-hydroxy-7,8,9,10-tetrahydro-[1,9]phenanthroline-4-carboxylic acid; 2-(4-Chloro-benzyl)-9-ethyl-3-hydroxy-7,8,9,10-tetrahydro-[1,9]phenanthroline-4-carboxylic acid; 9-Acetyl-2-(4-chloro-benzyl)-3-hydroxy-7,8,9,10-tetrahydro-[1,9]phenanthroline-4-carboxylic acid; 9-Carbamoyl-2-(4-chloro-benzyl)-3-hydroxy-7,8,9,10-tetrahydro-[1,9]phenanthroline-4-carboxylic acid; 9-Benzoyl-2-(4-chlorobenzyl)-3-hydroxy-7,8,9,10-tetrahydro-[1,9]phenanthroline-4-carboxylic acid; 9-Benzoyl-3-benzoyloxy-2-(4-chloro-benzyl)-7,8,9,10-tetrahydro-[1,9]phenanthroline-4-carboxylic acid; 2-(4-Chloro-benzyl)-3-hydroxy-9-methanesulfonyl-7,8,9,10-tetrahydro-[1,9]phenanthroline-4-carboxylic acid; 2-(4-Chloro-benzyl)-3-hydroxy-7,10-dihydro-8H-[1,9]phenanthroline-4,9-dicarboxylic acid 9-ethyl ester; 2-(4-Chlorobenzyl)-3-ethoxycarbonyloxy-7,10-dihydro-8H-[1,9]phenanthroline-4,9-dicarboxylic acid 9-ethyl ester; 2-(4-Chloro-benzyl)-3-hydroxy-9-phenylacetyl-7,8,9,10-tetrahydro-[1,9]phenanthroline-4-carboxylic acid; 2-(4-Chloro-benzyl)-3-hydroxy-9-(propane-2-sulfonyl)-7,8,9,10-tetrahydro-[1,9]phenanthroline-4-carboxylic acid; 2-(4-Chlorobenzyl)-3-methoxy-7,8,9,10-tetrahydro-benzo[h]quinoline-4-carboxylic acid; 3-Hydroxy-2-piperidin-4-yl-7,8,9,10-tetrahydro-benzo[h]quinoline-4-carboxylic acid; or 2-(1-acetyl-piperidin-4-yl)-3-hydroxy-7,8,9,10-tetrahydro-benzo[h]quinoline-4-carboxylic acid.

Also provided in accordance with the present invention are compositions comprising a pharmaceutically effective amount of a compound according of the invention, and a pharmaceutically acceptable carrier or excipient.

The present invention also provides methods for using the compounds disclosed herein. In some embodiments, the invention provides methods of inhibiting selectin-mediated intracellular adhesion in a mammal comprising administering to the mammal an effective amount of a compound of the invention.

In further embodiments, the invention provides methods of inhibiting selectin-mediated intracellular adhesion associated with a disease, disorder, condition or undesired process in a mammal, the method comprising administering to the mammal an effective amount of a compound of the invention.

In some preferred embodiments, the disease, disorder, condition or undesired process is inflammation, infection, metastasis, an undesired immunological process, or an undesired thrombotic process.

In some preferred embodiments, the disease, disorder, condition or undesired process is atherosclerosis, restenosis, myocardial infarction, Reynauld's syndrome, inflammatory bowel disease, osteoarthritis, acute respiratory distress syndrome, asthma, emphysema, delayed type hypersensitivity reaction, thermal injury, experimental allergic encephalomyelitis, multiple organ injury syndrome secondary to trauma, neutrophilic dermatosis (Sweet's disease), glomerulonephritis, ulcerative colitis, Crohn's disease, necrotizing enterocolitis, cytokine-induced toxicity, gingivitis, periodontitis, hemolytic uremic syndrome, psoriasis, systemic lupus erythematosus, autoimmune thyroiditis, multiple sclerosis, rheumatoid arthritis, Grave's disease, immunological-mediated side effects of treatment associated with hemodialysis or leukapheresis, granulocyte transfusion associated syndrome, deep vein thrombosis, unstable angina, transient ischemic attacks, peripheral vascular disease, metastasis associated with cancer, sickle syndromes, including but not limited to sickle cell anemia, or congestive heart failure.

In some embodiments, the disease, disorder, condition or undesired process is an undesired infection process mediated by a bacteria, a virus, or a parasite, for example gingivitis, periodontitis, hemolytic uremic syndrome, or granulocyte transfusion associated syndrome.

In further embodiments, the disease, disorder, condition or undesired process is metastasis associated with cancer.

In further embodiments, the disease, disorder, condition or undesired process is a disease or disorder associated with an undesired immunological process, for example psoriasis, systemic lupus erythematosus, autoimmune thyroiditis, multiple sclerosis, rheumatoid arthritis, Grave's disease and immunological-mediated side effects of treatment associated with hemodialysis or leukapheresis.

In further embodiments, the disease, disorder, condition or undesired process is a condition associated with an undesired thrombotic process, for example deep vein thrombosis, unstable angina, transient ischemic attacks, peripheral vascular disease, or congestive heart failure.

In further embodiments, the invention provides methods of ameliorating an undesired immunological process in a transplanted organ comprising administering to the organ a compound of the invention.

In some embodiments, the invention provides methods for treating, or ameliorating a symptom of a sickle syndrome, for example sickle cell anemia, comprising administering a compound of the invention to a patient in need thereof.

In some further embodiments, the invention provides methods comprising identifying a human, mammal or animal as having a biomarker for a disease or disorder involving selectin-mediated intracellular adhesion; and administering to said human, mammal or animal a therapeutically effective amount of a compound as disclosed herein. In some embodiments, the biomarker is one or more of CD 40, CD 40 Ligand, MAC-1, TGF beta, ICAM, VCAM, IL-1, IL-6, IL-8, Eotaxin, RANTES, MCP-1, PlGF, CRP, SAA, and platelet monocyte aggregates.

DETAILED DESCRIPTION

The present invention provides, in some embodiments, methods and compounds for antagonizing selecting-mediated intercellular adhesion. Interfering or preventing such intercellular adhesion is useful both in the treatment of a variety of diseases and disorders, as well as for ameliorating one or more symptoms of such diseases or disorders. Thus, in some embodiments, the present invention provides methods of inhibiting selectin-mediated intracellular adhesion in a mammal, particularly where such selectin-mediated intracellular adhesion is associated with a disease, disorder, condition or undesired process in a mammal, comprising administering to the mammal an effective amount of a compound of the invention.

Diseases, disorders, conditions and undesired processes amendable to the methods of the invention include all those that are wholly or in part characterized by undesired selectin-mediated intercellular adhesion, for example inflammation, infection (for example mediated by a bacteria, a virus, or a parasite, including for example gingivitis, periodontitis, hemolytic uremic syndrome, and granulocyte transfusion associated syndrome), metastasis (for example associated with cancer), undesired immunological processes, and undesired thrombotic processes. Nonlimiting examples of the foregoing include atherosclerosis, restenosis, myocardial infarction, Reynauld's syndrome, inflammatory bowel disease, osteoarthritis, acute respiratory distress syndrome, asthma, emphysema, delayed type hypersensitivity reaction, thermal injury such as burns or frostbite, experimental allergic encephalomyelitis, multiple organ injury syndrome secondary to trauma, neutrophilic dermatosis (Sweet's disease), glomerulonephritis, ulcerative colitis, Crohn's disease, necrotizing enterocolitis, cytokine-induced toxicity, gingivitis, periodontitis, hemolytic uremic syndrome, psoriasis, systemic lupus erythematosus, autoimmune thyroiditis, multiple sclerosis, rheumatoid arthritis, Grave's disease, immunological-mediated side effects of treatment associated with hemodialysis or leukapheresis, granulocyte transfusion associated syndrome, deep vein thrombosis, unstable angina, transient ischemic attacks, peripheral vascular disease, stroke and congestive heart failure.

The infection process involves selectin-mediated intercellular adhesion. Thus, the present invention also provides methods of treating or preventing an undesired infection process in a mammal, comprising administering to said mammal a compound of the invention. The infection can be mediated by a bacteria, a virus, or a parasite, and examples of such infection processes include gingivitis, periodontitis, hemolytic uremic syndrome, and granulocyte transfusion associated syndrome.

Further examples of diseases and disorders that involve selectin-mediated intercellular adhesion include metastasis in cancer, and diseases or disorders associated with an undesired immunological processes, for example psoriasis, systemic lupus erythematosus, autoimmune thyroiditis, multiple sclerosis, rheumatoid arthritis, Grave's disease and immunological-mediated side effects of treatment associated with hemodialysis or leukapheresis.

A further example is in organ transplantation, wherein patients generally receive immunosuppressive therapy to minimize the possibility of rejection of the organ. Typical immunosuppressive agents used for such therapeutic regimes include cyclosporine, rapamycin and tacrolimus. In some embodiments of the invention, a compound of the invention can be administered to the patient to receive the organ transplant in conjunction with one or more such immunosuppressive agents. Thus, in some embodiments, the compound of the invention can be administered to an organ for transplant, by, for example, administering the compound to the patient prior to transplant, to the patient after transplant, or directly to the transplanted organ itself either before or after transplant (for example by perfusion), or in any combination. Thus, in preferred embodiments, the compound of the invention can be administered to an organ in conjunction with one or more immunosuppressive agents; i.e., the compound can be administered at the same time as an immunosuppressive agent, or at any time during which an immunosuppressive agent is present in effective amounts in the organ or patient.

Further examples of processes involving selectin-mediated intercellular adhesion which are amenable to the methods of the invention include conditions associated with an undesired thrombotic process, for example deep vein thrombosis, unstable angina, transient ischemic attacks, peripheral vascular disease, or congestive heart failure.

The compounds of the invention also find use in the treatment of sickle syndromes, for example sickle cell anemia, and in ameliorating one or more symptoms of such disorders.

In some embodiments, the compounds of the invention find use in treatment of then aforementioned diseases and/or disorders when administered in combination with other therapeutic agents. For example, in some embodiments, the compounds of the invention can beneficially be administered to patients with vascular diseases, for example CAD (coronary artery disease, including but not limited to acute coronary syndrome (e.g., MI and stroke)), peripheral vascular disease including PAD (peripheral artery disease), and deep vein thrombosis, along with an anti-platelet agent, such as Plavix or aspirin, and/or lipid modulators such as, for example statins Other suitable anti-platelet agents and lipid modulators will be apparent to those of skill in the art.

The compounds of the invention further find use in the treatment of diseases and disorders implicated by biomarkers as are known in the art. Nonlimiting biomarkers include, for example, CD 40, CD 40 Ligand, MAC-1, TGF beta, ICAM, VCAM, IL-1, IL-6, IL-8, Eotaxin, RANTES, MCP-1, PlGF, CRP and SAA, as well as platelet monocyte aggregates.

Generally, the methods include the administration to a mammal in need of treatment a compound of Formula I, Formula II, Formula II, Formula IV, or a composition comprising a compound of Formula I, Formula II, Formula III or Formula IV. In accordance with some preferred embodiments, methods of the invention include administration of one or more compounds having the Formula I:

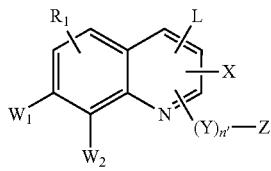

wherein the constituent variables are as defined herein.

In some embodiments, $W_1$ and $W_2$ taken together with the atoms to which they are attached form a 5 member carbocyclic ring or a 6 member carbocyclic ring optionally substituted as described above. In further embodiments, $W_1$ and $W_2$ taken together with the atoms to which they are attached form a 5 member or 6 member heterocyclic ring that is optionally substituted as above, e.g., having up to 3 or 4 heteroatoms, in which the heteroatom or heteroatoms are independently selected from O, N, S and $NR_{13}$, such as pyrrolidine, pyrroline, tetrahydrothiophene, dihydrothiophene, tetrahydrofuran, dihydrofuran, imidazoline, tetrahydroimidazole, dihydropyrazole, tetrahydropyrazole, oxazoline, piperidine, dihydropyridine, tetrahydropyridine, dihydropyran, tetrahydropyran, dioxane, piperazine, dihydropyrimidine, tetrahydropyrimidine, morpholine, thioxane, thiomorpholine, pyrrole, porphyrin, furan, thiophene, pyrazole, imidazole, oxazole, oxadiazole, isoxazole, thiazole, thiadiazole, isothiazole, pyridine, pyrimidine, pyrazine, pyran and triazine. It should be noted that wherein $W_1$ and $W_2$ taken together with the atoms to which they are attached form a saturated ring, such as a piperidine ring, it is understood that the bond between $W_1$ and $W_2$ remains unsaturated.

In accordance with some preferred embodiments, methods of the invention include administration of one or more compounds having the Formula II:

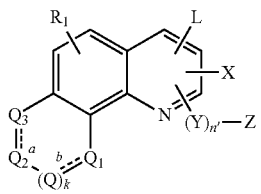

wherein the constituent variables are as defined herein.

In some embodiments of the compounds and methods of the invention, Y is $CR_3R_4$, preferably $CH_2$, and more preferably where X is OH. In some particularly preferred embodiments, Y is $CH_2$, X is OH and Z is aryl, more preferably phenyl or substituted phenyl. In some especially preferred embodiments, Z is phenyl substituted at the 4'-position. In some embodiments, such 4'-substitutents are small hydrophobic groups such as halogens, $C_{1-6}$ alkyl, $C_{1-6}$ perhaloalkyl, $OC_{1-6}$ alkyl, $OC_{1-6}$ perhaloalkyl, $C_{1-6}$ thioalkyl, CN, alkylsulfonamides, and mono- and di-alkylamines.

In some preferred embodiments, preferably but not limited to those wherein Y is $CH_2$, X is OH, and Z is phenyl or substituted phenyl as described above, $R_1$ is a small hydrophobic group such as halogens, $C_{1-6}$ alkyl, $C_{1-6}$ perhaloalkyl, $OC_{1-6}$ alkyl, $OC_{1-6}$ perhaloalkyl, $C_{1-6}$ thioalkyl, CN, $C_{1-6}$ alklysulfonamides, $C_{1-6}$ mono- and di-alkylamines, or aryl or substituted aryl having up to 8 carbon atoms, wherein the substituents are selected from halogen, $C_{1-10}$ alkyl, $OC_{1-10}$ alkyl, CHO, $CO_2H$, $NO_2$, $NH_2$, CN, $CF_3$ and —OH.

In some preferred embodiments, substituents $(Y)_n$—Z, X and L are attached at the 2-, 3- and 4-positions of the quinoline, respectively, as shown below in Formula III:

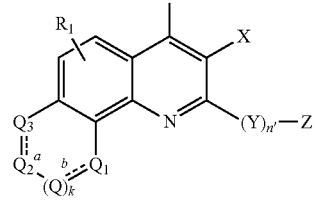

In some embodiments, k is 1, and bonds a and b are each single bonds. In further embodiments, k is 1, bonds a and b are each single bonds, and Q, $Q_1$, $Q_2$ and $Q_3$ are each independently $CHR_{2'}$, preferably $CH_2$.

In some embodiments, k is 0, bond a is a single bond, and $Q_1$, $Q_2$ and $Q_3$ are each independently $CHR_{2'}$, preferably $CH_2$.

In some embodiments, k is 0, bond a is a single bond, and $Q_1$ is $NR_{13}$, preferably NH, preferably wherein $Q_2$ and $Q_3$ are each $CH_2$.

In some embodiments, k is 1, bond a and bond b are each double bonds, and Q, $Q_1$, $Q_2$ and $Q_3$ are each $CR_2$, preferably $CH_2$.

In some embodiments, n' is 0. In other embodiments, n' is 1. In some embodiments wherein n' is 1, Y is $CR_3R_4$, preferably $CH_2$, preferably wherein X is OH. Preferably, L is $CO_2H$ or an ester thereof.

In some embodiments, n' is 0 and X is OH, preferably wherein L is $CO_2H$ or an ester thereof.

In some embodiments, Z is selected from:

(a) a five-membered heterocyclic ring containing one to three ring heteroatoms selected from N, S or O; wherein said five-membered heterocyclic ring is optionally substituted by from 1 to 3 substituents selected from halogen, $C_{1-10}$ alkyl, $OC_{1-10}$ alkyl, $NO_2$, $NH_2$, CN, $CF_3$, and $CO_2H$;

(b) a six-membered heterocyclic ring containing one to three ring heteroatoms selected from N, S or O; wherein said six-membered heterocyclic ring is optionally substituted by from 1 to 3 substituents selected from halogen, $C_{1-10}$ alkyl, $OC_{1-10}$ alkyl, CHO, $CO_2H$, $C(=O)R_{20}$, $SO_2R_{20}$, $NO_2$, $NH_2$, CN, $CF_3$ and OH;

(c) a bicyclic ring moiety optionally containing from 1 to 3 ring heteroatoms selected from N or O; wherein said bicyclic ring moiety is optionally substituted by from 1 to 3 substituents selected from halogen, $C_{1-6}$ alkyl, $OC_{1-6}$ alkyl, CHO, $NO_2$, $NH_2$, CN, $CF_3$, $CO_2H$, $C(=O)R_{20}$, $SO_2R_{20}$, and OH; and (d) a benzyl, naphthyl, or phenyl ring, each of which is optionally substituted by from 1 to 3 substituents selected from halogen, $C_{1-6}$ alkyl, phenyl, benzyl, Ophenyl, Obenzyl, $SO_2NH_2$, $SO_2NH(C_{1-6}$ alkyl), $SO_2N(C_{1-6}$ alkyl$)_2$, $CH_2COOH$, $CO_2H$, $CO_2Me$, $CO_2Et$, $CO_2iPr$, $C(=O)NH_2$, $C(=O)NH(C_{1-6}$ alkyl), $C(=O)N(C_{1-6}$ alkyl$)_2$, OH, $SC_{1-6}$ alkyl, $OC_{1-6}$ alkyl, $NO_2$, $NH_2$, $CF_3$, and CN.

In further embodiments, $R_1$ and each $R_2$ are independently hydrogen, $C_{1-6}$ alkyl, $C_{1-6}$ perhaloalkyl, $OC_{1-6}$ alkyl, $OC_{1-6}$ perhaloalkyl, halogen, thioalkyl, CN, OH, SH, $(CH_2)_n$ $OSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)NR_8R_9$, $NR_8R_9$, aryl, heterocyclo, $C(=O)R_{12}$, $C(=O)$aryl, $C(=O)$heterocyclo, $OC(=O)$aryl, $OC(=O)$heterocyclo, Oaryl, Oheterocyclo, C(=O)arylalkyl, OC(=O)arylalkyl, Oarylalkyl, alkenyl, alkynyl, or NHCOR$_8$.

In some preferred embodiments, Z is phenyl or substituted phenyl.

In further preferred embodiments, the compounds of the invention have the Formula IV:

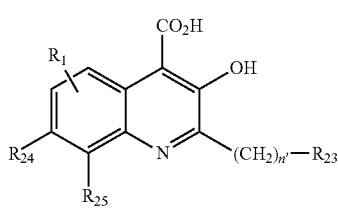

wherein:

n' is 0 or 1;

R$_1$ is H, halogen, OH, CN, SH, C$_{1-6}$ alkyl, OC$_{1-6}$ alkyl, C$_{1-6}$ perhaloalkyl, C$_{1-6}$ thioalkyl, aryl or heteroaryl;

wherein said aryl and said heteroaryl can each optionally be substituted with up to three substituents selected from halogen, OH, CN, SH, NH$_2$, C$_{1-6}$ alkyl, OC$_{1-6}$ alkyl, C$_{1-6}$ perhaloalkyl and C$_{1-6}$ thioalkyl; and wherein said C$_{1-6}$ alkyl OC$_{1-6}$ alkyl and C$_{1-6}$ thioalkyl can each optionally be substituted with up to three substituents selected from halogen, OH, CN, SH, NH$_2$, OC$_{1-6}$ alkyl, C$_{1-6}$ perhaloalkyl and C$_{1-6}$ thioalkyl;

R$_{23}$ is aryl or heteroaryl, wherein said aryl and said heteroaryl can each optionally be substituted with up to three substituents selected from halogen, OH, CN, SH, NH$_2$, C$_{1-6}$ alkyl, OC$_{1-6}$ alkyl, C$_{1-6}$ perhaloalkyl and C$_{1-6}$ thioalkyl; and wherein R$_{24}$ and R$_{25}$ together form —(CH$_2$)$_3$—, —(CH$_2$)$_4$—, —(CH$_2$)$_2$—NH—, 1-(CH$_2$)$_2$—NH—CH$_2$— or —CH=CH—CH=CH—, any of which can be substituted with up to three substituents selected from the group consisting of halogen, OH, CN, SH, NH$_2$, OC$_{1-6}$ alkyl, C$_{1-6}$ perhaloalkyl, C(=O)R$_{20}$, SO$_2$R$_{20}$ and C$_{1-6}$ thioalkyl.

In some embodiments, R$_{23}$ is optionally substituted aryl, preferably optionally substituted phenyl. Preferably, the phenyl is substituted at the 4-position thereof, preferably by a substituent selected from the group consisting of halogen, OH, CN, SH, NH$_2$, CH$_3$, OCH$_3$, CF$_3$ and OCF$_3$, preferably halogen and OCF$_3$, preferably by Cl and OCF$_3$.

In some embodiments, R$_{24}$ and R$_{25}$ together form unsubstituted —(CH$_2$)$_3$—, —(CH$_2$)$_4$—, —(CH$_2$)$_2$—NH—, —(CH$_2$)$_2$—NH—CH$_2$— or —CH=CH—CH=CH—.

In some preferred embodiments, R$_1$ is H; and R$_{24}$ and R$_{25}$ together form unsubstituted —(CH$_2$)$_3$—. In further preferred embodiments, R$_1$ is H; and R$_{24}$ and R$_{25}$ together form unsubstituted —(CH$_2$)$_4$—. In further preferred embodiments, R$_1$ is H; and R$_{24}$ and R$_{25}$ together form unsubstituted —(CH$_2$)$_2$—NH—. In still further preferred embodiments, R$_1$ is H; and R$_{24}$ and R$_{25}$ together form unsubstituted —CH=CH—CH=CH—. In some further embodiments, R$_1$ is H; and R$_{24}$ and R$_{25}$ together form optionally substituted —(CH$_2$)$_2$—NH—CH$_2$—.

In some preferred embodiments, the present invention provides the compounds 2-(4-Chloro-phenyl)-3-hydroxy-benzo[h]quinoline-4-carboxylic acid; 2-(4-Chloro-phenyl)-3-hydroxy-7,8,9,10-tetrahydro-benzo[h]quinoline-4-carboxylic acid; 3-Hydroxy-2-(4-trifluoromethoxy-benzyl)-7,8,9,10-tetrahydro-benzo[h]quinoline-4-carboxylic acid; 8-(4-Chloro-benzyl)-7-hydroxy-2,3-dihydro-1H-aza-cyclopenta[a]naphthalene-6-carboxylic acid; 8-(4-Chloro-benzyl)-7-hydroxy-2,3-dihydro-1H-pyrrolo[3,2-h]quinoline-6-carboxylic acid; f) 2-(4-Chloro-benzyl)-3-hydroxy-7,8,9,10-tetrahydro-benzo[h]quinoline-4-carboxylic acid; Triethylammonium 7,8-benzo-2-(4-chlorophenyl)-3-hydroxyquinoline-4-carboxylate; 2-(3,4-Dichlorobenzyl)-3-hydroxy-7,8,9,10-tetrahydrobenzo[h]quinoline-4-carboxylic acid; 3-Hydroxy-2-(thiophen-2-ylmethyl)-7,8,9,10-tetrahydrobenzo[h]quinoline-4-carboxylic acid; 2-(Benzo[b]thiophen-3-ylmethyl)-3-hydroxy-7,8,9,10-tetrahydrobenzo[h]quinoline-4-carboxylic acid; 2-(2-Chlorobenzyl)-3-hydroxy-7,8,9,10-tetrahydrobenzo[h]quinoline-4-carboxylic acid; 2-(3-Chlorobenzyl)-3-hydroxy-7,8,9,10-tetrahydrobenzo[h]quinoline-4-carboxylic acid; 3-Hydroxy-2-[2-(3-methylbenzo[b]thiophen-2-ylmethyl)]-7,8,9,10-tetrahydrobenzo[h]quinoline-4-carboxylic acid; 3-Hydroxy-2-(thiophen-3-ylmethyl)-7,8,9,10-tetrahydrobenzo[h]quinoline-4-carboxylic acid; 3-Hydroxy-2-(indol-3-ylmethyl)-7,8,9,10-tetrahydrobenzo[h]quinoline-4-carboxylic acid; 2-(5-Chlorobenzo[b]thiophen-3-ylmethyl)-3-hydroxy-7,8,9,10-tetrahydrobenzo[h]quinoline-4-carboxylic acid; 3-Hydroxy-2-phenyl-7,8,9,10-tetrahydro-benzo[h]quinoline-4-carboxylic acid; 2-(4-Cyano-benzyl)-3-hydroxy-7,8,9,10-tetrahydro-benzo[h]quinoline-4-carboxylic acid; 2-(4-Carboxy-benzyl)-3-hydroxy-7,8,9,10-tetrahydro-benzo[h]quinoline-4-carboxylic acid; 2-(4-Carbamoyl-benzyl)-3-hydroxy-7,8,9,10-tetrahydro-benzo[h]quinoline-4-carboxylic acid; 2-Benzyl-3-hydroxy-7,8,9,10-tetrahydro-benzo[h]quinoline-4-carboxylic acid; 3-Hydroxy-2-phenethyl-7,8,9,10-tetrahydro-benzo[h]quinoline-4-carboxylic acid; 2-(4-Chloro-benzyl)-3-hydroxy-7,8,9,10-tetrahydro-[1,9]phenanthroline-4-carboxylic acid; 2-(4-Chloro-benzyl)-3-hydroxy-9-isopropyl-7,8,9,10-tetrahydro-[1,9]phenanthroline-4-carboxylic acid; 9-Benzyl-2-(4-chlorobenzyl)-3-hydroxy-7,8,9,10-tetrahydro-[1,9]phenanthroline-4-carboxylic acid; 2-(4-Chloro-benzyl)-9-ethyl-3-hydroxy-7,8,9,10-tetrahydro-[1,9]phenanthroline-4-carboxylic acid; 9-Acetyl-2-(4-chloro-benzyl)-3-hydroxy-7,8,9,10-tetrahydro-[1,9]phenanthroline-4-carboxylic acid; 9-Carbamoyl-2-(4-chloro-benzyl)-3-hydroxy-7,8,9,10-tetrahydro-[1,9]phenanthroline-4-carboxylic acid; 9-Benzoyl-2-(4-chlorobenzyl)-3-hydroxy-7,8,9,10-tetrahydro-[1,9]phenanthroline-4-carboxylic acid; 9-Benzoyl-3-benzoyloxy-2-(4-chloro-benzyl)-7,8,9,10-tetrahydro-[1,9]phenanthroline-4-carboxylic acid; 2-(4-Chloro-benzyl)-3-hydroxy-9-methanesulfonyl-7,8,9,10-tetrahydro-[1,9]phenanthroline-4-carboxylic acid; 2-(4-Chloro-benzyl)-3-hydroxy-7,10-dihydro-8H-[1,9]phenanthroline-4,9-dicarboxylic acid 9-ethyl ester; 2-(4-Chlorobenzyl)-3-ethoxycarbonyloxy-7,10-dihydro-8H-[1,9]phenanthroline-4,9-dicarboxylic acid 9-ethyl ester; 2-(4-Chloro-benzyl)-3-hydroxy-9-phenylacetyl-7,8,9,10-tetrahydro-[1,9]phenanthroline-4-carboxylic acid; 2-(4-Chloro-benzyl)-3-hydroxy-9-(propane-2-sulfonyl)-7,8,9,10-tetrahydro-[1,9]phenanthroline-4-carboxylic acid; 2-(4-Chlorobenzyl)-3-methoxy-7,8,9,10-tetrahydro-benzo[h]quinoline-4-carboxylic acid; 3-Hydroxy-2-piperidin-4-yl-7,8,9,10-tetrahydro-benzo[h]quinoline-4-carboxylic acid; or 2-(1-acetyl-piperidin-4-yl)-3-hydroxy-7,8,9,10-tetrahydro-benzo[h]quinoline-4-carboxylic acid.

It will be understood that compounds of Formulas I, II, III and IV can have one or more chiral centers, and exist as enantiomers or diastereomers. The invention is to be understood to extend to all such enantiomers, diastereomers and mixtures thereof, including racemates.

It is contemplated that the present invention also include all possible protonated and unprotonated forms of the compounds described herein, as well as solvates, tautomers and pharmaceutically acceptable salts thereof.

In some embodiments, substituent L is CO₂H, an ester thereof, or a pharmaceutically acceptable acid mimetic. As used herein, the term "acid mimetic" is intended to include moieties that mimic acid functionality in biological molecules. Examples of such acid mimetics are known in the art, and include without limitation —OH and those shown below:

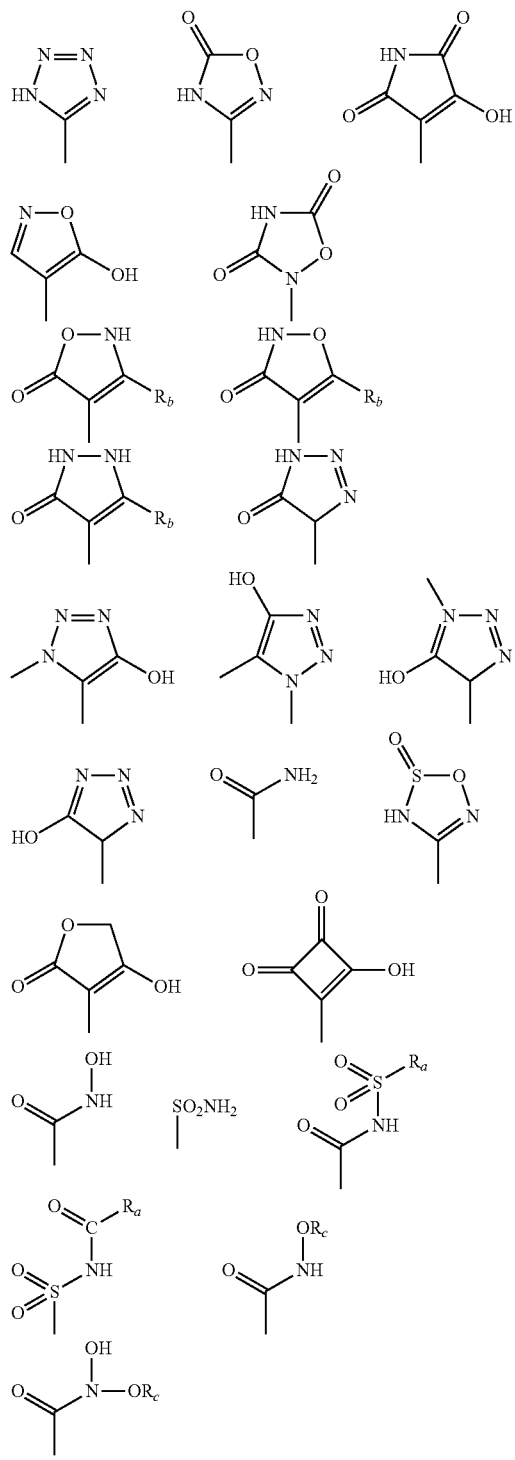

wherein:
$R_a$ is selected from —$CF_3$, $CH_3$, phenyl or benzyl, where the phenyl or benzyl is optionally substituted by up to three groups selected from $C_{1-6}$ alkyl, $C_{1-6}$ alkoxy, $C_{1-6}$ thioalkyl, —$CF_3$, halogen, —OH or COOH;

$R_b$ is selected from —$CF_3$, —$CH_3$, —$NH_2$, phenyl or benzyl, where the phenyl or benzyl is optionally substituted by up to three groups selected from $C_{1-6}$ alkyl, $C_{1-6}$ alkoxy, $C_{1-6}$ thioalkyl, —$CF_3$, halogen, —OH or COOH, and $R_c$ is selected from —$CF_3$ and $C_{1-6}$ alkyl Ester forms of the present compounds (for example compounds where L is an ester of CO₂H) include the pharmaceutically acceptable ester forms known in the art including those which can be metabolized into the free acid form, such as a free carboxylic acid form, in the animal body, such as the corresponding alkyl esters (e.g., alkyl of 1 to 10 carbon atoms), cycloalkyl esters, (e.g., of 3-10 carbon atoms), aryl esters (e.g., of 6-20 carbon atoms) and heterocyclic analogues thereof (e.g., of 3-20 ring atoms, 1-3 of which can be selected from oxygen, nitrogen and sulfur heteroatoms) can be used according to the invention, where alkyl esters, cycloalkyl esters and aryl esters are preferred and the alcoholic residue can carry further substituents. $C_1$-$C_8$ alkyl esters, preferably $C_1$-$C_6$ alkyl esters, such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester are particularly preferred.

As used herein, the term alkyl as a group or part of a group is intended to denote hydrocarbon groups including straight chain, branched and cyclic hydrocarbons, e.g., of 1-20, such as 1-6, carbon atoms, including for example but not limited to methyl, ethyl, n-propyl, isopropyl, cyclopropyl, n-butyl, sec-butyl, tert-butyl, cyclobutyl, cyclopropylmethyl, n-pentyl, isopentyl, tert-pentyl, cyclopentyl, cyclopentylmethyl, n-hexyl, cyclohexyl, and the like. Throughout this specification, it should be understood that the term alkyl is intended to encompass both non-cyclic hydrocarbon groups and cyclic hydrocarbon groups. In some embodiments of the compounds of the invention, alkyl groups are non-cyclic. In further embodiments, alkyl groups are cyclic, and in further embodiments, alkyl groups are both cyclic and noncyclic.

Alkyl groups of the compounds and methods of the invention can include optional substitution with from one halogen up to perhalogenation. In some embodiments, perfluoro groups are preferred. Examples of alkyl groups optionally substituted with halogen include $CF_3$, $CH_2CF_3$, $CCl_3$, $CH_2CH_2CF_2CH_3$, $CH(CF_3)_2$, and $(CH_2)_6$—$CF_2CCl_3$.

As used herein, the term alkenyl is intended to denote alkyl groups that contain at least one double bond, e.g., 2-20, preferably 2-6 carbon atoms, including for example but not limited to vinyl, allyl, 2-methyl-allyl, 4-but-3-enyl, 4-hex-5-enyl, 3-methyl-but-2-enyl, cyclohex-2-enyl and the like.

As used herein, the term alkynyl is intended to denote alkyl groups that include at least one triple bond, e.g., 2-20, preferably 2-6 carbon atoms, including for example but not limited to but-1-yne, propyne, pent-2-yne, ethynyl-cyclohexyl and the like.

Alkyl, alkenyl and alkynyl groups as defined above may also be optionally substituted i.e., they can optionally bear further substituent groups. Some preferred substituent groups include hydroxy, alkoxy (i.e., O-alkyl, preferably O—$C_{1-6}$ alkyl), mono-, di- or trihaloalkoxy (e.g., —O—$CX_3$ where X is halogen), —$(CH_2)_n NH_2$, and —$(CH_2)_n NHBoc$.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, isopropyl, n-butyl, sec-butyl, isobutyl, etc. As used herein, the term halogen has its normal meaning of group seven elements, including F, Cl, Br and I.

As used herein, the term "carbocyclic ring" is intended to denote a saturated, partially saturated or aromatic ring system in which the ring atoms are each carbon.

As used herein the term aryl as a group or part of a group is intended to mean an aromatic hydrocarbon system, for example phenyl, naphthyl, phenanthrenyl, anthracenyl, pyrenyl, and the like, e.g., of 6-20, preferably 6-10 carbon atoms. In some embodiments, aryl groups are a naphthyl or phenyl ring, respectively, each of which is optionally substituted by from 1 to 3 substituents selected from halogen, $C_1$-$C_6$ alkyl, phenyl, benzyl, O-phenyl, O-benzyl, —$SO_2NH_2$, —$SO_2NH$($C_{1-6}$ alkyl), $SO_2N(C_{1-6}$ alkyl$)_2$, $CH_2COOH$, $CO_2H$, $CO_2Me$, $CO_2Et$, $CO_2iPr$, C(=O)$NH_2$, C(=O)NH($C_1$-$C_6$), C(=O)N($C_1$-$C_6)_2$, OH, $SC_{1-6}$ alkyl, $OC_{1-6}$ alkyl, $NO_2$, $NH_2$, $CF_3$, $OCF_3$ and CN.

As used herein, the term arylalkyl is intended to mean a group of formula -alkyl-aryl, wherein aryl and alkyl have the definitions above. In some embodiments, the arylalkyl group is a benzyl group that is optionally substituted by from 1 to 3 substituents selected from halogen, $C_{1-6}$ alkyl, phenyl, benzyl, Ophenyl, Obenzyl, $SO_2NH_2$, $SO_2NH(C_{1-6}$ alkyl), $SO_2N(C_1$ alkyl$)_2$, $CH_2COOH$, $CO_2H$, $CO_2Me$, $CO_2Et$, $CO_2iPr$, C(=O)$NH_2$, C(=O)NH($C_{1-6}$ alkyl), C(=O)N($C_{1-6}$ alkyl$)_2$, OH, $SC_{1-6}$ alkyl, $OC_{1-6}$ alkyl, $NO_2$, $NH_2$, $CF_3$, $OCF_3$ and CN.

As used herein, the term heterocyclo as a group or part of a group is intended to mean a mono- or bi-cyclic ring system that contains from one to three hetero (i.e., non-carbon) atoms selected from O, N and S and for example 3-20 ring atoms. Heterocyclo groups include fully saturated and partially saturated cyclic heteroatom-containing moieties (containing for example none, or one or more double bonds). Such fully and partially saturated cyclic non-aromatic groups are also collectively referred to herein as "heterocycloalkyl" groups. Heterocyclo groups also include cyclic heteroatom-containing moieties that contain at least one aromatic ring. Such fully and partially aromatic moieties are also collectively referred to herein as "heteroaryl" groups. In some embodiments, heterocyclo groups are:

(a) a five-membered heterocyclic ring containing one to three ring heteroatoms selected from N, S or O exemplified by, but not limited to, furan, imidazole, imidazolidine, isothiazole, isoxazole, oxathiazole, oxazole, oxazoline, pyrazole, pyrazolidine, pyrazoline, pyrrole, pyrrolidine, pyrroline, thiazoline, or thiophene, the five-membered heterocyclic ring being optionally substituted by from 1 to 3 substituents selected from halogen, $C_{1-10}$ alkyl, preferably $C_{1-6}$ alkyl, $OC_{1-10}$ alkyl, preferably $OC_{1-6}$ alkyl, $NO_2$, $NH_2$, CN, $CF_3$, $CO_2H$; or (b) a six-membered heterocyclic ring containing one to three ring heteroatoms selected from N, S or O exemplified by, but not limited to morpholine, oxazine, piperazine, piperidine, pyran, pyrazine, pyridazine, pyridine, pyrimidine, thiadizine, or thiazine, the six-membered heterocyclic ring being optionally substituted by from 1 to 3 substituents selected from halogen, $C_{1-10}$ alkyl, $OC_{1-10}$ alkyl, CHO, $CO_2H$, C(=O)$R_{20}$, $SO_2R_{20}$, $NO_2$, $NH_2$, CN, $CF_3$ or OH; or (c) a bicyclic ring moiety optionally containing from 1 to 3 ring heteroatoms selected from N or O exemplified by, but not limited to, benzodioxine, benzodioxole, benzofuran, chromene, cinnoline, indazole, indole, indoline, indolizine, isoindole, isoindoline, isoquinoline, napthalene, napthyridine, phthalazine, purine, quinazoline, quinoline, or quinolizine, the bicyclic ring moiety being optionally substituted by from 1 to 3 substituents selected from halogen, $C_{1-6}$ alkyl, $OC_{1-6}$ alkyl, CHO, $NO_2$, $NH_2$, CN, $CF_3$, $CO_2H$, C(=O)$R_{20}$, $SO_2R_{20}$, or OH.

The compounds according to the invention can exist as pharmaceutically acceptable salts, including pharmaceutically acceptable acid addition salts prepared from pharmaceutically acceptable acids, including inorganic and organic acids. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Further representative examples of pharmaceutically acceptable salts can be found in, *Journal of Pharmaceutical Science*, 66, 2 (1977), incorporated herein by reference. Reacting compounds of this invention with one or more equivalents of an appropriately reactive base may also prepare basic salts. Both mono and polyanionic salts are contemplated, depending on the number of acidic hydrogens available for deprotonation. Appropriate bases can be either organic or inorganic in nature. For example, inorganic bases such as $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, $Na_3PO_4$ as well as others are suitable. Organic bases including amines, alkyl amines, dialkylamines, trialkylamines, various cyclic amines (such as pyrrolidine, piperidine, etc) as well as other organic amines are suitable. Quaternary ammonium alkyl salts may also prepared by reacting a compound of the invention with an appropriately reactive organic electrophile (such as methyl iodide or ethyl triflate). The compounds described herein can also be administered in the form of liposomes. As is known in the art, liposomes are generally derived from phospholipids or other lipid substances, and are formed by mono or multilamellar hydrated liquid crystals that are dispersed in an aqueous medium. Any nontoxic, pharmacologically acceptable lipid capable of forming liposomes can be used.

Liposome-containing compositions in accordance with the present invention can contain, in addition to the compound of Formula I, II, III or IV, stabilizers, preservatives, excipients and the like. The preferred lipids include phospholipids, including phosphatidyl cholines (lecithins), both natural and synthetic. Methods for liposome formation are well known in the art, and will be apparent to the skilled artisan.

The present invention also includes compounds of Formulas I, II, III and IV in prodrug form. In general, the inclusion of a physiologically labile group on a compound of the invention will result in the regeneration of the desired compound when exposed to gastric juice, plasma, or in any tissue or compartment where the appropriate endogenous enzymes or reactive substances are present. One non-limiting example of such a physiogially labile group includes an alkyl ester of the carboxylic acid of the compound of Formulas I, II, III or IV. Such esters are known to undergo hydrolysis to the free acid either in the gut by gastric juice or in the plasma by various endogenous esterases. A further non-limiting example is replacement of the group X in Formula II or III with a group of formula O-G, where G is an alkyl group that is removed by metabolizing enzymes in the liver or gut, or with the moiety remaining after removal of the alpha carboxyl or amino group from a naturally occurring amino acid. Any such structure that imparts physiologically labile functionality is within the definition of prodrug as used herein.

The acid or base addition salts can be obtained as the direct products of compound synthesis. In the alternative, the free base can be dissolved in a suitable solvent containing the appropriate acid or base, and the salt isolated by evaporating the solvent or otherwise separating the salt and solvent. The compounds of this invention may form solvates with standard low molecular weight solvents using methods known to the skilled artisan.

Compositions of the invention may conveniently be administered in unit dosage form and can be prepared by any of the methods well known in the pharmaceutical art, for example, as described in *Remington's Pharmaceutical Sciences* (Mack Pub. Co., Easton, Pa., 1980), incorporated herein by reference in its entirety.

The compounds of the invention can be employed as the sole active agent in a pharmaceutical or can be used in combination with other active ingredients, which could facilitate the therapeutic effect of the compound.

Compounds of the present invention or a solvate or physiologically functional derivative thereof can be used as active ingredients in pharmaceutical compositions, specifically as selectin inhibitors. The term "selectin inhibitor" is intended to mean a compound that interferes with (i.e., antagonizes) the normal physiological function of selectins in intercellular adhesion.

The term active ingredient in the context of pharmaceutical compositions of the invention is intended to mean a component of a pharmaceutical composition that provides the primary pharmaceutical benefit, as opposed to an inactive ingredient, which would generally be recognized as providing no pharmaceutical benefit. The term pharmaceutical composition is intended to mean a composition comprising at least one active ingredient and at least one ingredient that is not an active ingredient (for example and not limitation, a filler, dye, or a mechanism for slow release), whereby the composition is amenable to use for a specified, efficacious outcome in a mammal (for example, and not limitation, a human).

The compounds of Formulas I, II, III and IV are useful for the treatment or prophylaxis multiple disorders in mammals, including, but not limited to, human. Compounds of the present invention can be administered by oral, sublingual, parenteral, rectal, topical administration or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

Different amounts of the compounds of the present invention will be required to achieve the desired biological effect. The amount will depend on factors such as the specific compound, the use for which it is intended, the means of administration, and the condition of the treated individual and all of these dosing parameters are within the level of one of ordinary skill in the medicinal arts. A typical dose can be expected to fall in the range of 0.001 to 200 mg per kilogram of body weight of the mammal. Unit doses may contain from 1 to 200 mg of the compounds of the present invention and can be administered one or more times a day, individually or in multiples.

Pharmaceutical compositions, including at least one compound disclosed herein, and/or a pharmacologically acceptable salt or solvate thereof can be employed as an active ingredient combined with one or more carriers or excipients. Such compositions can be used in the treatment of clinical conditions for which a selectin inhibitor is indicated. The active ingredient or ingredients can be combined with the carrier in either solid or liquid form in a unit dose formulation. Formulations can be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives, and flavorings and colorants can be added to the liquid preparations. Parenteral dosage forms can be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

It is noted that when the selectin inhibitors are utilized as active ingredients in a pharmaceutical composition, these are not intended for use only in humans, but in non-human mammals as well. Those of ordinary skill in the art are readily credited with understanding the utility of such compounds in such settings.

This invention also provides a process for preparing a compound of formula I which comprises one of the following:

a) reacting a compound of formula

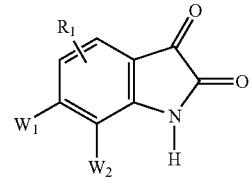

wherein $R_1$, $W_1$ and $W_2$ are as defined herein, with a compound of formula:

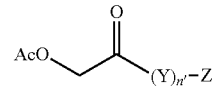

wherein Ac is acetyl and n', Y and Z are as defined herein to give a corresponding compound of formula I wherein L is $CO_2H$ in the 4 position and X is OH in the 3 position; or b) converting a compound of formula I to a pharmaceutically acceptable salt thereof or vice versa; or c) converting a compound of formula I having a reactive substituent group or site to a different compound of formula I; e.g., acylating a compound of formula I wherein $W_1$ and $W_2$ together form a heterocyclic ring having at least one NH heteroatom with an acylating agent containing an acyl or sulfonyl $R_{13}$ group, such as $C(=O)R_{20}$, $-SO_2R_{20}$, $SO_3R_{10}$, $C(=O)aryl$, $C(=O)heterocyclo$, $C(=O)arylalkyl$, and $R_{20}$ is selected from the group consisting of $C_{1-10}$ alkyl $OC_{1-10}$ alkyl and $NR_6R_7$, (for example see Schemes 29, 30 and 31 below);

or alkylating or acylating a compound of formula I having an —OH or —NH-moiety, see for example Schemes 27, 29 and 32.

The compounds of the present invention can be readily prepared according to a variety of synthetic manipulations, all of which would be familiar to one skilled in the art. A representative general synthesis is set forth below in the General Scheme below:

General Synthetic Scheme for the Preparation of Compounds of the Invention.

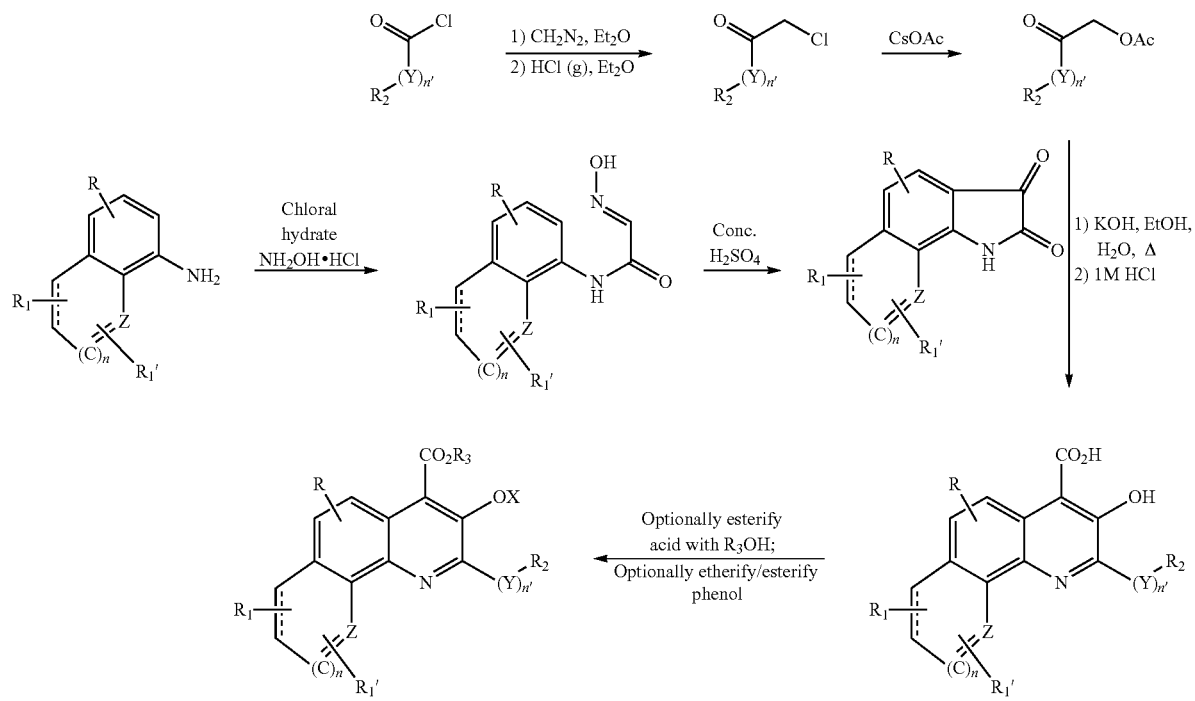

Those of skill in the art will appreciate that a wide variety of compounds of the invention can be prepared according to the General Scheme. For example, by starting with an appropriately substituted phenacetyl chloride one could prepare numerous differently substituted benzyl groups at the quinoline 2-position. Likewise, on skilled in the art also recognizes that variously substituted anilines can be purchased or prepared and used for the construction of variously substituted quinoline rings as described in, for example, Formula I. Additionally, protection of the carboxylic acid via esterification or some other masking reaction would allow for selective alkylation or functionalization of the 3-hydroxy group located on the quinoline ring.

In the synthesis of many compounds of the invention, protecting groups can be required to protect various functionality or functionalities during the synthesis. Representative protecting groups suitable for a wide variety of synthetic transformations are disclosed in Greene and Wuts, *Protective Groups in Organic Synthesis*, 2d ed, John Wiley & Sons, New York, 1991, the disclosure of which is incorporated herein by reference in its entirety.

While the present invention has been described with specificity in accordance with certain of its preferred embodiments, the following examples serve only to illustrate the invention and are not intended to limit the same.

EXAMPLES

Synthesis of Compounds

The compounds of Formula I included as examples herein can be prepared according to the following schemes and procedures from commercially available starting materials.

Scheme 1

Preparation of Compound 1

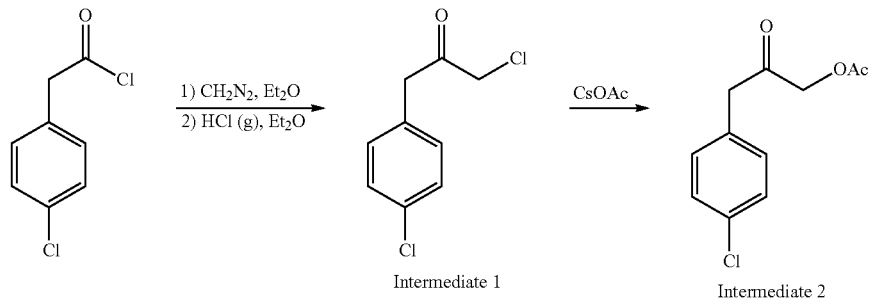

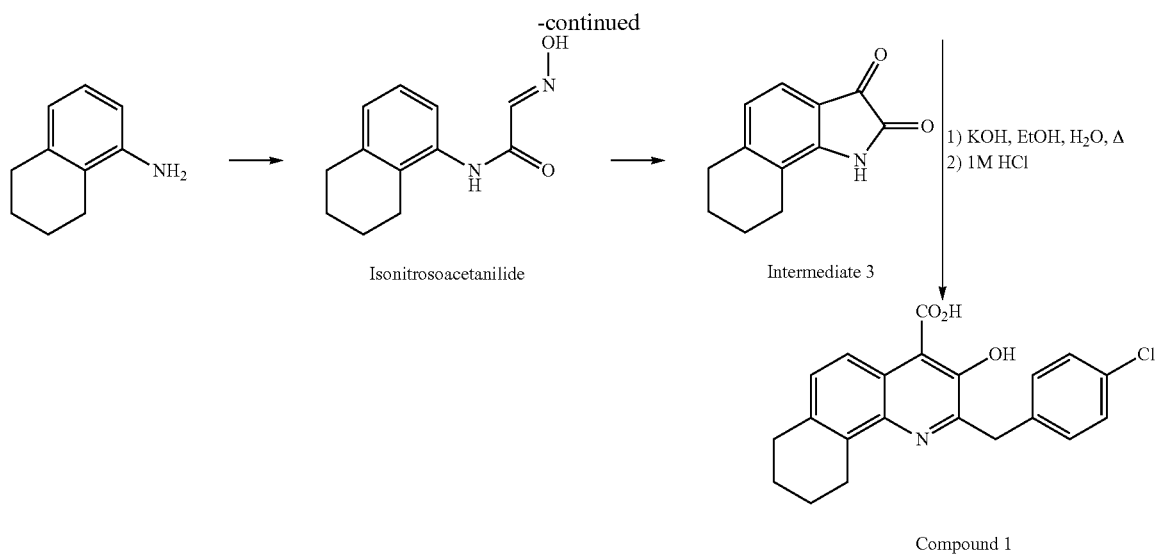

Compound 1

Example 1

Preparation of Compound 1

Intermediate 1

1-Chloro-3-(4-chloro-phenyl)-propan-2-one

A solution of 30 g (158.7 mmol) of p-chlorophenacetyl chloride in 200 ml of ether was added over 30 min to 420 ml of diazomethane in ether (0.57 mmol/ml) while stirring in an ice bath. [Diazomethane was prepared using the procedure described in Org. Syn. Coll. Vol. II pages 165-167]. The reaction was stirred in ice for 3 h, then overnight at room temperature. Next, a gentle stream of anhydrous HCl gas was passed through the solution of the diazoketone at 0-4° C. for ca. 5-8 min, till the evolution of nitrogen ceased. After an additional hour in the ice bath, the reaction was poured into 700 ml crushed ice-water. The mixture was stirred 15 min. diluted with 400 ml ether and the organic phase was washed with 750 ml of a 5% sodium carbonate solution, then 500 ml semi-saturated brine. The combined organic layers dried (sodium sulphate) ether solutions were evaporated to yield 25.5 g of crude intermediate 1 as a pale yellow solid. A solution of the crude was dissolved in 30-35 ml of methylene chloride was purified by flash chromatography on 500 g silica gel 60 (Merck 0.04-0.063 mm). Elution of the column (40×6 cm) with ethyl acetate-hexanes 20:80 gave 21.1 g (65.3% yield) of the pure intermediate 1 as colorless crystals. $^1$H NMR (CDCl$_3$, 300 MHz), δ ppm 3.88 (s, 2H) 4.11 (s, 2H) 7.16 (d, J=8.59 Hz, 2H) 7.32 (d, J=8.59 Hz, 2H).

Intermediate 2

Acetic acid 3-(4-chloro-phenyl)-2-oxo-propyl ester

To a gently refluxing solution of 21.1 g (103.9 mmol) of intermediate 1 in 200 ml ethanol was added in one portion 21.94 g (114.3 mmol, 1.1 equiv.) cesium acetate in 100 ml water and 10 ml glacial acetic acid. After refluxing for 3 h the reaction reached an optimal stage (TLC:ethyl acetate:hexanes 20:80, ammonium molybdate spray). Most of the ethanol was removed by evaporation and the resulting oily mixture was distributed between 2×800 ml portions of ethyl acetate and 2×500 ml ice cold semi saturated sodium bicarbonate solution. The organic layers were washed in sequence with 500 ml brine, dried sodium sulfate, and evaporated in vacuo. A solution of the residue in 30 ml methylene chloride was purified by flash chromatography on 500 g silica gel. Elution of the column with ethyl acetate:hexanes 20:80 to 30:70 afforded 12.09 g (51.3%) of the intermediate 2 as a colorless crystalline solid. Recrystallization from ether:hexanes provided 11.7 g of pure intermediate 2. 1.88 g of starting material was also recovered. $^1$H NMR (CDCl$_3$, 300 MHz), δ ppm 2.16 (s, 3H) 3.72 (s, 2H) 4.69 (s, 2H) 7.15 (d, J=8.59 Hz, 2H) 7.31 (d, J=8.59 Hz, 2H).

Intermediate 3

6,7,8,9-Tetrahydro-1H-benzo[g]indole-2,3-dione

The isatin synthesis described by Yang et al. (*J. Am. Chem. Soc.*, 1996, 118, 9557) was used. Chloral hydrate (3.28 g, 19.8 mmol), hydroxylamine hydrochloride (4.13 g, 59.4 mmol) and sodium sulfate (23 g, 165 mmol) were placed in a 500 mL round-bottomed flask, and 120 mL water were added. The suspension was heated to 55° C. under a N$_2$ balloon until all the solids had dissolved, and an emulsion of 5,6,7,8-Tetrahydro-naphthalen-1-ylamine (Aldrich, 2.43 g, 16.5 mmol) in 2 M aqueous hydrochloric acid was then added. Heating was continued overnight. After 18 hours, the reaction mixture was cooled to room temperature. The brown, lumpy precipitate was collected by filtration, washing with water, and dried overnight to give isoniirosoacetanilide (3.4 g). Isonitrosoacetanilide (3.4 g) was added in small portions, with stirring, to 12.4 mL concentrated sulfuric acid which had been heated to 65° C. in a round bottom flask. The isonitroso was added slowly. After all the isonitroso had been added, the purplish-black solution was allowed to stir at 85° C. for 10 minutes, and was then poured onto crushed ice in a beaker. Additional ice was added until the outside of the beaker felt cold to the touch. The orange-brown precipitate was then collected by filtration and dried overnight to yield isatin 3, which was purified by extraction. Intermediate 3 (5.7 g) was extracted with 3×400 ml hot ethyl acetate and the insoluble was discarded. Evaporation of ethyl acetate gave 3.83 g of pure material. $^1$H NMR (400 MHz, DMSO-D$_6$) δ ppm 1.74 (m, 4H) 2.50 (m, 2H) 2.74 (t, J=5.81 Hz, 2H) 6.79 (d, J=7.83 Hz, 1H) 7.23 (d, J=7.83 Hz, 1H) 10.95 (s, 1H).

2-(4-Chloro-benzyl)-3-hydroxy-7,8,9,10-tetrahydro-benzo[h]quinoline-4-carboxylic acid Compound 1

Addition of 6.8 g (33.8 mmol) of isatin 3 to 60 ml of 6N KOH at 100° C. afforded after stirring for 5 minutes a clear yellow brown solution of hydrolyzed isatin. To this was added in small portions while stirring at 100° C., a solution of 13.7 g (60.83 mmol, 1.8 equiv.) of the acetate 2 in 120 ml lukewarm ethanol over a period of 1.5 h. The clear solution was refluxed 1 h longer. After cooling to room temp., the reaction was diluted with 300 ml water under vigorous stirring then acidified by very slow addition of diluted HCl (1:4 conc. HCl:water) over 1.5 h to pH<0. The reaction was stirred overnight and filtered. The crude material was purified by column chromatography eluting with ethyl acetate:acetonitrile:methanol:water 70:5:2.5:2.5+0.5% triethylamine followed by ethyl acetate:acetonitrile:methanol:water 70:10:5:5+0.5% triethylamine. The triethyl amine salt was converted to the free acid by dissolving the salt (0.625 g) in 500 ml ethyl acetate and 220 ml water containing 20 ml dil. HCl (1:5). The organic layer was washed with brine, dried (sodium sulfate) and concentrated to a small volume when the free acid just crashed out to give canary yellow crystals of pure Compound 1 (0.512 g). Total yield was 40.8%. $^1$H NMR (400 MHz, DMSO-d$_6$) □ ppm 1.82 (m, 4H) 2.83 (t, J=5.56 Hz, 2H) 3.16 (t, J=5.68 Hz, 2H) 4.31 (s, 2H) 7.29 (d, J=8.84 Hz, 1H) 7.34 (s, 4H) 8.18 (d, J=8.84 Hz, 1H).

Example 2

Preparation of Compound 2

Intermediate 4

4-chlorophenacyl acetate

This compound was prepared as described by Cragoe et al. (*J. Org. Chem.,* 1953, 18, 561), except that the phenacyl bromide was used instead of the phenacyl chloride. A suspension of 2-bromo-4'-chloroacetophenone (Aldrich, 50 g, 0.21 mol) in 220 mL ethanol was prepared in a 1 L round-bottomed flask, and a solution of sodium acetate trihydrate (32 g, 0.24 mol) in 110 mL water and 11 mL acetic acid was added. The mixture was heated at reflux for 2.5 hours, then cooled to room temperature and refrigerated overnight. The white crystalline material which precipitated was collected by filtration, washing once with a cold solution of 50% aqueous ethanol, and dried under vacuum to give pure phenacyl acetate 4 (38 g, 83% yield): $^1$H NMR (400 MHz, CDCl$_3$) δ ppm 2.22 (s, 3H) 5.28 (s, 2H) 7.46 (d, J=8.59 Hz, 2H) 7.85 (d, J=8.59 Hz, 2H).

2-(4-chlorophenyl)-3-hydroxy-7,8,9,10-tetrahydrobenzo[h]quinoline-4-carboxylic acid Compound 2

The procedure described by Cragoe et al. (*J. Org. Chem.,* 1953, 18, 561) was followed. A suspension of 6,7-cyclohexanoisatin (intermediate 3, 15.0 g, 74.3 mmol) in 80 mL 6 M aqueous potassium hydroxide was prepared in a 1 L 3-necked round-bottomed flask fitted with a reflux condenser, and Scheme 2

Preparation of Compound 2

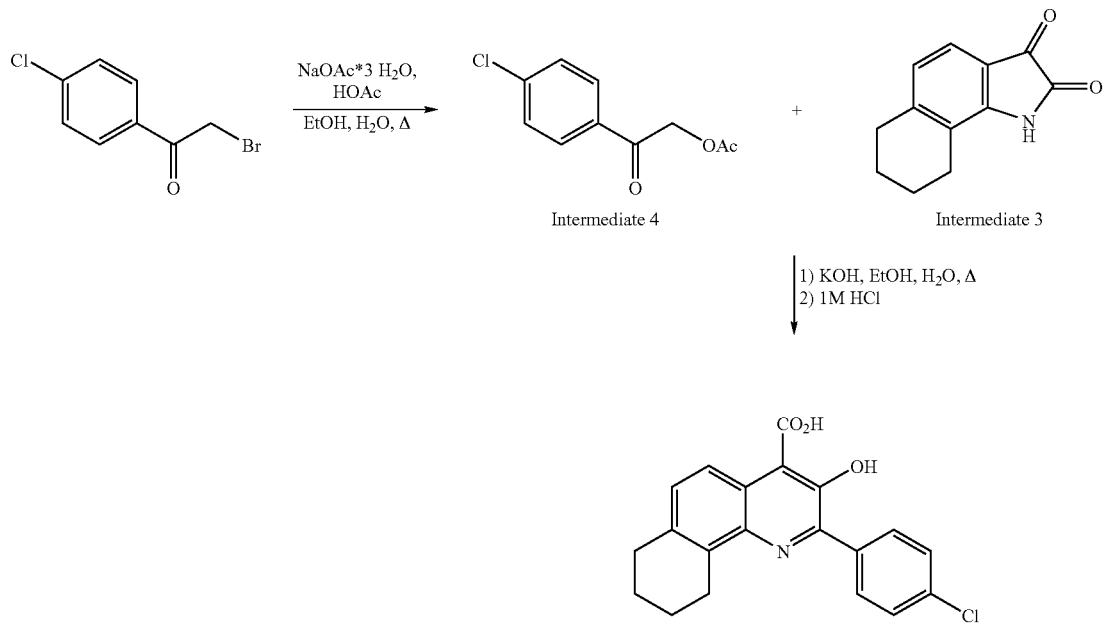

Intermediate 4

Intermediate 3

1) KOH, EtOH, H$_2$O, Δ
2) 1M HCl

Compound 2 heated to 100° C. A solution of 4-chlorophenacyl acetate (intermediate 4, 19.7 g, 92.9 mmol) in 80 mL warm ethanol was added in small portions over the course of 1 hour. After all this solution had been added, the reaction mixture was heated at reflux for an additional 4 hours. It was then cooled to room temperature, and the ethanol removed under reduced pressure. The residue was diluted with 385 mL water, chilled for 30 minutes, filtered, and acidified to pH 1 with 1 M aqueous hydrochloric acid. The crude acid precipitate was collected by filtration and dried under vacuum. To purify the acid, it was first eluted over a silica gel column (flash chromatography, 70 ethyl acetate:5 acetonitrile:2.5 methanol:2.5 water [+0.5% triethylamine]) to remove most of the highly colored impurities. The triethylammonium salt obtained was then suspended in 20% acetonitrile/water and converted back to the free acid by addition of concentrated hydrochloric acid. The acid precipitate was collected once again by filtration, dried under vacuum, and recrystallized in several batches from chloroform/ethanol to give pure Compound 2 as a pale yellow powder (3.03 g, 12% yield): $^1$H NMR (400 MHz, DMSO-D$_6$) δ ppm 1.84 (m, 4H) 2.85 (t, J=5.56 Hz, 2H) 3.25 (t, J=5.56 Hz, 2H) 7.33 (d, J=8.84 Hz, 1H) 7.58 (d, J=8.59 Hz, 2H) 8.15 (d, J=8.59 Hz, 2H) 8.26 (d, J=8.84 Hz, 1H).

Scheme 3

Preparation of Compound 3

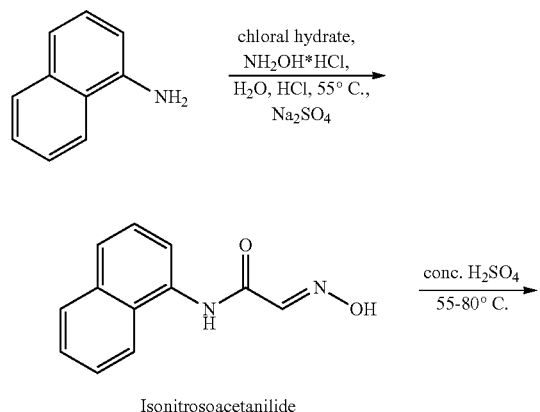

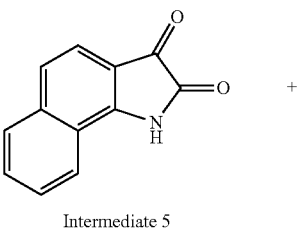

Intermediate 5

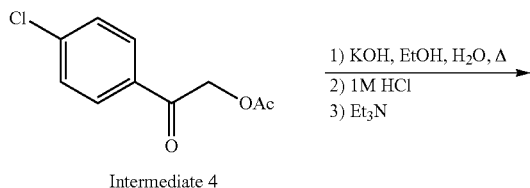

Intermediate 4

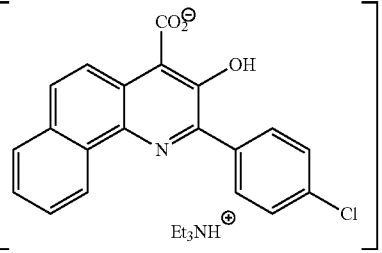

Compound 3

Example 3

Preparation of Compound 3

Intermediate 5

1H-Benzo[g]indole-2,3-dione

The procedure described above for the synthesis of intermediate 3 was followed, reacting 1-aminonaphthalene (10.0 g, 69.8 mmol) with chloral hydrate (13.9 g, 83.8 mmol) and hydroxylamine hydrochloride (17.5 g, 0.251 mol) in the presence of sodium sulfate (99 g, 0.70 mol). Isonitrosoacetanilide was obtained as a brownish-black solid (7.09 g, 47% yield).

Cyclization was also carried out as described above. After pouring the reaction mixture onto ice and chilling it in the fridge overnight, a small amount of black precipitate had appeared. This was collected by filtration, washed with water (3 x), and dried under vacuum. The filtrate was extracted into ethyl acetate as described to give more black solid. Both samples contained some of the desired isatin 5, but were very impure (2.19 g, 34% yield).

Triethylammonium 7,8-benzo-2-(4-chlorophenyl)-3-hydroxyquinoline-4-carboxylate

Compound 3

The procedure described above for the synthesis of Compound 2 was followed, reacting intermediate 5 (2.19 g, 11.1 mmol) with 4-chlorophenacyl acetate (intermediate 4, 2.95 g, 13.9 mmol). The crude acid was purified by flash chromatography over silica gel (70 ethyl acetate:5 acetonitrile:2.5 methanol:2.5 water [+0.5% triethylamine]). The product was not pure enough and therefore purified again by Discovery Analytical Chemistry (preparative HPLC, acetonitrile/water/triethylamine). After lyophilization, product Compound 3 was obtained as the triethylammonium salt, a yellow solid (54 mg, 1.1% yield): $^1$H NMR (400 MHz, DMSO-D$_6$) δ 1.17 (t, J=7.3 Hz, 9H) 3.09 (m, 6H) 7.57 (m, 3H) 7.65 (m, 1H) 7.80 (d, J=9.1 Hz, 1H) 7.89 (d, J=8.6 Hz, 1H) 8.55 (dt, J=9.1, 2.5, 2.3 Hz, 2H) 9.13 (d, J=8.8 Hz, 1H) 9.53 (d, J=9.4 Hz, 1H); HRMS (ESI+) calcd for C$_{20}$H$_{13}$ClNO$_3$ 350.0579. found 350.0580.

Scheme 4

Preparation of Compound 4

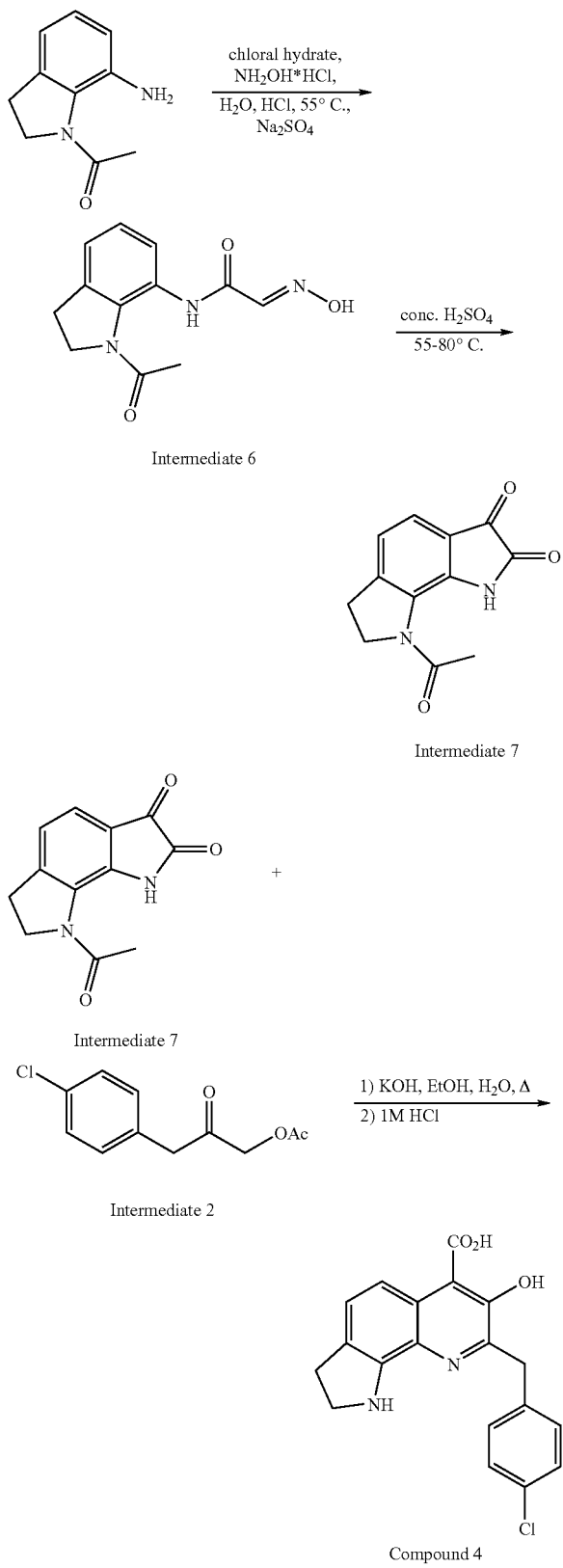

Example 4

Preparation of Compound 4

Intermediate 6

N-(1-Acetyl-2,3-dihydro-1H-indol-7-yl)-2-hydroxy-imino-acetamide

Intermediate 6 was synthesized according to the procedure described by Yang et al. (*J. Am. Chem. Soc.,* 1996, 118, 9557). Hydroxylamine hydrochloride (7.10 g, 0.102 mol) and sodium sulfate (40 g, 0.28 mol) were taken up in 200 mL water and 10 mL 2 M aqueous hydrochloric acid in a 1 L round-bottomed flask, and 1-acetyl-7-amino-2,3-dihydro-(1H)-indole (5.0 g, 28 mmol) was added. Chloral hydrate (5.63 g, 34.0 mmol) was then added, and the flask covered with a rubber septum and nitrogen balloon and heated at 55° C. overnight. After cooling to room temperature, the isonitrosoacetanilide 6 was collected by filtration and dried under vacuum to give product of sufficient purity that it could be used in the next step (5.74 g, 82% yield): $^1$H NMR (400 MHz, DMSO-D$_6$) δ 2.30 (s, 3H) 3.07 (t, J=8.0 Hz, 2H) 4.13 (t, J=7.8 Hz, 2H) 7.09 (dd, J=7.3, 1.3 Hz, 1H) 7.14 (t, 1H) 7.48 (s, 1H) 7.73 (d, J=7.8 Hz, 1H) 10.76 (s, 1H) 12.33 (s, 1H).

Intermediate 7

8-acetyl-1,6,7,8-tetrahydro-1,8-diaza-as-indacene-2,3-dione

The cyclization step was carried out as described by Marvel and Hiers (*Org. Synth. Coll. Vol. I,* 327). In a 125 mL Erlenmeyer flask, 20 mL concentrated sulfuric acid was heated to 55° C. The isonitrosoacetanilide 6 was then added in small portions, with stirring, keeping the temperature of the solution below 70° C. Upon completion of the addition, the reaction mixture was heated at 80° C. for an additional 10 minutes, then cooled to room temperature and poured onto 100 mL crushed ice. It was allowed to stand for ½ hour, and then the precipitate was collected by filtration, washing with water (3×), and dried under vacuum to give isatin 7 as a bright red, crystalline solid, of sufficient purity to be used in the next step (2.49 g, 46% yield): $^1$H NMR (400 MHz, DMSO-D$_6$) δ 2.24 (s, 3H) 3.20 (t, J=8.3 Hz, 2H) 4.15 (t, J=8.3 Hz, 2H) 7.02 (d, J=7.3 Hz, 1H) 7.32 (d, J=7.6 Hz, 1H) 10.22 (s, 1H).

8-(4-chlorobenzyl)-7-hydroxy-2,3-dihydro-1H-pyrrolo[3,2-h]quinoline-6-carboxylic acid Compound 4

This compound was synthesized by the procedure described above for Compound 1, reacting 8-acetyl-1,6,7,8-tetrahydro-1,8-diaza-as-indacene-2,3-dione (intermediate 7, 1.20 g, 5.21 mmol) with 3-(4-chlorophenyl)-2-oxopropyl acetate (intermediate 2, 1.48 g, 6.52 mmol). The crude product was purified by flash chromatography over silica gel, eluting with 70 ethyl acetate:5 acetonitrile:2.5 methanol:2.5 water (+0.5% triethylamine), and lyophilized to yield the pure triethylammonium salt. To convert the salt back to the free acid form, it was taken up in 1:1 acetonitrile/water, acidified with concentrated hydrochloric acid, and then diluted with additional water to 20% acetonitrile in water. The acid was further purified by triturating with boiling ethanol to give pure Compound 4 as a beige powder (0.249 g, 13% yield): $^1$H NMR (400 MHz, DMSO-D$_6$) δ 3.27 (t, J=8.1 Hz, 2H) 3.75 (t, J=8.1 Hz, 2H) 4.27 (s, 2H) 7.36 (m, 5H) 8.77 (s, 1H); HRMS (ESI+) calcd for $C_{19}H_{16}ClN_2O_3$ (MH+) 355.0844. found 355.0846.

chloral hydrate (10.5 g, 63.4 mmol) and hydroxylamine hydrochloride (13.2 g, 0.190 mol) in the presence of sodium sulfate (75 g, 0.53 mol). Pure product 9 was obtained as a

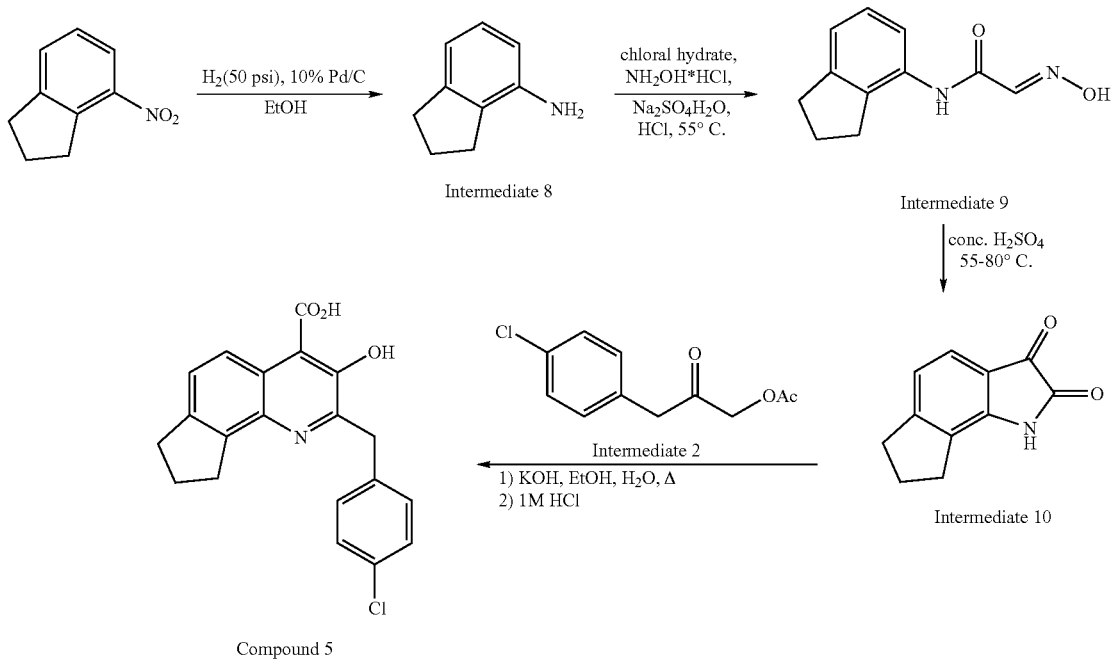

Scheme 5

Preparation of Compound 5

Example 5

Preparation of Compound 5

Intermediate 8

4-aminoindane

In a 500 mL Parr shaker vessel, 4-nitroindane (10 g, 61 mmol) was dissolved in 50 mL ethanol. A slurry of 10% Pd/C (1 g) in ethanol was added. The mixture was then placed on a Parr shaker under a hydrogen atmosphere (50 psi) for 1 hour, at which point t.l.c. (20% ethyl acetate in hexanes) showed that all the starting material had disappeared. To work up the reaction, the mixture was filtered twice through Celite, washing with a large amount of ethanol, and once through filter paper. The ethanol was evaporated under reduced pressure, and the crude product purified by flash chromatography over silica gel (10% ethyl acetate in hexanes) to give 8 as a viscous, faintly colored oil (7.04 g, 86% yield): $^1$H NMR (400 MHz, DMSO-$D_6$) δ 1.95 (m, 2H) 2.61 (t, J=7.3 Hz, 2H) 2.76 (t, J=7.5 Hz, 2H) 4.77 (s, 2H) 6.36 (d, J=7.8 Hz, 1H) 6.42 (d, J=6.8 Hz, 1H) 6.80 (t, J=7.6 Hz, 1H).

Intermediate 9

2-Hydroxyimino-N-indan-4-yl acetamide

This was synthesized according to the procedure described above for intermediate 6. The isonitrosoacetanilide was prepared by reacting 4-aminoindane 8, (7.04 g, 52.9 mmol) with brown solid (7.18 g, 66% yield): $^1$H NMR (400 MHz, DMSO-$D_6$) δ 2.00 (m, 2H) 2.80 (t, J=7.3 Hz, 2H) 2.88 (t, J=7.6 Hz, 2H) 7.05 (d, J=6.8 Hz, 1H) 7.12 (t, J=7.6 Hz, 1H) 7.45 (d, J=7.8 Hz, 1H) 7.71 (s, 1H) 9.49 (s, 1H) 12.19 (s, 1H).

Intermediate 10

1,6,7,8-tetrahydro-1-aza-as-indacene-2,3-dione

The cyclization step was also carried out as described for intermediate 7. However, after pouring the cooled reaction mixture onto ice, only a very small amount of precipitate appeared, even after chilling the mixture overnight. Thus, this black precipitate was filtered out and thrown away (<200 mg was isolated in this fashion), and the filtrate extracted into ethyl acetate (3×). The ethyl acetate solution was washed with brine, dried over anhydrous magnesium sulfate, filtered, and evaporated under reduced pressure to yield pure isatin 10 as a bright orange powder (0.36 g, 5.5% yield): $^1$H NMR (400 MHz, DMSO-$D_6$) δ 2.07 (m, 2H) 2.76 (t, J=7.5 Hz, 2H) 2.88 (t, J=7.5 Hz, 2H) 6.95 (d, J=7.6 Hz, 1H) 7.30 (d, J=7.6 Hz, 1H) 11.10 (s, 1H).

8-(4-chlorobenzyl)-7-hydroxy-2,3-dihydro-1H-9-aza-cyclopenta[a]naphthalene-6-carboxylic acid Compound 5

This compound was synthesized by the procedure described above for Compound 1, reacting 1,6,7,8-tetrahydro-1-aza-as-indacene-2,3-dione 10 (0.36 g, 1.92 mmol) with 3-(4-chlorophenyl)-2-oxopropyl acetate 2 (0.54 g, 2.40 mmol). The crude acid was purified as described above for Compound 4 to give pure product Compound 5 as a bright yellow powder (94 mg, 14% yield): $^1$H NMR (400 MHz, DMSO-D$_6$) δ 2.15 (quint., 2H) 3.05 (t, J=7.3 Hz, 2H) 3.28 (t, J=7.5 Hz, 2H) 4.32 (s, 2H) 7.33 (s, 4H) 7.49 (d, J=8.3 Hz, 1H) 8.36 (d, J=8.1 Hz, 1H); HRMS (ESI+) calcd for C$_{20}$H$_{17}$ClNO$_3$ (MH+) 354.0892. found 354.0898.

Scheme 6

Preparation of Compound 6

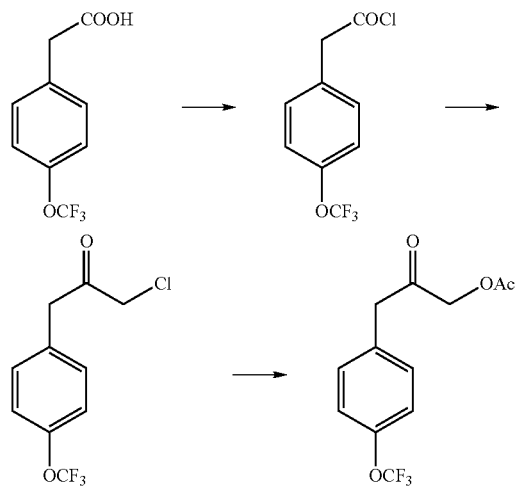

Intermediate 11                    Intermediate 12

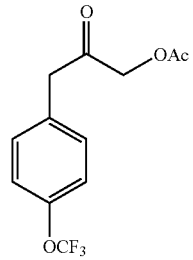

Intermediate 12

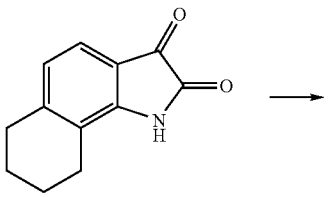

Intermediate 3

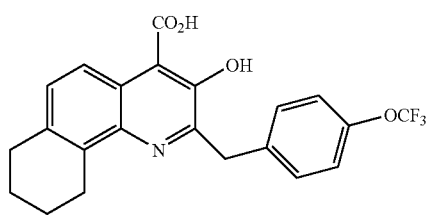

Compound 6

Example 6

Preparation of Compound 6

Intermediate 11

1-Chloro-3-(4-trifluoromethoxy phenyl)propan-2-one

A solution of 14.58 g (66.23 mMol) of 4-trifluoromethoxy phenyl acetic acid in 75 mL thionyl chloride was refluxed 1.5 hours, cooled, and the excess reagent was evaporated in vacuo. The resulting crude acid chloride was re-evaporated twice from dry toluene and used as such in the following step. To 175 mL diazomethane in Et$_2$O (ca. 0.57 mMol/mL) in an ice bath was added over 30 minutes a solution of the crude acid chloride in 85 mL Et$_2$O. The reaction was stirred 2 hours in the cold, then overnight at room temperature. Through the cooled (0° C.) solution was passed a gentle stream of Cl$_2$ gas for 5 minutes. After one more hour in the ice bath the reaction was diluted with 500 mL Et$_2$O, poured into 350 mL crushed ice-water, and the layers were separated. The aqueous layer was extracted with a second portion of Et$_2$O. The organic phases were washed with 5% NAHCO$_3$ (2×200 mL) and semi-saturated brine (400 mL), combined, dried (Na$_2$SO$_4$), and evaporated in vacuo. The residue was dissolved in 30 mL CH$_2$Cl$_2$, and the solution purified by flash chromatography on silica gel 60 (Merck) using AcOEt-cyclohexane 20:80 and 30:70 as the eluent. Pooling and evaporation of the appropriate fractions gave 6.97 g (44.1% overall) of the intermediate 11 as a colorless oil. $^1$H NMR (400 MHz, CDCl$_3$) δ ppm 3.85 (s, 2H) 4.12 (s, 2H) 7.18 (m, J=21.98 Hz, 4H).

Intermediate 12

Acetic acid 2-oxo-3-(4-trifluoromethoxyphenyl) propyl ester

To a stirred, gently refluxing solution of the chloride 11 (6.80 g, 26.92 mMol) in 50 mL EtOH was added in one portion 5.68 g 29.6 mMol, 1.1 equiv.) CsOAc dissolved in 25 mL water and 2.5 mL glacial AcOH, and the reaction was refluxed 3 hours longer. Most of the EtOH was evaporated in vacuo, the concentrate was diluted with 100 mL water and the mixture extracted with AcOEt (2×400 mL). The organic phases were washed in sequence with ice cold, semi saturated NaHCO$_3$ (300 mL) and semi saturated brine (300 mL), combined, dried (Na$_2$SO$_4$), and evaporated in vacuo. The residue was crystallized from Et2O and excess hexanes to afford 3.15 g of 12 (42.4%) of the acetate as colorless flakes. (More product present in the mother liquors). $^1$H NMR (400 MHz, CDCl$_3$) δ2.16 (s, 3H) 3.75 (s, 2H) 4.71 (s, 2H) 7.23 (m, 4H).

3-Hydroxy-2-(4-trifluoromethoxybenzyl)-7,8,9,10-tetrahydrobenzo[h]quinoline-4-carboxylic acid Compound 6

To 1.00 g (4.97 mMol) intermediate 3 dissolved in 9 mL 6N KOH at 100-2° C. was added over one hour in several portions under stirring a solution of 2.26 g (8.18 mMol, 1.65 equiv.) acetate 12 in 18 mL lukewarm EtOH. At the end of the addition the solution was stirred one hour longer under gentle reflux, cooled, slowly diluted with 150 mL water, then acidified with 35 mL 2.5N HCl, added dropwise over 1.5 hours. The gummy precipitate was separated from the clear supernatant (pH<0) by decantation after standing 2 hours. The gum was dissolved in 600 mL AcOEt, the resulting solution was washed with 200 mL semi saturated brine, dried (Na2SO4), and evaporated in vacuo. Separation of the quinoline salicylate from unreacted cyclohexylisatin (27% recovery) and a variety of other impurities could only be achieved by gravity chromatography on silica gel 60 (Merck) of the triethylammonium salt, using a gradient of AcOEt-MeCN-MeOH—H$_2$O 70:5:2.5:2.5 to 70:10:5:5, containing 0.5% NEt$_3$. Pooling of the appropriate fractions afforded pure product as the partial NEt$_3$ salt. The salt was the converted to the free acid by treatment with 1N HCl (aqueous) in a diluted AcOEt solution, which was quickly washed with semi saturated brine, dried, and evaporated in vacuo. Crystallization of the residue by slurring with a small volume of AcOEt-MeCN-MeOH—H$_2$O 70:10:5:5 (no NEt$_3$) afforded 566 mg (27.3%) of the canary yellow quinoline salicilate as the free acid Compound 6. $^1$H NMR (400 MHz, DMSO-D$_6$) δ1.81 (m, 4H) 2.83 (t, J=5.56 Hz, 2H) 3.13 (T, J=5.56 Hz, 2H) 4.35 (s, 2H) 7.28 (t, J=7.71 Hz, 3H) 7.45 (d, J=8.34 Hz, 2H) 8.21 (d, J=8.84 Hz, 1H).

and the mixture heated at 80° C. until the t.l.c. of a hydrolyzed aliquot (5% ethyl acetate in hexanes, visualized by cerium molybdate staining) showed that the starting material had been consumed. The reaction vessel was placed in a water bath to cool it, and Pd(PPh$_3$)$_4$ (0.118 g, 0.102 mmol) was added, followed by dropwise addition, via syringe, of chloroacetyl chloride (0.61 mL, 0.87 g, 7.7 mmol). The brown suspension was allowed to stir overnight at room temperature. To work up the reaction, 12 mL 1 M HCl was added, and the mixture extracted into ethyl acetate (4×12 mL). The combined organic layers were washed with brine, dried over anhydrous MgSO$_4$, filtered, and evaporated. The crude product was purified by flash chromatography over silica gel (1-30% ethyl acetate in hexanes), to give material of sufficient purity to be used in the next step (0.545 g, 45% yield): $^1$H NMR (400 MHz, CDCl$_3$) δ 3.89 (s, 2H) 4.13 (s, 2H) 7.06 (dd, J=8.2, 2.6 Hz, 1H) 7.33 (d, J=2.0 Hz, 1H) 7.42 (d, J=8.3 Hz, 1H).

Scheme 7: Preparation of Compound 7

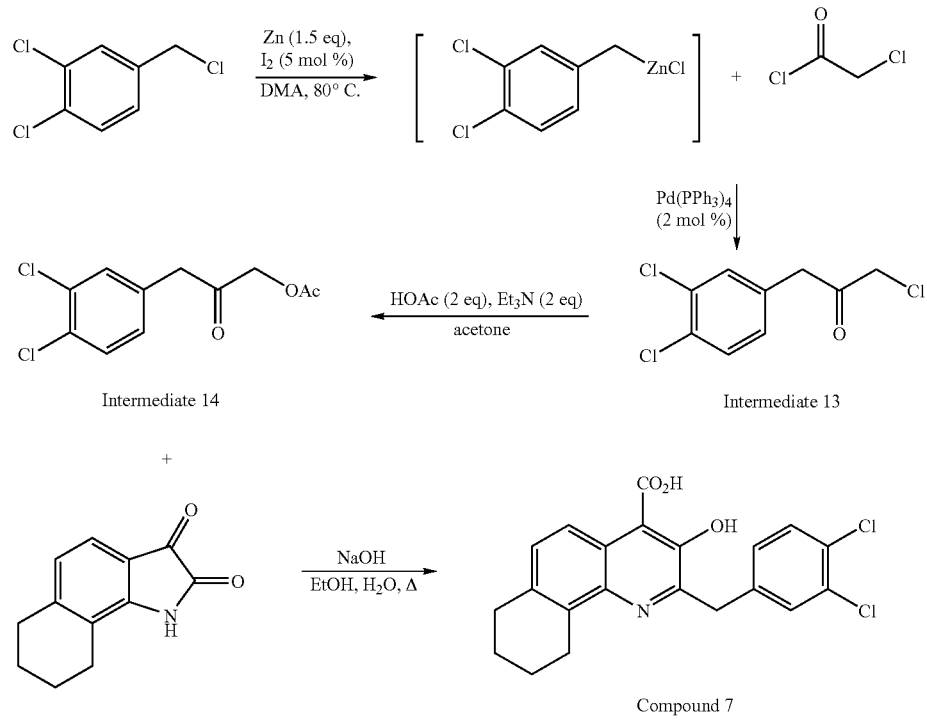

Example 7

Preparation of Compound 7

Intermediate 13

1-Chloro-3-(3,4-dichlorophenyl)propan-2-one

The organozinc species was generated as described by S. Huo (*Organic Letters* 2003, 5 (4), 423-5). In a flame-dried 25 mL 2-necked round-bottomed flask, under an inert atmosphere, iodine (65 mg, 0.26 mmol) was taken up in 6 mL anhydrous N,N-dimethylacetamide. Zinc dust (0.502 g, 7.67 mmol) was added, and the suspension stirred until the red color of the iodine disappeared. Then, 3,4-dichlorobenzyl chloride (0.71 mL, 1.0 g, 5.1 mmol) was added via syringe, Intermediate 14

3-(3,4-Dichlorophenyl)-2-oxopropyl acetate

In a round-bottomed flask, 1-chloro-3-(3,4-dichlorophenyl)propan-2-one (0.545 g, 2.30 mmol) was taken up in 2 mL acetone, and acetic acid (0.26 mL, 0.28 g, 4.6 mmol) was added. The solution was cooled in an ice water bath, and triethylamine (0.64 mL, 0.47 g, 4.6 mmol) added dropwise via syringe over 30 minutes. The reaction mixture was then stirred overnight. Precipitated triethylammonium chloride was removed by filtration, and the filtrate was evaporated, taken up in 10 mL ethyl acetate, washed twice with brine, dried over anhydrous MgSO$_4$, filtered, and evaporated. The crude product was purified by flash chromatography over silica gel (10-30% ethyl acetate in hexanes) to give a pure product (0.200 g, 33% yield): $^1$H NMR (400 MHz, CDCl$_3$) δ 2.17 (s, 3H) 3.71 (s, 2H) 4.71 (s, 2H) 7.05 (dd, J=8.2, 2.2 Hz, 1H) 7.32 (d, J=2.0 Hz, 1H) 7.41 (d, J=8.1 Hz, 1H).

2-(3,4-Dichlorobenzyl)-3-hydroxy-7,8,9,10-tetrahydrobenzo[h]quinoline-4-carboxylic acid Compound 7

The Pfitzinger reaction was used. In a 2-necked 25 mL round-bottomed flask, 6,7,8,9-tetrahydrobenzo[g]indoline-2,3-dione (0.119 g, 0.590 mmol) was taken up in 1 mL ethanol and 3 mL 10 M NaOH, and the mixture heated to reflux temperature. A solution of 3-(3,4-dichlorophenyl)-2-oxopropyl acetate (0.200 g, 0.767 mmol) in 3 mL ethanol was added in small portions over the course of 1 hour, by syringe. Refluxing was continued for an additional hour after the addition was complete, and the reaction mixture was then cooled to room temperature and acidified with glacial acetic acid, and the yellow precipitate collected by filtration. This crude product was purified by preparative HPLC (acetonitrile/water/triethylamine), and the pure salt thus obtained was converted back to the free acid by acidification of a 5% acetonitrile in water solution with concentrated HCl. The bright yellow precipitate was collected by filtration and dried under vacuum (47.8 mg, 20% yield): $^1$H NMR (400 MHz, DMSO-d$_6$) δ 1.73-1.86 (m, 4H) 2.81 (t, J=6.1 Hz, 2H) 3.12 (t, J=5.9 Hz, 2H) 4.30 (s, 2H) 7.28 (t, J=8.7 Hz, 2H) 7.53 (d, J=8.1 Hz, 1H) 7.59 (d, J=2.0 Hz, 1H) 8.19 (d, J=8.6 Hz, 1H), HRMS (ESI+) calcd for C$_{21}$H$_{18}$Cl$_2$NO$_3$ (MH+) 402.0658. found 402.0661.

dropwise, with stirring, from an addition funnel to a 1 L Erlenmeyer flask containing 85 mL of an ethereal diazomethane solution, cooled in an ice water bath. Upon completion of the addition (which was done over 30 minutes), the solution was allowed to stir overnight, gradually warming to room temperature. It was then cooled in an ice water bath once again, and a gentle stream of dry HCl gas was passed through, until nitrogen evolution ceased. The mixture was stirred for 1 hour, then poured into 150 mL ice water, stirred for 20 minutes, and extracted twice into 180 mL portions of ether. The combined ether extracts were washed with 5% Na$_2$CO$_3$ (150 mL) and brine (120 mL), then dried over anhydrous MgSO$_4$, filtered, and evaporated. Purification by flash chromatography over silica gel (5% ethyl acetate in hexanes) gave a clear, yellow oil, which turned into a black solid upon standing overnight, unless it was stored in the freezer, under nitrogen (2.33 g, 43% yield): $^1$H NMR (400 MHz, CDCl$_3$) δ 4.11 (s, 2H) 4.17 (s, 2H) 6.93-6.96 (m, 1H) 7.00 (dd, J=5.2, 3.4 Hz, 1H) 7.24-7.28 (m, 1H).

Intermediate 16

3-(Thiophen-2-yl)-2-oxopropyl acetate

The procedure described above for the synthesis of 3-(3,4-dichlorophenyl)-2-oxopropyl acetate was followed, reacting 1-chloro-3-(thiophen-2-yl)propan-2-one (1.00 g, 5.73 mmol) with acetic acid (0.66 mL, 0.69 g, 12 mmol) and triethylamine (1.60 mL, 1.16 g, 11.5 mmol). Purification by flash chromatography over silica gel (10-40% ethyl acetate in hexanes) gave an orange oil (0.144 g, 13% yield): $^1$H NMR (400 MHz,

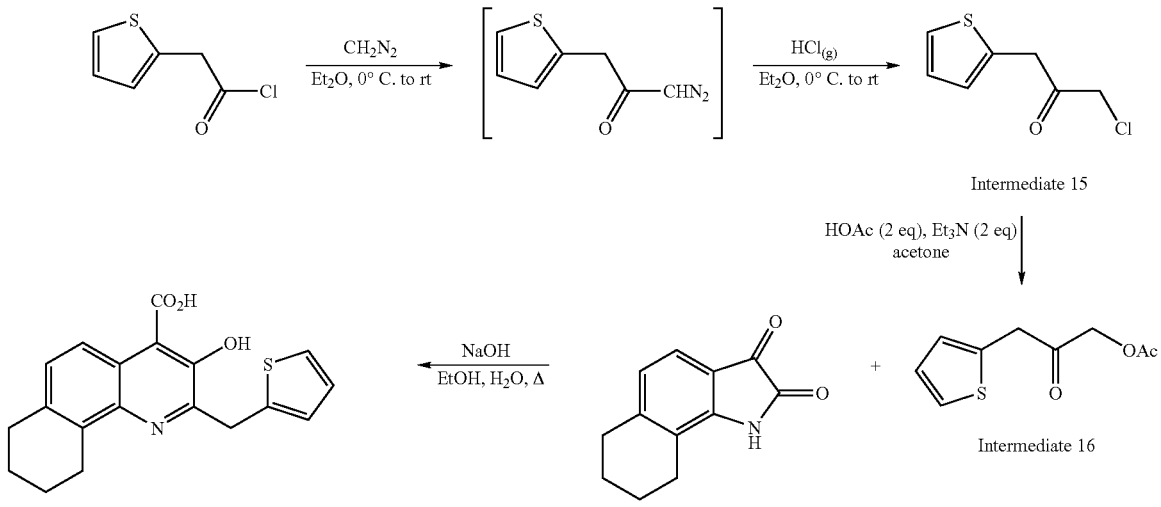

Compound 8

Example 8

Preparation of Compound 8

Intermediate 15

1-Chloro-3-(thiophen-2-yl)propan-2-one

The chloride was synthesized by Arndt-Eistert homologation of the acid chloride. A solution of 2-thiopheneacetyl chloride (3.8 mL, 5.0 g, 31 mmol) in 60 mL ether was added CDCl$_3$) δ 2.17 (s, 3H) 3.95 (s, 2H) 4.74 (s, 2H) 6.92-6.94 (m, 1H) 6.99 (dd, J=5.2, 3.4 Hz, 1H) 7.25 (dd, J=5.1, 1.3 Hz, 1H).

3-Hydroxy-2-(thiophen-2-ylmethyl)-7,8,9,10-tetrahydrobenzo[h]quinoline-4-carboxylic acid Compound 8

The procedure described above for the synthesis and purification of example 7 was followed, reacting 6,7,8,9-tetrahydrobenzo[g]indoline-2,3-dione (0.112 g, 0.557 mmol) with 3-(thiophen-2-yl)-2-oxopropyl acetate (0.144 g, 0.724 mmol). Product was obtained as a dark yellow powder (9.1 mg, 4.8% yield): $^1$H NMR (400 MHz, DMSO-$d_6$) δ 1.75-1.88 (m, 4H) 2.83 (t, J=5.7 Hz, 2H) 3.17-3.25 (m, 2H) 4.49 (s, 2H) 6.89-6.94 (m, 1H) 6.94-6.98 (m, 1H) 7.27 (d, J=9.1 Hz, 1H) 7.32 (dd, J=5.3, 1.3 Hz, 1H) 8.18 (d, J=8.8 Hz, 1H); HRMS (ESI+) calcd for $C_{19}H_{18}NO_3S$ (MH+) 340.1002. found 340.1011.

Intermediate 18

3-(Benzo[b]thiophen-3-yl)-2-oxopropyl acetate

The procedure described above for the synthesis of 3-(3,4-dichlorophenyl)-2-oxopropyl acetate was followed, reacting 1-(benzo[b]thiophen-3-yl)-3-chloropropan-2-one (0.661 g, 2.94 mmol) with acetic acid (0.34 mL, 0.35 g, 5.9 mmol) and

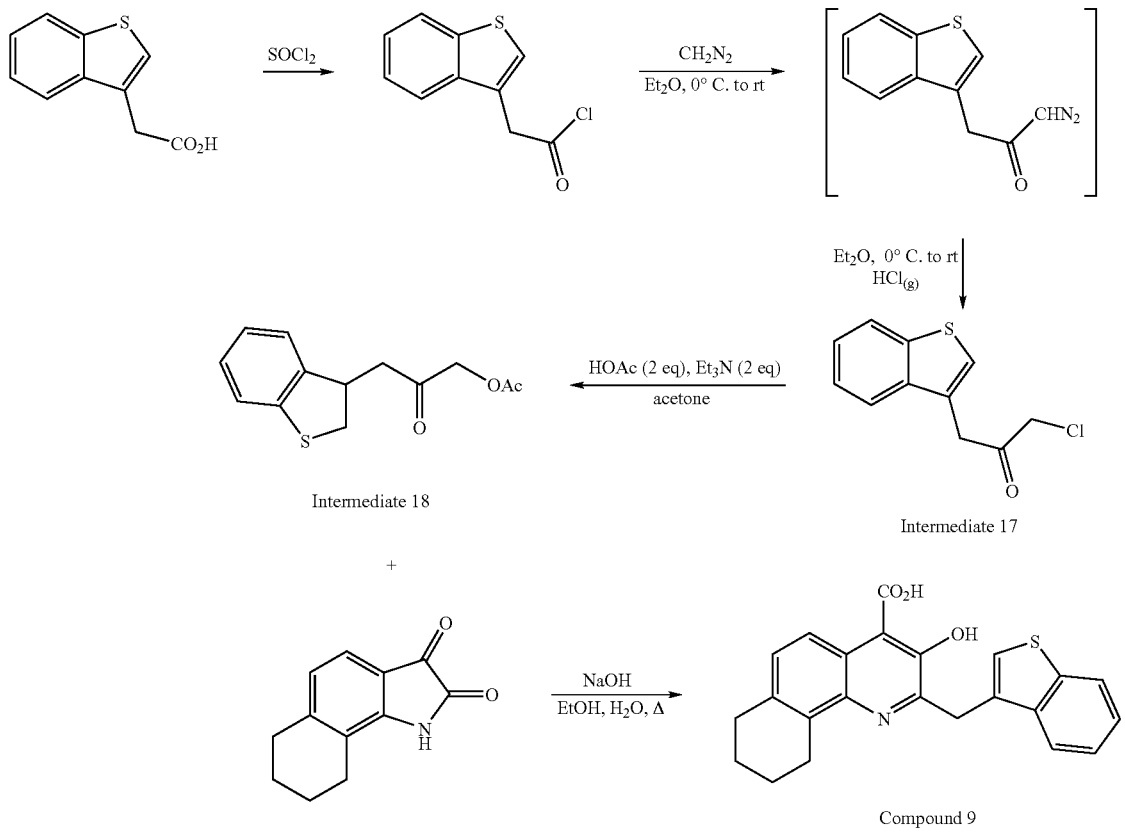

Example 9

Preparation of Compound 9

Intermediate 17

1-(Benzo[b]thiophen-3-yl)-3-chloropropan-2-one

The procedure described above for the synthesis of 1-chloro-3-(thiophen-2-yl)propan-2-one was followed. To prepare the acid chloride, 2-(benzo[b]thiophen-3-yl)acetic acid (1.00 g, 5.20 mmol) was added to 6 mL thionyl chloride in a 25 mL round-bottomed flask. The mixture was stirred overnight at room temperature, and the thionyl chloride then removed in vacuo and the residue azeotroped twice with toluene. The acid chloride was then reacted with diazomethane and HCl. The crude product was purified by flash chromatography over silica gel (2-30% ethyl acetate in hexanes) to give pure material (0.661 g, 56% yield): $^1$H NMR (400 MHz, CDCl$_3$) δ 4.12 (s, 2H) 4.14 (d, J=1.0 Hz, 2H) 7.36-7.44 (m, 3H) 7.67-7.71 (m, 1H) 7.87-7.90 (m, 1H).

triethylamine (0.82 mL, 0.59 g, 5.9 mmol). Flash chromatography over silica gel (10-40% ethyl acetate in hexanes) gave pure product (0.372 g, 51% yield): $^1$H NMR (400 MHz, CDCl$_3$) δ 2.14 (s, 3H) 3.98 (s, 2H) 4.71 (s, 2H) 7.34-7.44 (m, 3H) 7.67-7.70 (m, 1H) 7.86-7.89 (m, 1H).

2-(Benzo[b]thiophen-3-ylmethyl)-3-hydroxy-7,8,9,10-tetrahydrobenzo[h]quinoline-4-carboxylic acid Compound 9

The procedure described above for the synthesis and purification of example 7 was followed, reacting 6,7,8,9-tetrahydrobenzo[g]indoline-2,3-dione (0.232 g, 1.15 mmol) with 3-(benzo[b]thiophen-3-yl)-2-oxopropyl acetate (0.372 g, 1.50 mmol). Product was obtained as a bright yellow powder (30.6 mg, 6.8% yield): $^1$H NMR (400 MHz, DMSO-$d_6$) δ 1.71-1.85 (m, 4H) 2.80 (t, J=5.2 Hz, 2H) 3.11 (t, J=5.1 Hz, 2H) 4.53 (s, 2H) 7.25 (d, J=8.8 Hz, 1H) 7.30-7.45 (m, 3H) 7.94 (d, J=7.8 Hz, 1H) 8.11 (d, J=8.1 Hz, 1H) 8.19 (d, J=8.6 Hz, 1H); HRMS (ESI+) calcd for $C_{23}H_{20}NO_3S$ (MH+) 390.1159. found 390.1167.

Scheme 10 - Preparation of Compound 10

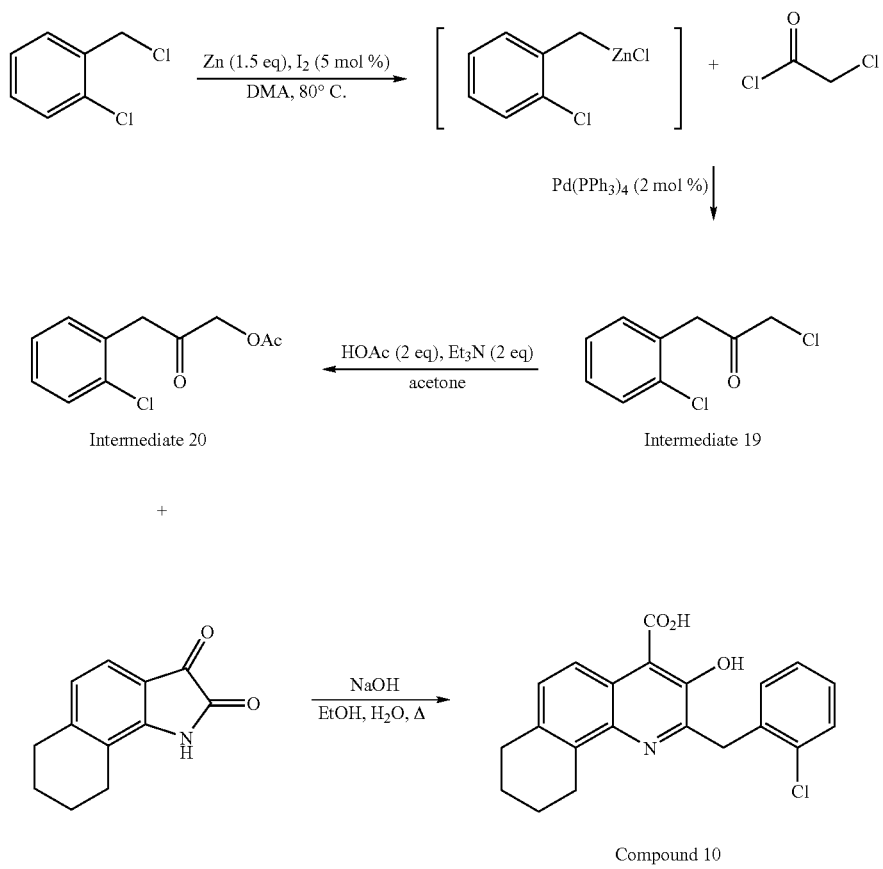

Example 10

Preparation of Compound 10

Intermediate 19

1-Chloro-3-(2-chlorophenyl)propan-2-one

The procedure described above for the synthesis of 1-chloro-3-(3,4-dichlorophenyl)propan-2-one was followed, reacting 2-chlorobenzyl chloride (1.6 mL, 2.0 g, 12 mmol) with zinc dust (1.22 g, 18.6 mmol) in the presence of iodine (0.157 g, 0.620 mmol), then with chloroacetyl chloride (1.5 mL, 2.1 g, 19 mmol) in the presence of Pd(PPh$_3$)$_4$ (0.287 g, 0.248 mmol). Flash chromatography over silica gel (10% ethyl acetate in hexanes) gave product of sufficient purity to be used in the next step (0.556 g, 22% yield): $^1$H NMR (400 MHz, CDCl$_3$) δ 4.03 (s, 2H) 4.19 (s, 2H) 7.19-7.29 (m, 3H) 7.38-7.42 (m, 1H).

Intermediate 20

3-(2-Chlorophenyl)-2-oxopropyl acetate

The procedure described above for the synthesis of 3-(3,4-dichlorophenyl)-2-oxopropyl acetate was followed, reacting 1-chloro-3-(2-chlorophenyl)propan-2-one (0.556 g, 2.74 mmol) with acetic acid (0.31 mL, 0.33 g, 5.5 mmol) and triethylamine (0.76 mL, 0.56 g, 5.5 mmol). Flash chromatography over silica gel (5-40% ethyl acetate in hexanes) gave pure product (0.251 g, 43% yield): $^1$H NMR (400 MHz, CDCl$_3$) δ 2.17 (s, 3H) 3.88 (s, 2H) 4.75 (s, 2H) 7.24-7.27 (m, 3H) 7.38-7.42 (m, 1H).

2-(2-Chlorobenzyl)-3-hydroxy-7,8,9,10-tetrahydrobenzo[h]quinoline-4-carboxylic acid

Compound 10

The procedure described above for the synthesis and purification of example 7 was followed, reacting 6,7,8,9-tetrahydrobenzo[g]indoline-2,3-dione (0.183 g, 0.908 mmol) with 3-(2-chlorophenyl)-2-oxopropyl acetate (0.251 g, 1.18 mmol). Product was obtained as a bright yellow powder (79.5 mg, 24% yield): $^1$H NMR (400 MHz, DMSO-d$_6$) δ 1.74 (br. s, 4H) 2.80 (br. s, 2H) 2.92 (br. s, 2H) 4.42 (s, 2H) 7.22-7.32 (m, 4H) 7.43-7.50 (m, 1H) 8.23 (d, J=8.8 Hz, 1H); HRMS (ESI+) calcd for C$_{21}$H$_{19}$ClNO$_3$ (MH+) 368.1048. found 368.1047.

Scheme 11 - Preparation of Compound 11

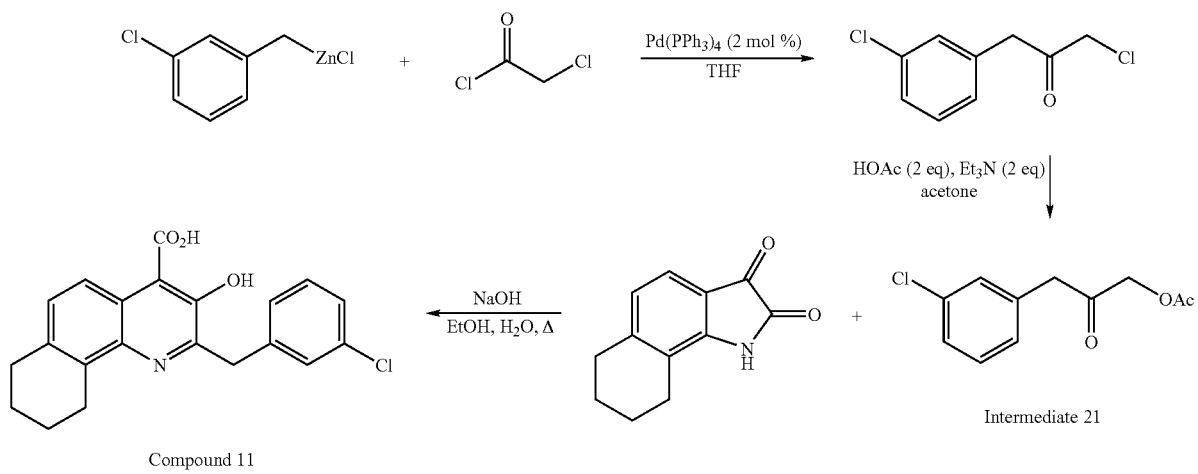

Example 11

Preparation of Compound 11

Intermediate 21

3-(3-Chlorophenyl)-2-oxopropyl acetate

A flame-dried 50 mL round-bottomed flask, under an inert atmosphere, was charged with Pd(PPh$_3$)$_4$ (0.30 g, 0.26 mmol). Anhydrous THF (7 mL) was added, then a 0.5 M THF solution of 3-chlorobenzylzinc chloride (26 mL, 13 mmol). The flask was cooled in an ice bath, and chloroacetyl chloride was added via syringe, over 1 hour. The solution went from a very dark brown (almost black), to a clear, light yellow. The mixture was stirred overnight at room temperature, then quenched by addition of 5 g ice, stirred for an additional hour, diluted with ethyl acetate, washed twice with brine, dried over anhydrous MgSO$_4$, filtered, and evaporated.

This crude material was reacted with acetic acid (1.42 mL, 1.49 g, 24.8 mmol) and triethylamine (3.46 mL, 2.51 g, 24.8 mmol), as described above for the synthesis 10 of 3-(3,4-dichlorophenyl)propan-2-one. Flash chromatography over silica gel (20% ethyl acetate in hexanes) gave pure product (1.22 g, 46% yield): $^1$H NMR (400 MHz, CDCl$_3$) δ 2.16 (s, 3H) 3.72 (s, 2H) 4.69-4.71 (m, 2H) 7.08-7.11 (m, 1H) 7.21-7.23 (m, 1H) 7.26-7.29 (m, 2H).

2-(3-Chlorobenzyl)-3-hydroxy-7,8,9,10-tetrahydrobenzo[h]quinoline-4-carboxylic acid

Compound 11

The procedure described above for the synthesis and purification of example 7 was followed, reacting 6,7,8,9-tetrahydrobenzo[g]indoline-2,3-dione (0.495 g, 2.46 mmol) with 3-(3-chlorophenyl)-2-oxopropyl acetate (0.680 g, 3.20 mmol). Product was obtained as a bright yellow powder (186 mg, 20% yield): $^1$H NMR (400 MHz, DMSO-d$_6$) δ 1.74-1.88 (m, 4H) 2.83 (t, J=4.3 Hz, 2H) 3.15 (t, J=4.6 Hz, 2H) 4.32 (s, 2H) 7.24-7.35 (m, 4H) 7.39 (s, 1H) 8.20 (d, J=8.8 Hz, 1H); HRMS (ESI+) calcd for C$_{21}$H$_{19}$ClNO$_3$ (MH+) 368.1048. found 368.1046.

Scheme 12 - Preparation of Compound 12

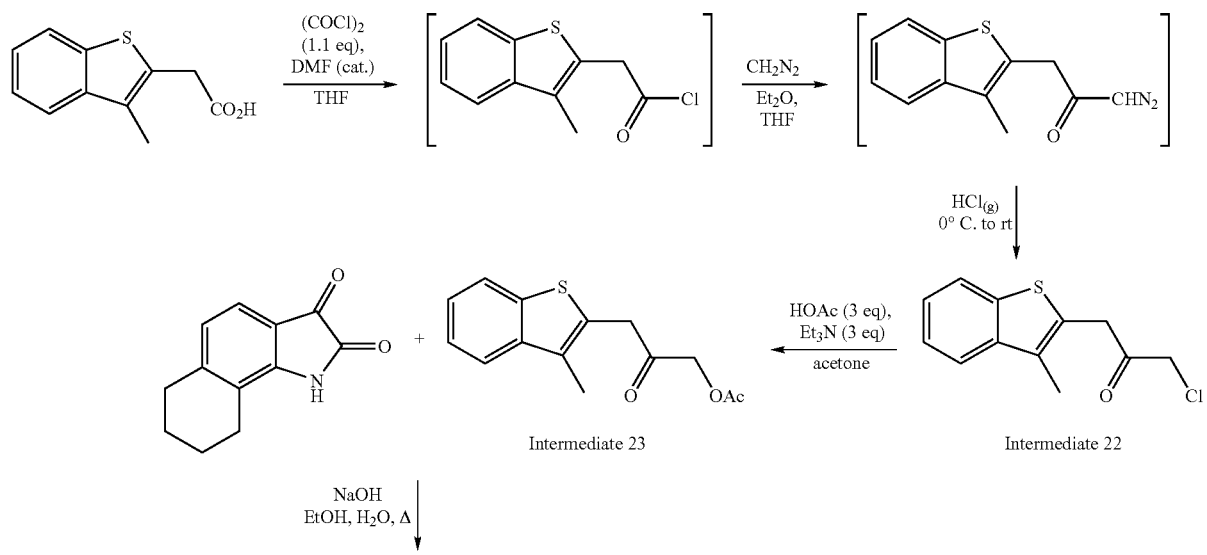

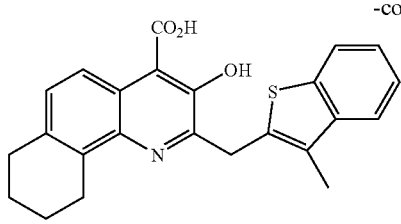

Compound 12

Example 12

Preparation of Compound 12

Intermediate 22

1-Chloro-3-[2-(3-methylbenzo[b]thiophen-2-yl)propan-2-one

The procedure described above for the synthesis of 1-(benzo[b]thiophen-3-yl)-3-chloropropan-2-one was followed, except that in this case the acid chloride was generated by dropwise addition of oxalyl chloride (1.2 mL, 1.7 g, 13 mmol) to a cold THF solution (18 mL) of 2-(3-methylbenzo[b]thiophen-2-yl)acetic acid (2.5 g, 12 mmol), containing catalytic DMF. After the addition was complete, the solution was allowed to stir at room temperature for 1 hour, then added to an ethereal diazomethane solution, as previously described. Work-up and purification by flash chromatography over silica gel (10% ethyl acetate in hexanes) gave product of sufficient purity to be used in the next step: $^1$H NMR (400 MHz, CDCl$_3$) δ 2.35 (s, 3H) 4.13 (s, 2H) 4.17 (s, 2H) 7.30-7.42 (m, 2H) 7.67 (d, J=7.6 Hz, 1H) 779 (d, J=7.8 Hz, 1H).

Intermediate 23

3-[2-(3-Methylbenzo[b]thiophen-2-yl)]-2-oxopropyl acetate

The procedure described above for the synthesis of 3-(3,4-dichlorophenyl)-2-oxopropyl acetate was followed, reacting 1-chloro-3-[2-(3-methylbenzo[b]thiophen-2-yl)propan-2-one (0.754 g, 3.16 mmol) with acetic acid (0.54 mL, 0.57 g, 9.5 mmol) and triethylamine (1.3 mL, 0.96 g, 9.5 mmol). Flash chromatography over silica gel (16-36% ethyl acetate in hexanes) gave pure product (0.109 g, 13% yield): $^1$H NMR (400 MHz, CDCl$_3$) δ 2.17 (s, 3H) 2.35 (s, 3H) 3.97 (s, 2H) 4.73 (s, 2H) 7.31-7.41 (m, 2H) 7.64-7.68 (m, 1H) 7.76-7.80 (m, 1H).

3-Hydroxy-2-[2-(3-methylbenzo[b]thiophen-2-ylmethyl)]-7,8,9,10-tetrahydrobenzo[h]quinoline-4-carboxylic acid

Compound 12

The procedure described above for the synthesis of WAY-278932 was followed, reacting 6,7,8,9-tetrahydrobenzo[g]indoline-2,3-dione (64 mg, 0.318 mmol) with 3-[2-(3-methylbenzo[b]thiophen-2-yl)]-2-oxopropyl acetate (0.109 g, 0.414 mmol). Preparative HPLC purification (water/acetonitrile/triethylamine), followed by lyophilization gave product as a fluffy, light yellow solid (186 mg, 20% yield): $^1$H NMR (400 MHz, DMSO-d$_6$) δ 1.76-1.88 (m, 4H) 2.50 (s, 3H) 2.80 (t, J=5.3 Hz, 2H) 3.20 (t, J=5.8 Hz, 2H) 4.52 (s, 2H) 7.16 (d, J=8.8 Hz, 1H) 7.25 (t, J=7.6 Hz, 1H) 7.33 (t, J=7.6 Hz, 1H) 7.68 (d, J=7.8 Hz, 1H) 7.79 (d, J=8.1 Hz, 1H) 8.68 (s, 1H); HRMS (ESI+) calcd for C$_{24}$H$_{22}$NO$_3$S (MH+) 404.1315. found 404.1312.

Scheme 13 - Preparation of Compound 13

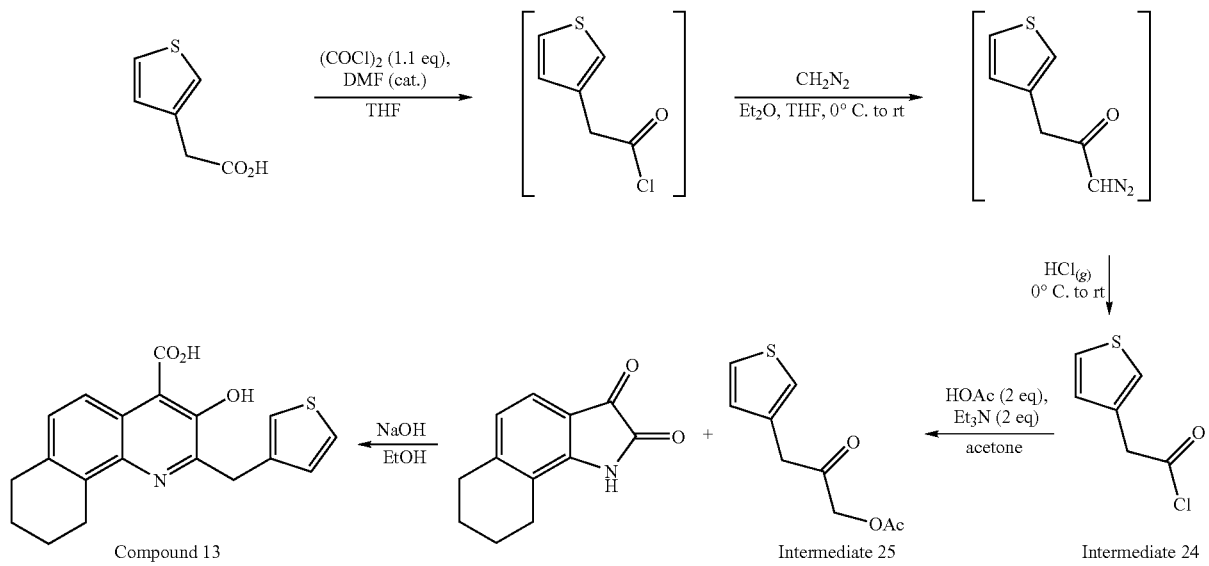

Example 13

Preparation of Compound 13

Intermediate 24

1-Chloro-3-(thiophen-3-yl)propan-2-one

The procedure described above for the synthesis of 1-chloro-3-[2-(3-methylbenzo[b]thiophen-2-yl)propan-2-one was followed, reacting thiophene-3-acetic acid (5.32 g, 37.4 mmol) with oxalyl chloride (3.6 mL, 5.2 g, 41 mmol, then ethereal diazomethane, then dry HCl gas. Work-up gave pure product, a brown oil which solidified upon refrigeration to a golden-brown, waxy solid (6.52 g, 100% yield): $^1$H NMR (400 MHz, CDCl$_3$) δ 3.94 (s, 2H) 4.13 (s, 2H) 6.99 (d, J=5.1 Hz, 1H) 7.16 (dd, J=1.5, 0.8 Hz, 1H) 7.33 (dd, J=4.9, 2.9 Hz, 1H).

Intermediate 25

2-Oxo-3-(thiophen-3-yl)propyl acetate

The procedure described above for the synthesis of 3-(3,4-dichlorophenyl)-2-oxopropyl acetate was followed, reacting 1-chloro-3-(thiophen-3-yl)propan-2-one (6.53 g, 37.4 mmol) with acetic acid (4.3 mL, 4.5 g, 75 mmol) and triethylamine (10.4 mL, 7.57 g, 74.8 mmol). Flash chromatography over silica gel (20% ethyl acetate in hexanes) gave pure product, a golden-yellow oil (3.85 g, 52% yield): $^1$H NMR (400 MHz, CDCl$_3$) δ 2.16 (s, 3H) 3.77 (s, 2H) 4.70 (s, 2H) 6.98 (dd, J=4.8, 1.3 Hz, 1H) 7.14 (dd, J=1.8, 1.0 Hz, 1H) 7.32 (dd, J=4.9, 2.9 Hz, 1H).

3-Hydroxy-2-(thiophen-3-ylmethyl)-7,8,9,10-tetrahydrobenzo[h]quinoline-4-carboxylic acid

Compound 13

The procedure described above for the synthesis and purification of example 7 was followed, reacting 6,7,8,9-tetrahydrobenzo[g]indoline-2,3-dione (0.500 g, 2.48 mmol) with 2-oxo-3-(thiophen-3-yl)propyl acetate (0.640 g, 3.23 mmol). Product was obtained as a bright yellow powder (187 mg, 22% yield): $^1$H NMR (400 MHz, DMSO-d$_6$) δ 1.73-1.89 (m, 4H) 2.83 (t, J=4.9 Hz, 2H) 3.18 (t, J=5.7 Hz, 2H) 4.32 (s, 2H) 7.10 (d, J=4.8 Hz, 1H) 7.23 (s, 1H) 7.27 (d, J=8.8 Hz, 1H) 7.40-7.47 (m, 1H) 8.22 (d, J=8.6 Hz, 1H); HRMS (ESI+) calcd for C$_{19}$H$_{18}$NO$_3$S (MH+) 340.1002. found 340.1006. Anal. Calcd for C$_{19}$H$_7$NO$_3$S.2H$_2$O: C, 60.78; H, 5.64; N, 3.73. Found: C, 63.01; H, 5.60; N, 3.76.

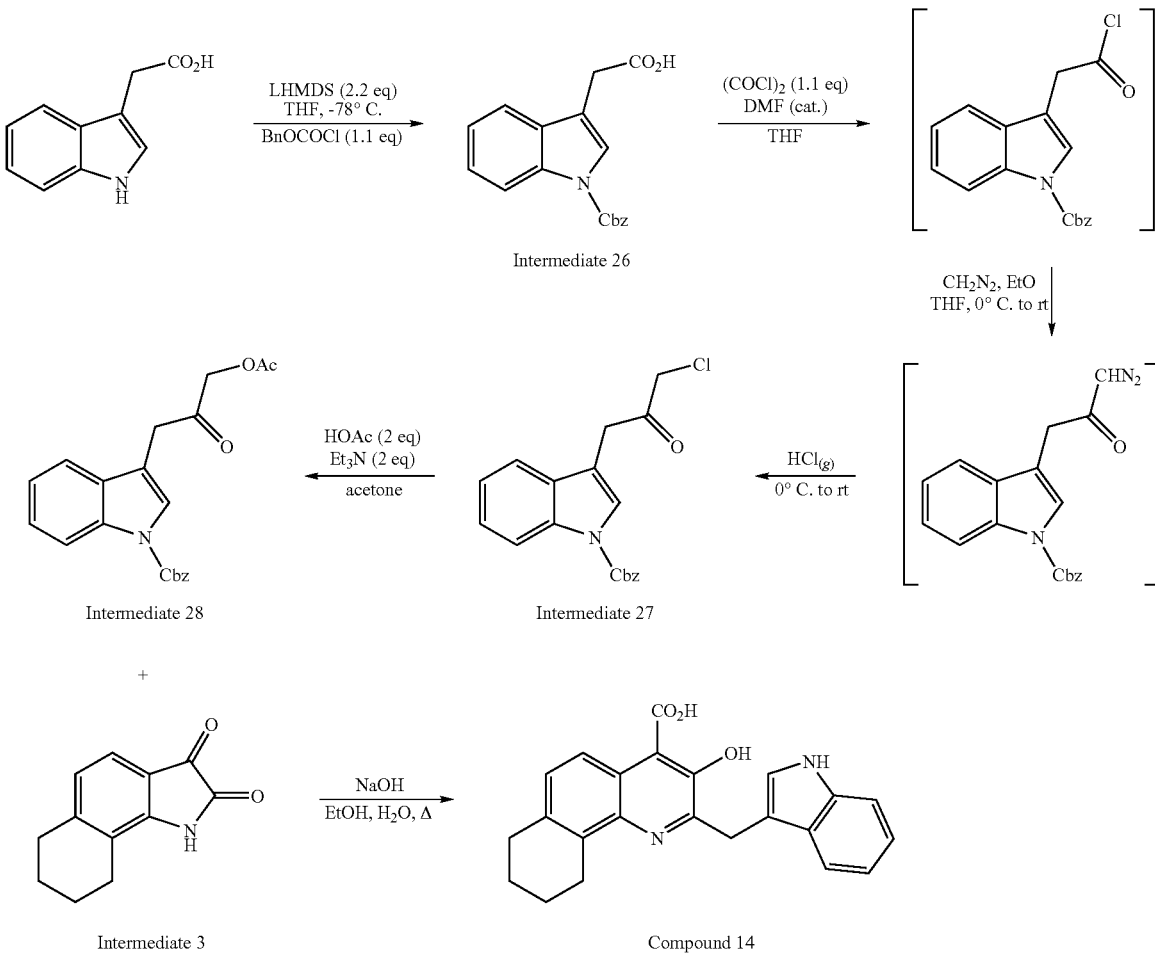

Scheme 14 - Preparation of Compound 14

Example 14

Preparation of Compound 14

Intermediate 26

1-(Benzyloxycarbonyl)indol-3-yl acetic acid

Indole-3-acetic acid (13 g, 74 mmol) was taken up in 130 mL anhydrous THF in a flame-dried, 2-necked 1 L round-bottomed flask, under an inert atmosphere, and cooled to −78° C. (dry ice/acetone bath). A 1.0 M THF solution of LHMDS (163 mL, 0.163 mol) was added via syringe over 30 minutes, and the reaction mixture allowed to stir for an additional 30 minutes at −78° C. once the addition was complete. Next, benzyl chloroformate (11.7 mL, 13.9 g, 81.6 mmol) was added dropwise via syringe. Stirring was then continued for 1 hour. To work up the reaction mixture, it was quenched with 2 M HCl, and partitioned between 2 M HCl and ethyl acetate. The aqueous layer was extracted with additional ethyl acetate, and the combined organic layers washed with brine, dried over anhydrous MgSO$_4$, filtered, and evaporated to give a white solid with a pinkish tinge (22.49 g, 98% yield): $^1$H NMR (400 MHz, DMSO-d$_6$) δ 3.71 (s, 2H) 5.47 (s, 2H) 7.27 (t, J=7.2 Hz, 1H) 7.32-7.47 (m, 4H) 7.54 (d, J=6.8 Hz, 2H) 7.58 (d, J=7.6 Hz, 1H) 7.68 (s, 1H) 8.08 (d, J=8.1 Hz, 1H) 12.43 (s, 1H); HRMS (ESI+) calcd for C$_{18}$H$_{16}$NO$_4$ (MH+) 310.1074. found 310.1080.

Intermediate 27

3-[1-(Benzyloxycarbonyl)indol-3-yl]-1-chloropropan-2-one

The procedure described above for the synthesis of 1-chloro-3-[2-(3-methylbenzo[b]thiophen-2-yl)propan-2-one was followed, reacting 1-(benzyloxycarbonyl)indol-3-yl acetic acid (22.49 g, 72.7 mmol) with oxalyl chloride (7.0 mL, 10 g, 80 mmol, then ethereal diazomethane, then dry HCl gas. Flash chromatography over silica gel (15-20% ethyl acetate in hexanes) gave pure product (21.64 g, 87% yield): $^1$H NMR (400 MHz, CDCl$_3$) δ 3.97 (d, J=1.0 Hz, 2H) 4.15 (s, 2H) 5.45 (s, 2H) 7.27-7.30 (m, 1H) 7.33-7.51 (m, 7H) 7.63 (s, 1H) 8.19 (br. s, 1H); HRMS (ESI+) calcd for C$_{19}$H$_{17}$ClNO$_3$ (MH+) 342.0892. found 342.0900.

Intermediate 28

3-[1-(Benzyloxycarbonyl)indol-3-yl]-2-oxopropyl acetate

The procedure described above for the synthesis of 3-(3,4-dichlorophenyl)-2-oxopropyl acetate was followed, reacting 3-[1-(benzyloxycarbonyl)indol-3-yl]-1-chloropropan-2-one (19.28 g, 56.4 mmol) with acetic acid (6.5 mL, 6.8 g, 0.11 mol) and triethylamine (15.7 mL, 11.4 g, 0.113 mol). Flash chromatography over silica gel (25% ethyl acetate in hexanes) gave pure product as an orange oil that solidified under vacuum to a yellow solid (9.06 g, 44% yield): $^1$H NMR (400 MHz, CDCl$_3$) δ 2.15 (s, 3H) 3.81 (d, J=0.8 Hz, 2H) 4.73 (s, 2H) 5.45 (s, 2H) 7.26-7.30 (m, 1H) 7.32-7.51 (m, 7H) 7.62 (s, 1H) 8.18 (s, 1H).

3-Hydroxy-2-(indol-3-ylmethyl)-7,8,9,10-tetrahydrobenzo[h]quinoline-4-carboxylic acid

Compound 14

The procedure described above for the synthesis and purification of example 7 was followed, reacting 6,7,8,9-tetrahydrobenzo[g]indoline-2,3-dione (0.294 g, 1.46 mmol) with 3-[1-(benzyloxycarbonyl)indol-3-yl]-2-oxopropyl acetate (0.693 g, 1.90 mmol). Product was obtained as a brownish-orange powder (93 mg, 17% yield): $^1$H NMR (400 MHz, DMSO-d$_6$) δ 1.65-1.93 (m, 4H) 2.83 (br. s, 2H) 3.24 (br. s, 2H) 4.41 (s, 2H) 6.90-7.08 (m, 2H) 7.13-7.36 (m, 3H) 7.75 (d, J=7.1 Hz, 1H) 8.19 (s, 1H) 10.84 (s, 1H); HRMS (ESI+) calcd for C$_{23}$H$_{21}$N$_2$O$_3$ (MH+) 373.1547. found 373.1548. Anal. Calcd for C$_{23}$H$_{20}$N$_2$O$_3$.H$_2$O: C, 70.75; H, 5.68; N, 7.17. Found: C, 71.04; H, 5.64; N, 7.01.

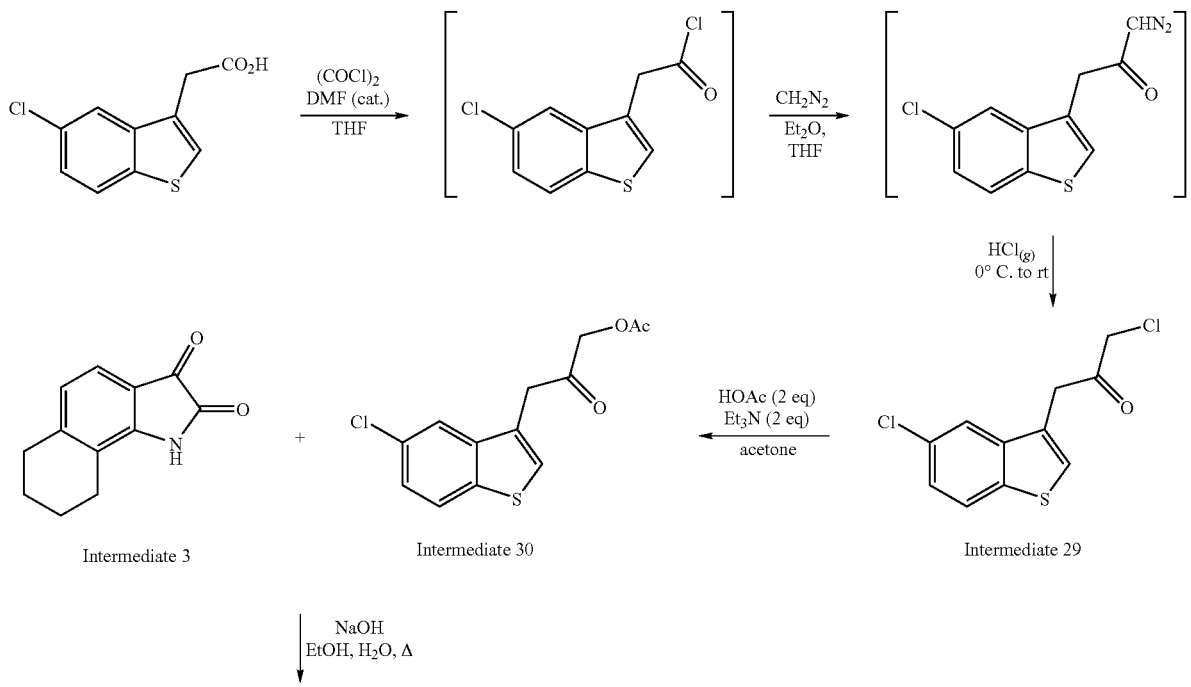

Scheme 15 - Preparation of Compound 15

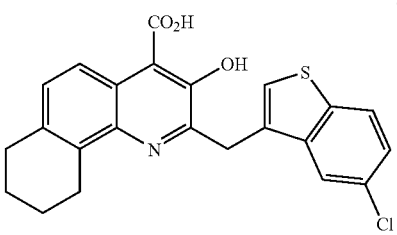

Compound 15

Example 15

Preparation of Compound 15

Intermediate 29

1-Chloro-3-(5-chlorobenzo[b]thiophen-3-yl)-propan-2-one

The procedure described above for the synthesis of 1-chloro-3-[2-(3-methylbenzo[b]thiophen-2-yl)propan-2-one was followed, reacting 5-chlorobenzo[b]thiophen-3-yl acetic acid (4.00 g, 17.6 mmol) with oxalyl chloride (1.7 mL, 2.5 g, 19 mmol), then ethereal diazomethane, then dry HCl gas. Work-up of the reaction mixture gave pure product as a light golden-yellow solid (4.43 g, 97% yield): $^1$H NMR (400 MHz, CDCl$_3$) δ 4.12 (s, 2H) 4.15 (s, 2H) 7.35 (dd, J=8.6, 2.1 Hz, 1H) 7.43 (s, 1H) 7.65 (d, J=2.1 Hz, 1H) 7.79 (d, J=8.6 Hz, 1H).

Intermediate 30

3-(5-Chlorobenzo[b]thiophen-3-yl)-2-oxopropyl acetate

The procedure described above for the synthesis of 3-(3,4-dichlorophenyl)-2-oxopropyl acetate was followed, reacting 1-chloro-3-(5-chlorobenzo[b]thiophen-3-yl)-propan-2-one (4.43 g, 17.1 mmol) with acetic acid (2.0 mL, 2.1 g, 35 mmol) and triethylamine (4.9 mL, 3.6 g, 35 mmol). Flash chromatography over silica gel (20% ethyl acetate in hexanes) gave pure product, a pale yellow solid (2.76 g, 57% yield): $^1$H NMR (400 MHz, CDCl$_3$) δ 2.16 (s, 3H) 3.94 (d, J=1.0 Hz, 2H) 4.73 (s, 2H) 7.34 (ddd, J=8.6, 2.0, 0.5 Hz, 1H) 7.39-7.42 (m, 1H) 7.65 (d, J=2.0 Hz, 1H) 7.78 (dd, J=8.6, 0.5 Hz, 1H).

2-(5-Chlorobenzo[b]thiophen-3-ylmethyl)-3-hydroxy-7,8,9,10-tetrahydrobenzo[h]quinoline-4-carboxylic acid Compound 15

The procedure described above for the synthesis and purification of compound 7 was followed, reacting 6,7,8,9-tetrahydrobenzo[g]indoline-2,3-dione (0.200 g, 0.994 mmol) with 3-(5-chlorobenzo[b]thiophen-3-yl)-2-oxopropyl acetate (0.365 g, 1.29 mmol). It was not possible to convert the triethylammonium salt obtained by preparative HPLC (basic modifier) back to the free acid by the usual method. Thus, the final product, a sunflower-yellow powder, was a triethylammonium salt with 6:5 acid:base stoichiometry (108 mg, 21% yield): $^1$H NMR (400 MHz, DMSO-d$_6$) δ 1.17 (t, J=7.2 Hz, 7.5H) 1.72-1.87 (m, 4H) 2.77 (t, J=5.9 Hz, 2H) 3.10 (dq, 5H) 3.18 (t, J=5.7 Hz, 2H) 4.46 (s, 2H) 7.08 (d, J=8.8 Hz, 1H) 7.35 (dd, J=8.7, 2.2 Hz, 1H) 7.59 (s, 1H) 7.96 (d, J=8.3 Hz, 1H) 8.41 (d, J=2.1 Hz, 1H) 8.94 (d, J=8.8 Hz, 1H); HRMS (ESI+) calcd for C$_{23}$H$_{19}$ClNO$_3$S (MH+) 424.0769. found 424.0770. Anal. Calcd for [C$_{23}$H$_{19}$ClNO$_3$S]$_6$[C$_6$H$_{15}$N]$_5$[H$_2$O]: C, 65.60; H, 5.78; N, 4.72. Found: C, 64.75; H, 6.01; N, 4.56.

Scheme 16 - Preparation of Compound 16

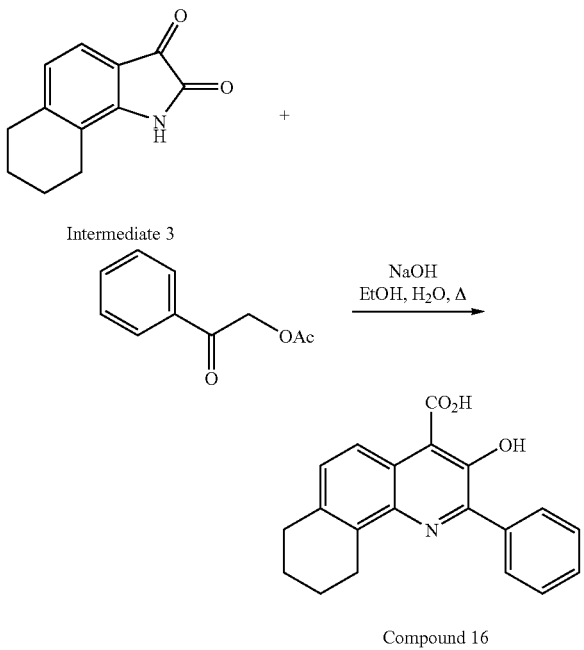

Compound 16

Example 16

Preparation of Compound 16

3-hydroxy-2-phenyl-7,8,9,10-tetrahydro-benzo[h]quinoline-4-carboxylic acid

Compound 16

The procedure described above for the synthesis and purification of example 7 was followed, reacting 6,7,8,9-tetrahydrobenzo[g]indoline-2,3-dione (0.294 g, 1.46 mmol) with phenacyl acetate (0.338 g, 1.90 mmol). Product was obtained as a yellow powder (116 mg, 25% yield): $^1$H NMR (400 MHz, DMSO-D6) δ ppm 1.75-1.93 (m, 4H) 2.86 (t, J=5.68 Hz, 2H) 3.25 (t, J=5.81 Hz, 2H) 7.33 (d, J=9.09 Hz, 1H) 7.44-7.56 (m, 3H) 8.09 (dd, J=8.08, 1.52 Hz, 2H) 8.28 (d, J=8.84 Hz, 1H).

Scheme 17 - Preparation of Compound 17

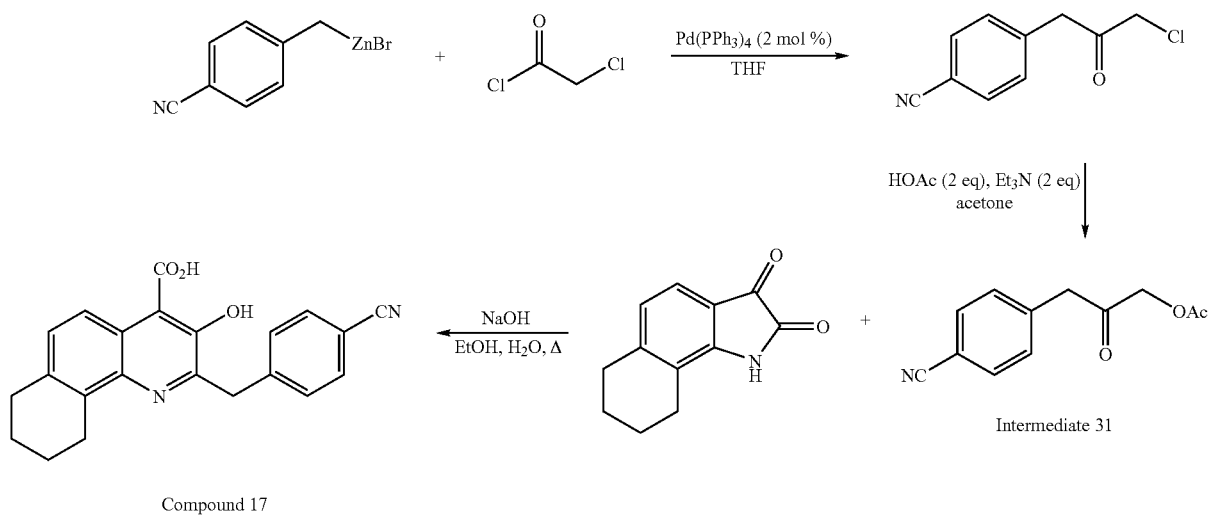

Example 17

Preparation of Compound 17

Intermediate 31

Acetic acid 3-(4-cyano-phenyl)-2-oxo-propyl ester

The procedure described above for the synthesis of 3-(3-Chlorophenyl)-2-oxopropyl acetate was followed, reacting 0.5 M THF solution of 4-cyanobenzylzinc bromide (26 mL, 13 mmol), Pd(PPh$_3$)$_4$ (0.30 g, 0.26 mmol) with chloroacetyl chloride (26 mL, 13 mmol). Work-up of the reaction mixture gave crude product as a yellow oil.

This crude material was reacted with acetic acid (1.42 mL, 1.49 g, 24.8 mmol) and triethylamine (3.46 mL, 2.51 g, 24.8 mmol), as described above for the synthesis of 3-(3,4-dichlorophenyl)propan-2-one. Flash chromatography over silica gel (10-30% ethyl acetate in hexanes) gave pure product (0.71 g, 25% yield). $^1$H NMR (400 MHz, DMSO-D6) δ ppm 2.09 (s, 3H) 3.96 (s, 2H) 4.88 (s, 2H) 7.40 (d, J=8.34 Hz, 2H) 7.79 (d, J=8.59 Hz, 2H)

2-(4-Cyano-benzyl)-3-hydroxy-7,8,9,10-tetrahydro-benzo[h]quinoline-4-carboxylic acid Compound 17

In a 25 mL round-bottomed flask, 6,7,8,9-tetrahydrobenzo[g]indoline-2,3-dione (0.119 g, 0.590 mmol) was taken up in 1 mL ethanol and 3 mL 10 M NaOH, and the mixture heated at reflux temperature for 3 minutes. A solution of acetic acid 3-(4-cyano-phenyl)-2-oxo-propyl ester (0.167 g, 0.767 mmol) in 3 mL ethanol was then added and the reaction further heated for 10 minutes. The reaction mixture was then cooled to room temperature and acidified with glacial acetic acid, and the yellow precipitate collected by filtration. The procedure described above for the purification of example 7 was followed. Product was obtained as a bright yellow powder (42 mg, 20% yield): $^1$H NMR (400 MHz, DMSO-D6) δ ppm 1.74-1.87 (m, 4H) 2.83 (t, J=5.31 Hz, 2H) 3.12 (t, J=5.43 Hz, 2H), 4.40 (s, 2H), 7.28 (d, J=9.09 Hz, 1H) 7.51 (d, J=8.59 Hz, 2H) 7.75 (d, J=8.34 Hz, 2H) 8.23 (d, J=8.84 Hz, 1H).

Scheme 18 - Preparation of Compound 18 and 19

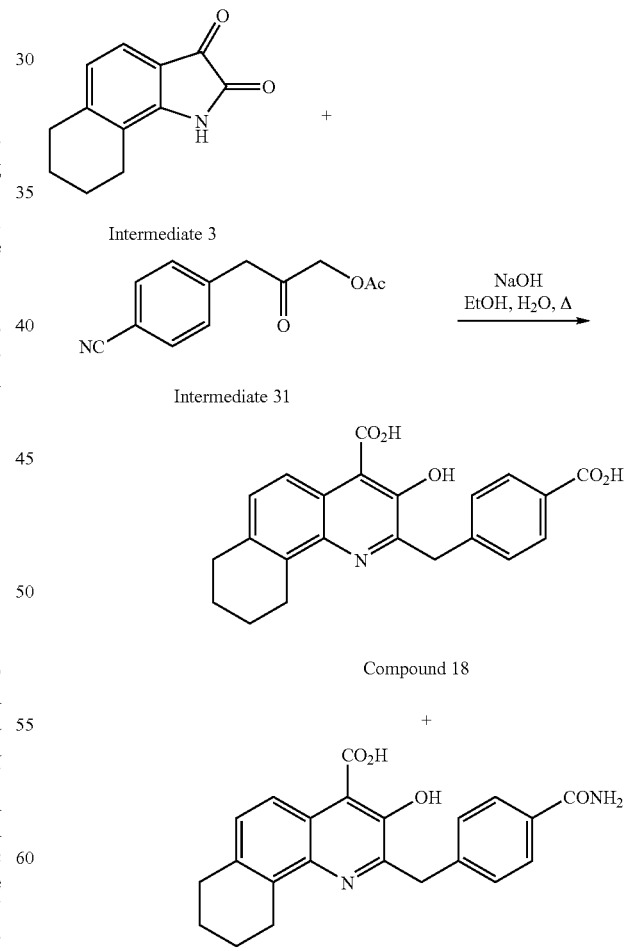

Examples 18 and 19

Preparation of Compound 18 and 19

2-(4-Carboxy-benzyl)-3-hydroxy-7,8,9,10-tetrahydro-benzo[h]quinoline-4-carboxylic acid (Compound 18) and 2-(4-Carbamoyl-benzyl)-3-hydroxy-7,8,9,10-tetrahydro-benzo[h]quinoline-4-carboxylic acid (Compound 19)

The procedure described above for the synthesis and purification of example 7 was followed, reacting 6,7,8,9-tetrahydrobenzo[g]indoline-2,3-dione (0.495 g, 2.46 mmol) with acetic acid 3-(4-cyano-phenyl)-2-oxo-propyl ester (0.694 g, 3.20 mmol). Two products were isolated as bright yellow powders. Compound 18 was obtained in 15% yield (139 mg): $^1$H NMR (400 MHz, DMSO-D6) δ ppm 1.76-1.88 (m, 4H) 2.84 (t, J=6.69 Hz, 2H) 3.16 (t, J=6.32 Hz, 2H) 4.39 (s, 2H) 7.30 (d, J=8.84 Hz, 1H) 7.42 (d, J=8.59 Hz, 2H) 7.77 (d, J=8.34 Hz, 2H) 8.43 (d, J=8.84 Hz, 1H). Compound 19 was obtained in 10% yield (92 mg): $^1$H NMR (400 MHz, DMSO-D6) δ ppm 1.77-1.89 (m, 4H) 2.84 (t, J=6.44 Hz, 2H) 3.16 (t, J=5.81 Hz, 2H) 4.39 (s, 2H) 7.30 (d, J=8.84 Hz, 1H) 7.42 (d, J=8.59 Hz, 2H) 7.77 (d, J=8.34 Hz, 2H) 8.43 (d, J=8.84 Hz, 1H).

Scheme 19 - Preparation of Compound 20

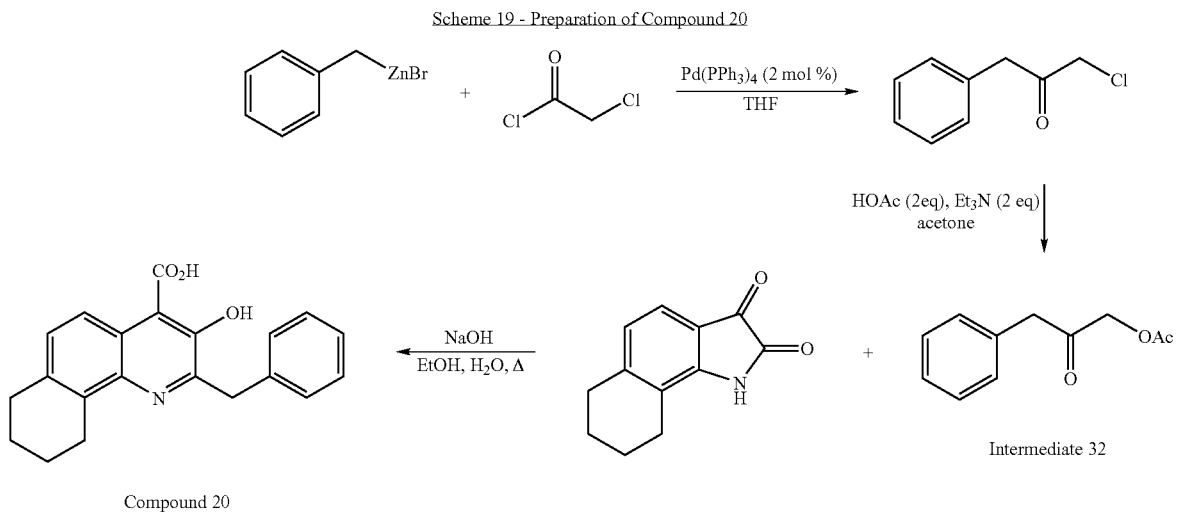

Example 20

Preparation of Compound 20

Intermediate 32

Acetic acid 2-oxo-3-phenyl-propyl ester

The procedure described above for the synthesis of 3-(3-Chlorophenyl)-2-oxopropyl acetate was followed, reacting 0.5 M THF solution of benzylzinc bromide (26 mL, 13 mmol), Pd(PPh$_3$)$_4$ (0.30 g, 0.26 mmol) with chloroacetyl chloride (26 mL, 13 mmol). Work-up of the reaction mixture gave crude product as a yellow oil.

This crude material was reacted with acetic acid (1.42 mL, 1.49 g, 24.8 mmol) and triethylamine (3.46 mL, 2.51 g, 24.8 mmol), as described above for the synthesis of 3-(3,4-dichlorophenyl)propan-2-one. Flash chromatography over silica gel (10-30% ethyl acetate in hexanes) gave pure product (0.83 g, 33% yield). 1H NMR (400 MHz, DMSO-D6) δ ppm 2.08 (s, 3H) 3.80 (s, 2H) 4.85 (s, 2H) 7.17-7.36 (m, 5H).

2-Benzyl-3-hydroxy-7,8,9,10-tetrahydro-benzo[h]quinoline-4-carboxylic acid

Compound 20

The procedure described above for the synthesis and purification of example 207 was followed, reacting 6,7,8,9-tetrahydrobenzo[g]indoline-2,3-dione (0.294 g, 1.46 mmol) with acetic acid 2-oxo-3-phenyl-propyl ester (0.364 g, 1.90 mmol). Product was obtained as a yellow powder (171 mg, 35% yield): 1H NMR (400 MHz, DMSO-D6) δ ppm 1.75-1.89 (m, 4H) 2.83 (t, J=6.06 Hz, 2H) 3.17 (t, J=6.10 Hz, 2H) 4.31 (s, 2H) 7.13-7.21 (m, 1H) 7.23-7.36 (m, 5H) 8.24 (d, J=9.09 Hz, 1H).

Scheme 20 - Preparation of Compound 21

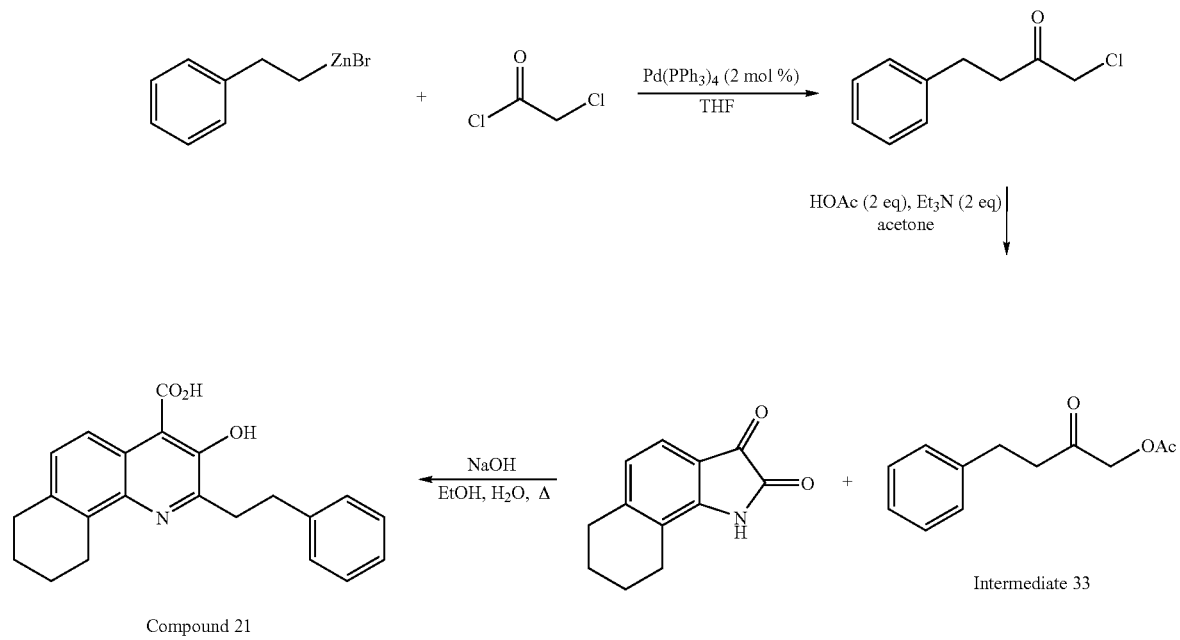

Example 21

Preparation of Compound 21

Intermediate 33

Acetic acid 2-oxo-4-phenyl-butyl ester

The procedure described above for the synthesis of 3-(3-Chlorophenyl)-2-oxopropyl acetate was followed, reacting 0.5 M THF solution of phenylethylzinc 10 bromide (26 mL, 13 mmol), Pd(PPh$_3$)$_4$ (0.30 g, 0.26 mmol) with chloroacetyl chloride (26 mL, 13 mmol). Work-up of the reaction mixture gave crude product as a yellow oil.

This crude material was reacted with acetic acid (1.42 mL, 1.49 g, 24.8 mmol) and triethylamine (3.46 mL, 2.51 g, 24.8 mmol), as described above for the synthesis of 3-(3,4-dichlorophenyl)propan-2-one. Flash chromatography over silica gel (10-30% ethyl acetate in hexanes) gave an impure mixture, which was used as such for the next step.

3-Hydroxy-2-phenethyl-7,8,9,10-tetrahydro-benzo [h]quinoline-4-carboxylic acid

Compound 21

The procedure described above for the synthesis and purification of example 7 was followed, reacting 6,7,8,9-tetrahydrobenzo[g]indoline-2,3-dione (0.294 g, 1.46 mmol) with acetic acid 2-oxo-4-phenyl-butyl ester (0.391 g (75% purity), 1.90 mmol). Product was obtained as a yellow powder (76 mg, 15% yield): 1H NMR (500 MHz, DMSO-D6) δ ppm 1.76-1.91 (m, 4H) 2.85 (t, J=5.95 Hz, 2H) 3.16 (t, J=7.80 Hz, 2H) 3.22 (t, J=6.10 Hz, 2H) 3.29 (t, J=7.78 Hz, 2H) 7.18 (t, J=7.02 Hz, 1H) 7.23-7.35 (m, 5H) 8.27 (d, J=7.93 Hz, 1H).

Scheme 21 - Synthesis of Compound 22

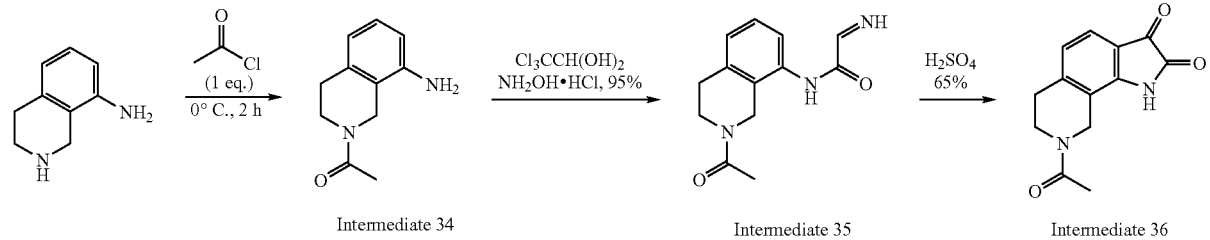

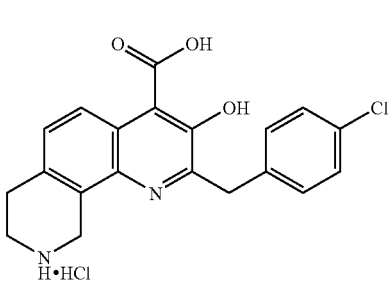

Compound 22

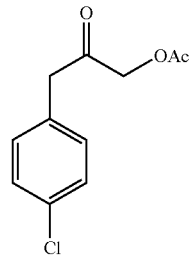

Intermediate 2

Example 22

Preparation of Compound 22

Intermediate 34

1-(8-Amino-3,4-dihydro-1H-isoquinolin-2-yl)-ethanone (a Mixture of Two Isomers in a 2:3 Ratio)

To a solution of 1,2,3,4-tetrahydro 5-aminoisoquinoline (2.1 g, 14.1 mmol) in 125 mL dichloromethane and 100 mL saturated NaHCO3 (aq.) at 0° C. was added acetyl chloride (1 mL, 14.1 mmol) in 25 mL dichloromethane dropwise. The resulting mixture was stirred at 0° C. for 30 min. The organic layer was separated quickly so that the organic layer remained relatively cool. To the organic layer was immediately added methylamine hydrochloride (1 g, 14.2 mmol) and diisopropylamine (2 mL, 14.1 mmol) to scavenge the unreacted acetyl chloride. Removal of the solvent followed by flash chromatography (silica gel, ethyl acetate:hexane=5:1) gave the desired amide 34 as a light yellow oil (2 g, 74%). 1H NMR (400 MHz, DMSO-D6) δ ppm 2.04 (s, 1.2H), 2.07 (s, 1.8H), 2.41 (dd, J=6.06, 6.19 Hz, 1H), 2.52 (m, 1H), 3.66 (dd, J=6.06, 6.19 Hz, 2H), 4.48 (s, 1.2H), 4.51 (s, 0.8H), 4.85-4.93 (bs, 2H), 6.36 (dd, J=7.33, 7.33 Hz, 1H), 6.47 (d, J=7.33 Hz, 0.6H), 6.49 (d, J=7.33 Hz, 0.4H), 6.85 (d, J=7.33 Hz, 0.6H) 6.88 (d, J=7.33 Hz, 0.4H).

Intermediate 35

N-(2-Acetyl-1,2,3,4-tetrahydro-isoquinolin-8-yl)-2-imino-acetamide (a Mixture of Two Isomers in a 2:3 Ratio)

The isatin synthesis described by Yang et al. (*J. Am. Chem. Soc.*, 1996, 118, 9557) was used. A mixture of chloral hydrate (2.4 g, 14.9 mmol), hydroxylamine hydrochloride (3.3 g, 47.8 mmol), sodium sulfate (19 g, 133.8 mmol), intermediate 34 (2.4 g, 12.6 mmol), aq. HCl (10 mL, 1N), and 90 mL water was stirred at 55° C. overnight. The reaction mixture was cooled to 25° C. The precipitate was collected by filtration, washed with water, and dried under vacuum overnight to provide the intermediate 35 (2.8 g, 85%) as a beige solid which was used without further purification in the next step. 1H NMR (400 MHz, DMSO-D6) δ ppm 2.07 (s, 1.8H), 2.08 (s, 1.2H), 2.62 (dd, J=5.94, 5.94 Hz, 0.8H), 2.72 (dd, J=5.94, 5.94 Hz, 1.2H), 3.63 (dd, J=6.06, 6.06 Hz, 2H), 4.61 (s, 1.2H), 4.66 (s, 0.8H), 7.07 (s, 0.4H), 7.09 (s, 0.6H), 7.19 (d, J=8.00 Hz, 0.4H), 7.21-7.25 (d, J=8.00 Hz, 0.6H), 7.30 (d, J=7.83 Hz, 0.4H), 7.33 (d, J=7.83 Hz, 0.6H), 7.66 (s, 1H), 9.61 (s, 1H), 12.19 (s, 1H).

Intermediate 36

8-Acetyl-6,7,8,9-tetrahydro-1H-pyrrolo[3,2-h]isoquinoline-2,3-dione (a Mixture of Two Isomers in a 2:3 Ratio)

Intermediate 35 from above was mixed with 11 mL concentrated sulfuric acid at 25° C. The resulting dark purple solution was heated to 85° C. gradually and stayed at this temperature for 10 min. The reaction mixture was then cooled to 25° C. 50 mL crushed ice was added, and the reaction mixture was allowed to stay at 0° C. for 30 min. The precipitate was collected by filtration, washed with water, and dried under vacuum overnight to give isatin 36 (1.7 g, 65%) as an orange solid, which was used for the next step without further purification. 1H NMR (400 MHz, DMSO-D6) δppm 2.08 (s, 1.2H), 2.10 (s, 1.8H), 2.58 (dd, J=5.81, 6.06 Hz, 0.8H), 2.69 (dd, J=5.81, 6.06 Hz, 1.2H), 3.70 (dd, J=6.23, 6.23 Hz, 2H), 4.63 (s, 1.2H), 4.69 (s, 0.8H), 6.91 (d, J=7.58 Hz, 0.4H), 6.92 (d, J=7.58 Hz, 0.6H), 7.33 (d, J=7.83 Hz, 0.4H), 7.37 (d, J=7.83 Hz, 0.6H), 11.12 (s, 0.4H), 11.15 (s, 0.6H).

2-(4-Chloro-benzyl)-3-hydroxy-7,8,9,10-tetrahydro-[1,9]phenanthroline-4-carboxylic acid

Compound 22

The procedure described by Cragoe et al. (*J. Org. Chem.*, 1953, 18, 561) was used. To a mixture of isatin 36 (0.85 g, 3.48 mmol) in 2 mL EtOH and 4 mL aq. 6 M KOH at 100° C. was added warm 3-(4-chlorophenyl)-2-oxopropyl acetate (0.9 g, 3.98 mmol) in 2 mL EtOH in small portions over 1 hour period. After the addition was completed, the reaction mixture was refluxed for additional 1 h. Removal of the solvent, the resulting yellow gum was acidified with aq. 1 N HCl to pH ~1. HPLC of the yellow precipitate under basic conditions afforded white solid, which was acidified at 0° C. with 1N aq. HCl to pH ~1. The precipitate was collected by centrifuge, washed with water, and dried under vacuum to yield compound 22 (0.144 g, 16%) as a yellow solid. 1H NMR (400 MHz, DMSO-D6) δ ppm 2.51-2.56 (m, 2H), 3.37-3.42 (m, 2H), 4.23 (s, 2H), 4.33 (bs, 2H), 7.18 (d, J=9.09 Hz, 1H), 7.27-7.33 (m, 2H), 7.33-7.39 (m, 2H), 8.95 (bs, 2H), 9.31 (d, J=9.09 Hz, 1H).

Scheme 22 - Synthesis of Compound 23

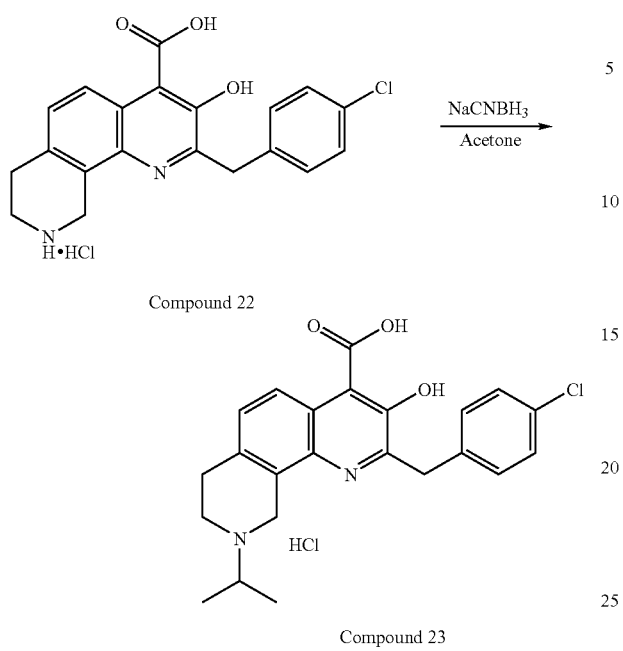

Compound 22

Compound 23

Example 23

Preparation of Compound 23

2-(4-Chloro-benzyl)-3-hydroxy-9-isopropyl-7,8,9,10-tetrahydro-[1,9]phenanthroline-4-carboxylic acid Compound 23

A mixture of compound 22 (0.12 g, 0.297 mmol), triethylamine (46 uL, 0.30 mmol), acetone (26 uL, 0.446 mmol), sodium cyanoborohydride (23 mg, 0.36 mmol), 3 mL methanol, and 3 drops of acetic acid was stirred at 25° C. overnight. LC/MS showed that about half of the starting material left. Water and triethylamine were added dropwise to dissolve the precipitate. HPLC of the clear reaction mixture afforded a white solid, which was acidified with aq. 1N HCl to pH ~1. The precipitate was collected by centrifuge, washed with water, and dried under vacuum to yield compound 23 (8.4 mg, 32% based on consumed starting material) as a white solid. 1H NMR (400 MHz, DMSO-D6) δ ppm 1.43 (d, J=6.57, 1.77 Hz, 3H), 1.43 (d, J=6.57, 3H), 3.30-3.48 (m, 2H), 3.61-3.92 (m, 3H), 4.38-4.61 (m, 4H), 7.21-7.32 (m, 3H) 7.39 (d, J=8.34 Hz, 2H) 9.32 (d, J=9.09 Hz, 1H).

Scheme 23 - Synthesis of Compound 24

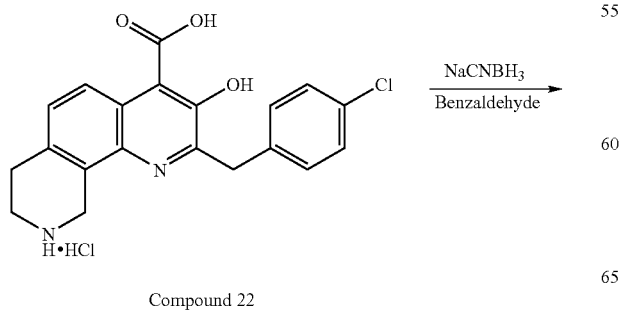

Compound 22

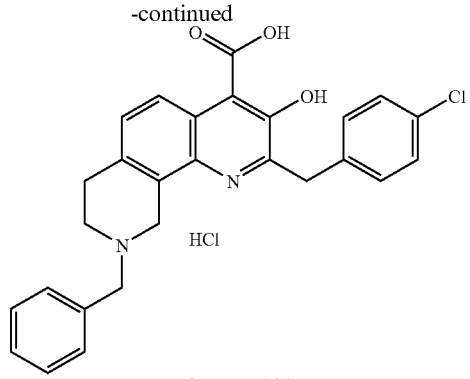

Compound 24

Example 24

Preparation Of Compound 24

9-Benzyl-2-(4-chloro-benzyl)-3-hydroxy-7,8,9,10-tetrahydro-[1,9]phenanthroline-4-carboxylic acid Compound 24

The procedure described above for the synthesis and purification of example 23 was followed, reacting 2-(4-Chloro-benzyl)-3-hydroxy-7,8,9,10-tetrahydro-[1,9]phenanthroline-4-carboxylic acid (0.12 g, 0.297 mmol) with benzaldehyde to give compound 24 (24.1 mg, 40%). White solid. 1H NMR (400 MHz, DMSO-D6) δ ppm 3.32-3.54 (m, 2H), 3.67-3.96 (m, 2H), 4.29 (s, 2H), 4.38-4.47 (m, 2H), 4.52 (s, 2H), 7.21 (d, J=8.84 Hz, 1H), 7.24-7.33 (m, 2H), 7.34-7.43 (m, 2H), 7.48-7.57 (m, 3H), 7.56-7.67 (m, 2H), 9.31 (d, J=8.84 Hz, 1H).

Scheme 24 - Synthesis of Compound 25

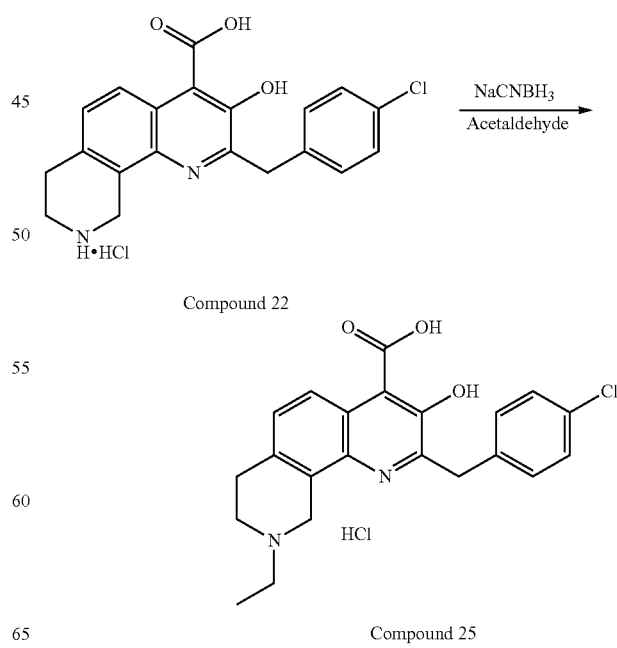

Compound 22

Compound 25

Example 25

Preparation of Compound 25

2-(4-Chloro-benzyl)-9-ethyl-3-hydroxy-7,8,9,10-tetrahydro-[1,9]phenanthroline-4-carboxylic acid Compound 25

The procedure described above for the synthesis and purification of example 23 was followed, reacting 2-(4-Chloro-benzyl)-3-hydroxy-7,8,9,10-tetrahydro-[1,9]phenanthroline-4-carboxylic acid (0.12 g, 0.297 mmol) with acetaldehyde to give compound 25 (2.2 mg, 3.4% based on consumed starting material). Light yellow solid. $^1$H NMR (400 MHz, DMSO-D6) δ ppm 1.38 (t, J=7.33 Hz, 3H), 2.55-2.60 (m, 1H), 2.66-2.76 (m, 1H), 3.34 (q, J=7.33 Hz, 2H), 3.64-3.93 (m, 2H), 4.30 (s, 2H), 4.40 (d, J=15.16 Hz, 1H), 4.62 (d, J=15.16 Hz, 1H), 7.26-7.34 (m, 3H), 7.34-7.41 (m, 2H), 9.08 (d, J=8.08 Hz, 1H).

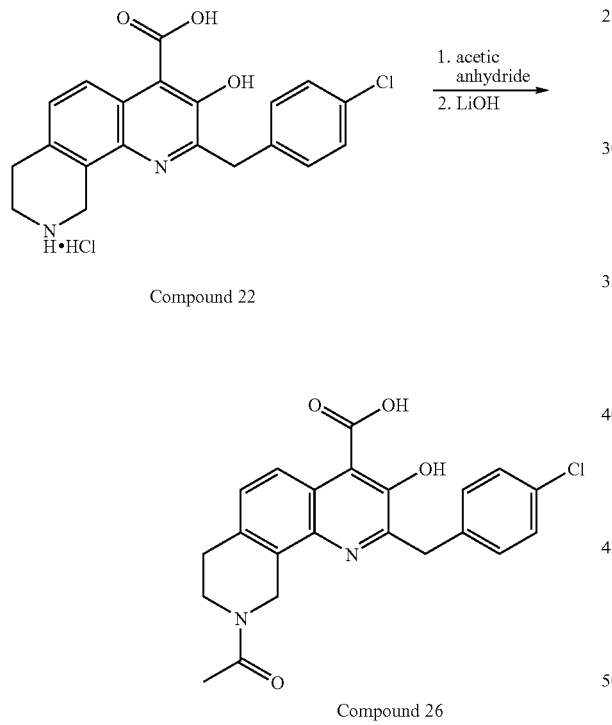

Example 26

Preparation of Compound 26

9-Acetyl-2-(4-chloro-benzyl)-3-hydroxy-7,8,9,10-tetrahydro-[1,9]phenanthroline-4-carboxylic acid Compound 26 (Mixture of Two Isomers)

To 2-(4-Chloro-benzyl)-3-hydroxy-7,8,9,10-tetrahydro-[1,9]phenanthroline-4-carboxylic acid (0.14 g, 0.346 mmol) in 2 mL pyridine was added triethylamine (60 uL, 0.43 mmol) and acetic anhydride (0.18 mL, 2.07 mmol) at 0° C. The reaction mixture was warmed to 25° C. and stirred overnight. HPLC of the reaction mixture afforded the acetamide ester (90 mg, 0.20 mmol) as a white solid, which was treated with LiOH (36 mg, 0.80 mmol) in 1 mL water. The mixture was stirred at 25° C. for 5 h. DMSO and triethylamine were added to the reaction mixture dropwise to dissolve the precipitate. HPLC of the clear solution gave compound 26 (20.7 mg, 25%) as a yellow solid. $^1$H NMR (400 MHz, DMSO-D6) δ ppm 2.24 (s, 3H), 3.21-3.42 (m, 2H), 3.77-3.87 (m, 2H), 4.34 (s, 2H), 4.73-4.84 (m, 2H), 7.27-7.42 (m, 5H), 8.49-8.57 (m, 1H).

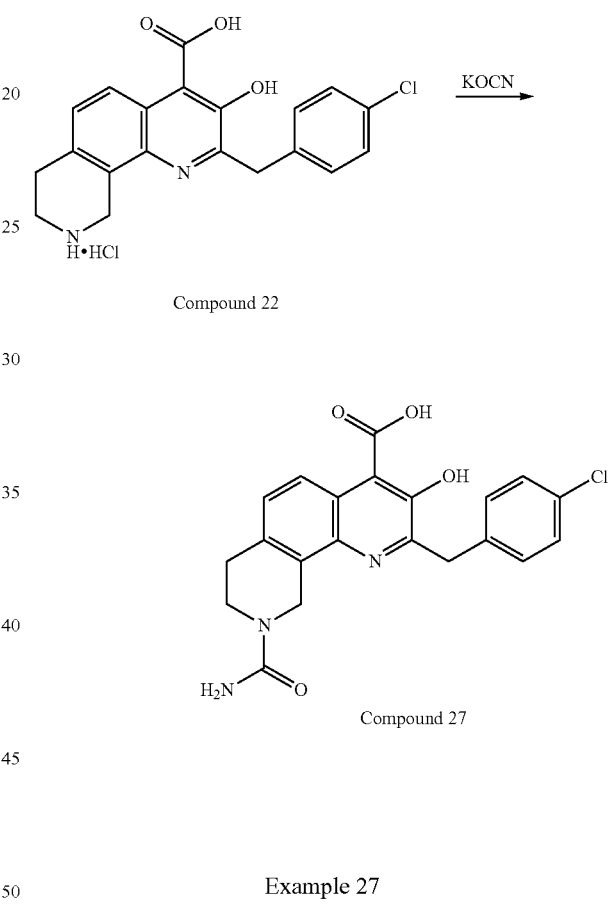

Example 27

Preparation of Compound 27

9-Carbamoyl-2-(4-chloro-benzyl)-3-hydroxy-7,8,9,10-tetrahydro-[1,9]phenanthroline-4-carboxylic acid A mixture of 2-(4-Chloro-benzyl)-3-hydroxy-7,8,9,10-tetrahydro-[1,9]phenanthroline-4-carboxylic acid (0.213 g, 0.53 mmol), acetic acid (0.6 mL, 5.3 mmol), triethylamine (0.146 mL, 1.06 mmol), KOCN (43 mg, 0.53 mmol), and pyridine (0.84 mL, 5.3 mmol) was stirred at 25° C. overnight. The solid was removed by filtration. HPLC of the mother liquor gave pure product (49.1 mg, 22%) as a beige solid. $^1$H NMR (400 MHz, DMSO-D6) δ ppm 3.25 (m, 2H), 3.68 (m, 2H), 4.34 (s, 2H), 4.63 (s, 2H), 7.22-7.45 (m, 5H), 8.47 (d, J=9.09 Hz, 1H).

Scheme 27 - Synthesis of Compound 28 and 29

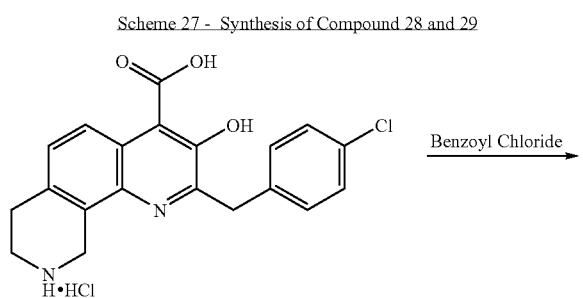

Compound 22

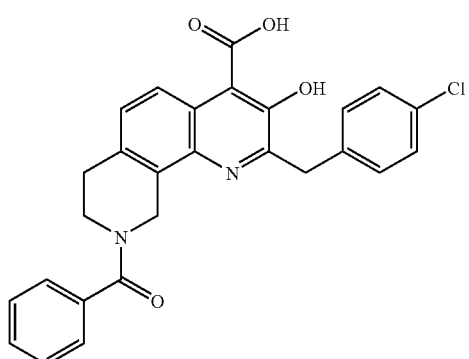

Compound 28

+

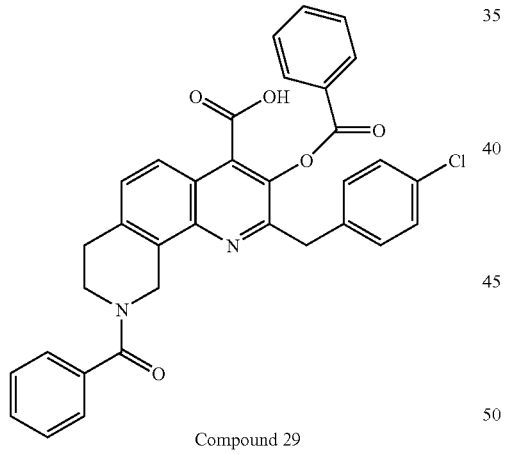

Compound 29

Examples 28 and 29

Preparation of Compound 28 and Compound 29

9-Benzoyl-2-(4-chloro-benzyl)-3-hydroxy-7,8,9,10-tetrahydro-[1,9]phenanthroline-4-carboxylic acid and 9-Benzoyl-3-benzoyloxy-2-(4-chlorobenzyl)-7,8,9,10-tetrahydro-[1,9]phenanthroline-4-carboxylic acid To 2-(4-Chloro-benzyl)-3-hydroxy-7,8,9,10-tetrahydro-[1,9]phenanthroline-4-carboxylic acid (0.132 g, 0.32 mmol) in 2 mL dichloromethane 0° C. was added benzoyl chloride (57 uL, 0.48 mmol) and triethylamine (0.10 mL, 0.74 mmol). The mixture was stirred at 25° C. overnight. HPLC of the mixture gave compound 28 (14.6 mg, 9.7%) as a yellow solid, and compound 29 (4.0 mg, 2.3%) as a white solid. Compound 28: 1H NMR (500 MHz, DMSO-D6) δ ppm 3.32 (dd, J=5.80, 5.80 Hz, 2H), 3.81-3.83 (m, 2H), 4.34 (s, 2H), 4.81 (s, 2H), 7.27-7.34 (m, 3H), 7.35-7.41 (m, 2H), 7.43-7.54 (m, 5H), 8.52 (d, J=8.85 Hz, 1H). Compound 29: 1H NMR (400 MHz, DMSO-D6) δ ppm 3.37-3.46 (m, 2H), 3.56-3.60 (m, 2H), 4.28 (s, 2H), 5.00 (s, 2H), 7.15-7.34 (m, 4H), 7.45-7.57 (m, 6H), 7.64 (dd, J=7.71, 8.21 Hz, 2H), 7.80 (dd, J=7.71, 8.21 Hz, 1H), 7.88-7.98 (m, 1H), 8.10 (d, J=7.07 Hz, 2H).

Scheme 28 - Synthesis of Compound 30

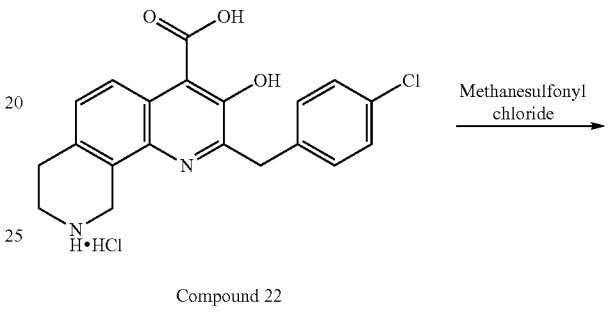

Compound 22

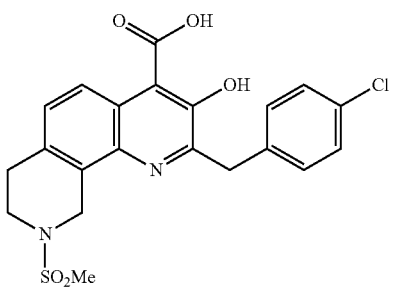

Compound 30

Example 30

Preparation of Compound 30

2-(4-Chloro-benzyl)-3-hydroxy-9-methanesulfonyl-7,8,9,10-tetrahydro-[1,9]phenanthroline-4-carboxylic acid Compound 30

The procedure described above for the synthesis and purification of example 28 was followed, reacting 2-(4-Chloro-benzyl)-3-hydroxy-7,8,9,10-tetrahydro-[1,9]phenanthroline-4-carboxylic acid (0.219 g, 0.54 mmol) with methanesulfonyl chloride (1 eq.) to give compound 30 (19 mg, 7.9%). 1H NMR (400 MHz, DMSO-D6) δ ppm 2.97 (s, 3H), 3.34 (dd, J=5.68, 6.06 Hz, 2H), 3.53 (dd, J=5.68, 6.06 Hz, 2H), 4.27 (s, 2H), 4.45 (s, 2H), 7.25 (d, J=8.84 Hz, 1H), 7.31 (m, 2H), 7.37 (m, 2H), 8.97 (d, J=8.84 Hz, 1H).

Scheme 29 - Synthesis of Compound 31 and 32

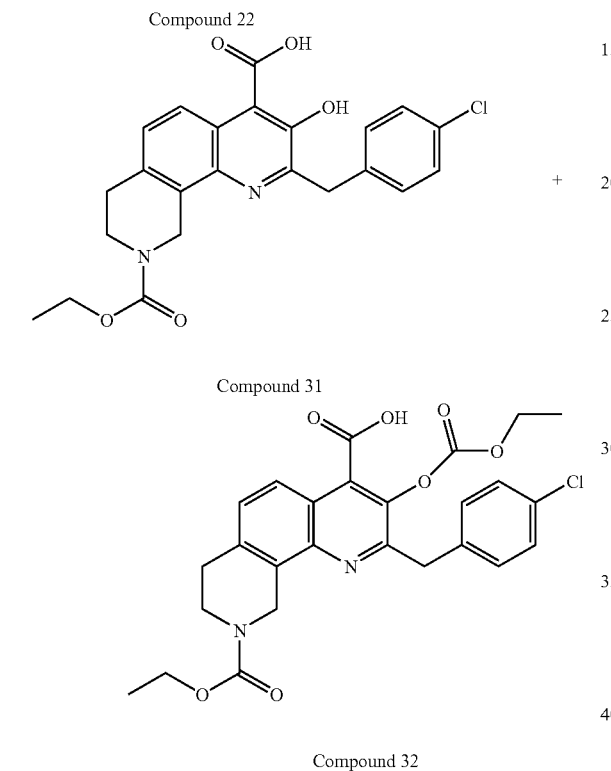

Compound 22

Compound 31

Compound 32

Examples 31 and 32

Preparation of Compound 31 and Compound 32

2-(4-Chloro-benzyl)-3-hydroxy-7,10-dihydro-8H-[1,9]phenanthroline-4,9-dicarboxylic acid 9-ethyl ester (Compound 31) and 2-(4-Chloro-benzyl)-3-ethoxycarbonyloxy-7,10-dihydro-8H-[1,9]phenanthroline-4,9-dicarboxylic acid 9-ethyl ester (compound 32)

The procedure described above for the synthesis and purification of example 28 was followed, reacting 2-(4-Chloro-benzyl)-3-hydroxy-7,8,9,10-tetrahydro-[1,9]phenanthroline-4-carboxylic acid (0.13 g, 0.32 mmol) with ethyl chloroformate to give compound 31 (23.2 mg, 16.5%) as a yellow solid, and compound 32 (8.5 mg, 5.2%) as a white solid. Compound 31: 1H NMR (400 MHz, DMSO-D6) δppm 1.24 (t, J=7.07 Hz, 3H), 3.25 (dd, J=5.68, 6.19 Hz, 2H), 3.73 (dd, J=5.68, 6.19 Hz, 2H), 4.12 (t, J=7.07 Hz, 2H), 4.32 (s, 2H), 4.67 (s, 2H), 7.30-7.42 (m, 5H), 8.37 (d, J=8.84 Hz, 1H). Compound 32: 1H NMR (400 MHz, DMSO-D6) δ ppm 1.22 (t, J=7.16 Hz, 3H), 1.26 (t, J=7.07 Hz, 3H), 3.29 (dd, J=5.05, 5.81 Hz, 2H), 3.76 (dd, J=5.05, 5.81 Hz, 2H), 4.12 (q, J=7.16 Hz, 2H), 4.22 (q, J=7.07 Hz, 2H), 4.26 (s, 2H), 4.74 (s, 2H), 7.28 (m, 2H), 7.35 (m, 2H), 7.54 (d, J=8.84 Hz, 1H), 7.85 (d, J=8.84 Hz, 1H).

Scheme 30 - Synthesis of Compound 33

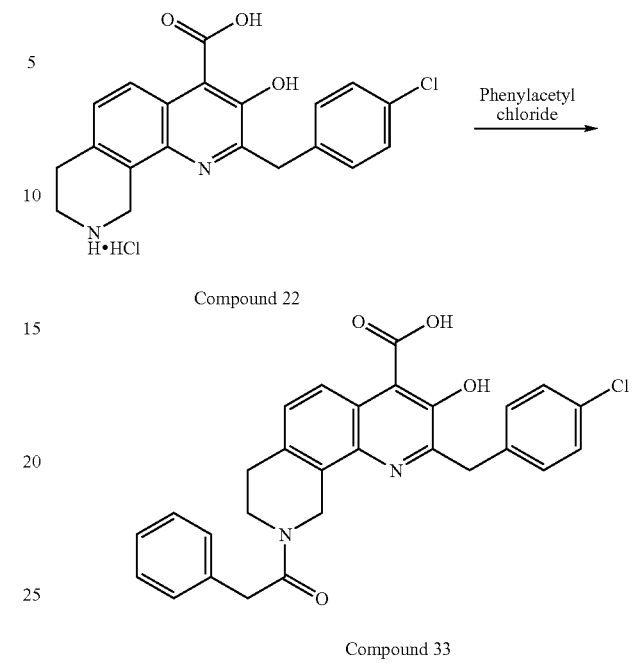

Compound 22

Compound 33

Example 33

Preparation of Compound 33

2-(4-Chloro-benzyl)-3-hydroxy-9-phenylacetyl-7,8,9,10-tetrahydro-[1,9]phenanthroline-4-carboxylic acid Compound 33 (Mixture of Two Isomers)

The procedure described above for the synthesis and purification of example 28 was followed, reacting 2-(4-Chloro-benzyl)-3-hydroxy-7,8,9,10-tetrahydro-[1,9]phenanthroline-4-carboxylic acid (0.13 g, 0.32 mmol) with phenylacetyl chloride to give compound 33 (27.2 mg, 17.5%, mixture of two isomers in a 2:1 ratio) as a yellow solid. 1H NMR (400 MHz, DMSO-D6) δ ppm 3.06-3.16 (m, 2H), 3.75-3.92 (m, 4H), 4.28 (s, 2H), 4.74 (s, 1.3H) 4.80-4.88 (m, 0.7H), 7.14-7.40 (m, 10H), 8.37-8.64 (m, 1H).

Scheme 31 - Synthesis of Compound 34

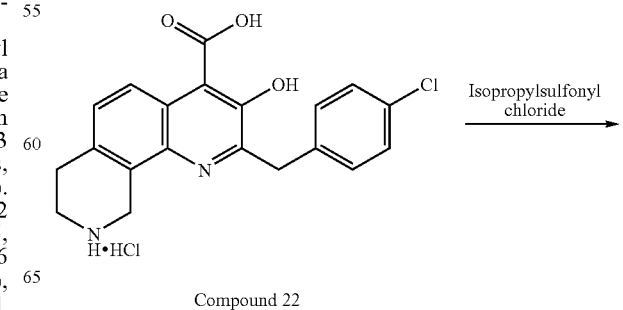

Compound 22

69

-continued

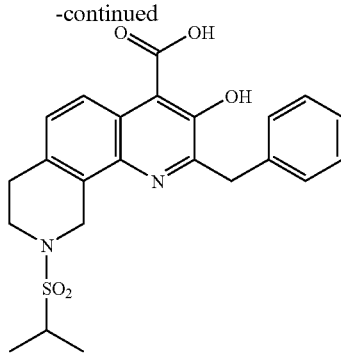

Compound 34

Example 34

Preparation of Compound 34

2-(4-Chloro-benzyl)-3-hydroxy-9-(propane-2-sulfonyl)-7,8,9,10-tetrahydro-[1,9]phenanthroline-4-carboxylic acid Compound 34 (Mixture of Two Isomers in a 2:1 Ratio)

The procedure described above for the synthesis and purification of example 28 was followed, reacting 2-(4-Chlorobenzyl)-3-hydroxy-7,8,9,10-tetrahydro-[1,9]phenanthroline-4-carboxylic acid (0.13 g, 0.32 mmol) with isopropylsulfonyl chloride (1 eq.) to give compound 34 as a yellow solid (5.2 mg, 3.4%, mixture of two isomers in a 2:1 ratio). 1H NMR (500 MHz, DMSO-D6) δ ppm 1.23 (d, J=7.02 Hz, 6H), 3.11-3.14 (m, 2H), 3.23-3.32 (septlet, J=5.00 Hz, 1H), 3.56 (dd, J=5.95, 5.95 Hz, 0.6H), 3.63 (dd, J=5.95, 5.95 Hz, 1.4H), 4.25 (s, 2H), 4.46 (s, 0.6H), 4.53 (s, 1.4H), 7.23-7.27 (m, 1H), 7.28 (d, J=10.00 Hz, 2H) 7.33 (d, J=10.00 Hz, 2H) 8.78-8.87 (m, 1H).

70

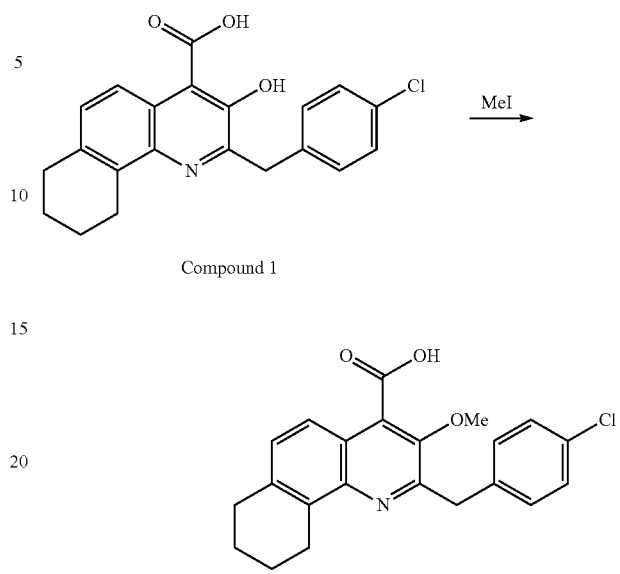

Scheme 32 - Synthesis of Compound 35

Compound 1

Compound 35

Example 35

Preparation of Compound 35

2-(4-Chloro-benzyl)-3-methoxy-7,8,9,10-tetrahydrobenzo[h]quinoline-4-carboxylic acid Compound 35

To 2-(4-Chloro-benzyl)-3-hydroxy-7,8,9,10-tetrahydrobenzo[h]quinoline-4-carboxylic acid (0.117 g, 0.32 mmol) in 2 mL acetone at room temperature was added potassium carbonate (0.132 g, 0.96 mmol) and iodomethane (0.136 g, 0.96 mmol). The mixture was stirred overnight. HPLC of the mixture gave compound 35 (90 mg, 75%) as a white solid. 1H NMR (400 MHz, DMSO-D6) δ ppm 1.69-1.94 (m, 4H), 2.76-2.88 (m, 2H), 3.11-3.19 (m, 2H), 3.80 (s, 3H), 4.21 (s, 2H), 7.15 (d, J=8.59 Hz, 1H), 7.31 (s, 4H), 7.49 (d, J=8.59 Hz, 1H).

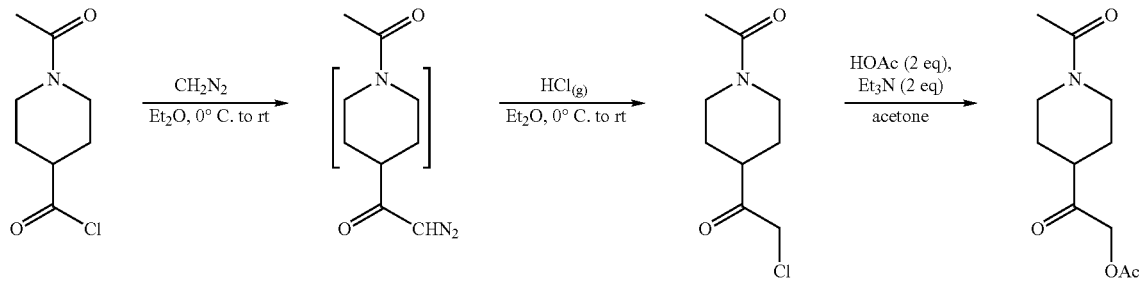

Scheme 33 - Preparation of Compound 36 and 37

Intermediate 37

Intermediate 38

+

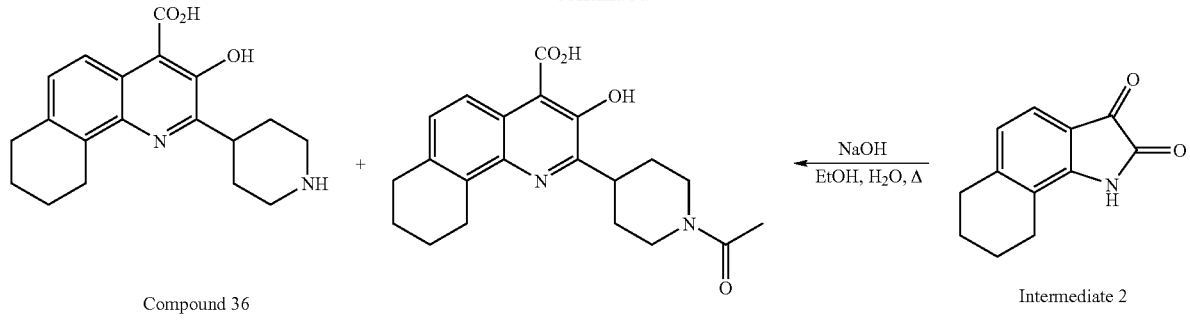

Compound 36

Compound 37

Intermediate 2

Example 36

Preparation of Compound 36 and 37

3-Hydroxy-2-piperidin-4-yl-7,8,9,10-tetrahydro-benzo[h]quinoline-4-carboxylic acid (Compound 36) and 2-(1-acetyl-piperidin-4-yl)-3-hydroxy-7,8,9,10-tetrahydro-benzo[h]quinoline-4-carboxylic acid (Compound 37)

Intermediate 37 was synthesized by Arndt-Eistert homologation of the acid chloride using the procedure described for 1-Chloro-3-(thiophen-2-yl)propan-2-one (intermediate 15). Reacting acid chloride (1.35 g, 7.1 mmol) with 40 ml of an ethereal diazomethane solution followed by passing HCl gas. The crude material was used as such in the next step. Synthesis of intermediate 38 was done using the procedure described above for the synthesis of 3-(3,4-dichlorophenyl)-2-oxopropyl acetate was followed, reacting 1-chloro-3-(thiophen-2-yl) propan-2-one (1.16 g, 5.73 mmol) with acetic acid (0.66 mL, 0.69 g, 12 mmol) and triethylamine (1.60 mL, 1.16 g, 11.5 mmol). The crude intermediate 40 was used as such in the next step. Compounds 36 and 37 was synthesized using the procedure described above for the synthesis and purification of example 7, reacting 6,7,8,9-tetrahydrobenzo[g]indoline-2,3-dione (0.112 g, 0.557 mmol) with acetic acid 2-(1-acetyl-piperidin-4-yl)-2-oxoethyl ester (intermediate 40, 0.165 g, 0.724 mmol). Two products were isolated as white solids. Compound 36 (18.1 mg, 10% yield): 1H NMR (400 MHz, DMSO-D6) δ ppm 1.72-1.89 (m, 4H) 1.96-2.19 (m, 4H) 2.69-2.87 (m, 2H) 3.06-3.16 (m, 2H) 3.19 (t, J=5.81 Hz, 2H) 3.38-3.50 (m, 2H) 3.52-3.67 (m, 1H) 7.07 (d, J=8.84 Hz, 1H) 8.28 (br s, 1H) 8.54 (br s, 1H) 9.17 (d, J=8.59 Hz, 1H); Compound 37 (10 mg, 5% yield): 1H NMR (500 MHz, DMSO-D6) δ ppm 1.65-1.73 (m, 1H) 1.77-1.99 (m, 7H) 2.06 (s, 3H) 2.77 (t, J=11.44 Hz, 1H) 2.84 (t, J=6.10 Hz, 2H) 3.15-3.30 (m, 3H) 3.54 (t, J=11.14 Hz, 1H) 3.98 (d, J=13.73 Hz, 1H) 4.51 (d, J=13.73 Hz, 1H) 7.26 (d, J=8.85 Hz, 1H) 8.31 (d, J=8.85 Hz, 1H).

Example 37

Assay of Compounds of the Invention

Compounds of the invention can be assayed for selectin inhibitory activity using any of the procedures known in the art. One convenient procedure is the determination of IC50 values for inhibition of P-selectin binding to P-selectin glycoprotein ligand-1 (PSGL-1) using Biacore.

The Biacore 3000 is an instrument that uses surface plasmon resonance to detect binding of a solution phase analyte to an immobilized ligand on a sensor chip surface. The analyte sample is injected under flow using a microfluidic system. Binding of analyte to ligand causes a change in the angle of refracted light at the surface of the sensor chip, measured by the Biacore instrument in resonance units (RUs).

SGP-3 is a purified sulfoglycopeptide form of human PSGL-1 that contains the P-selectin binding determinants (See Somers et al., 2000, Cell 103, 467-479). SGP-3 was biotinylated via amine chemistry at a unique C-terminal lysine residue and immobilized on streptavidin-coated SA sensor chip. A solution containing a soluble recombinant truncated form of human P-selectin comprised of the lectin and EGF domains (P-LE) was delivered to the SGP-3 coated sensor chip. The P-LE solution contains 100 mM HEPES, 150 mM NaCl, 1 mM $CaCl_2$, 1 mM $MgCl_2$, 0.05% P40, 10% DMSO. $K_D$ values were typically calculated to be approximately 778+/−105 nM using this Biacore assay format (Somers et al., supra).

Small molecule P-selectin inhibitors are incubated for 1 hour in 100 mM HEPES, 150 mM NaCl, 1 mM $CaCl_2$, 1 mM $MgCl_2$, 0.05% P40, 10% DMSO, prior to introducing them into the Biacore 3000. Solutions are filtered if formation of precipitate is visible. Soluble P-LE is added to the small molecule solution at final concentrations 500 nM and 500 uM respectively. Sample injections are run in duplicates, and each compound is assayed at least twice.

The Biacore assay measures the signal in RU produced by binding of P-LE to SGP-3 in the presence and absence of inhibitors. Percent inhibition of binding is calculated by dividing the inhibited signal by the uninhibited signal subtracting this value from one then multiplying by one hundred. Inhibitors, with greater than 50% inhibition at 500 uM, are assayed again using a series of two fold dilutions. The data from this titration are plotted, RU values vs. concentration, and the $IC_{50}$ is determined by extrapolation from the plot. All RU values are blank and reference subtracted prior to percent inhibition and $IC_{50}$ determination. Glycerrhizzin is used as a positive control, inhibiting 50% at 1 mM.

Compounds 1-6 were assayed as described above. IC50 values for four of the compounds ranged from 125 μM to 500 μM. One compound showed 17% inhibition at 500 μM, and one compound showed 11% inhibition at 125 μM.

Compounds 7-10, 17-20 and 22-33 also were tested as above. Six of the compounds displayed $IC_{50}$ values ranging from 100 μM to 1250 μM. The percentage inhibition at 250 μM for an additional three compounds ranged from 46% to 58%. The percentage inhibition at 500 μM for an additional ten compounds ranged from 5% to 55%, with three of the compound showing no significant percentage inhibition at that concentration. One further compound displayed 24% inhibition at 1000 μM.

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A process for preparing a compound of formula III:

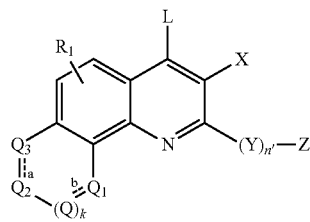

III or a pharmaceutically acceptable salt thereof,
wherein:
bond a and bond b can each independently be a single bond or a double bond;
k is 0 or 1;
$Q_1$, $Q_2$, and $Q_3$ are each independently $CR_{2'}$, N or $NR_{13}$;
Q is N;
L is $CO_2H$, an ester thereof, or a pharmaceutically acceptable acid mimetic;
Y is O, $(CR_3R_4)_p$ or $NR_5$;
n' is 0 or 1:
p is 1 to 3;
X is hydrogen, OH, $OR_3$, $OC_{1-6}$ alkyl, OC(=O)-aryl, OC(=O)$C_{1-6}$ alkyl, OC(=O)O$C_{1-6}$ alkyl, or $NR_3R_3$;
each $R_1$, $R_3$, $R_{3'}$ and $R_4$ is independently selected from the group consisting of hydrogen, $C_{1-6}$ alkyl, $C_{1-6}$ perhaloalkyl, $OC_{1-8}$ alkyl, $OC_{1-6}$ perhaloalkyl, thioalkyl, CN, OH, SH, $(CH_2)_nOSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)NR_6R_9$, $NR_8R_9$, C(=O)$R_{12}$, aryl, heterocyclo, C(=O)aryl, C(=O)heterocyclo, OC(=O)aryl, OC(=O)heterocyclo, Oaryl, Oheterocyclo, arylalkyl, OC(=O)arylalkyl, Oarylalkyl, alkenyl, alkynyl, and NHCOR$_8$, wherein any of said alkyl, Oalkyl, aryl, heterocyclo, C(=O)aryl, C(=O)heterocyclo, OC(=O)aryl, O—C(=O)heterocyclo, O-aryl, O—heterocyclo, arylalkyl, C(=O)arylalkyl, O—C(=O)arylalkyl, O-arylalkyl, alkenyl or alkynyl can optionally be substituted with up to three substituents selected from the group consisting of halogen, $C_{1-6}$ alkyl, $OC_{1-6}$ alkyl and CN;
each $R_{2'}$ is independently selected from the group consisting of hydrogen, $C_{1-6}$ alkyl, $C_{1-6}$ perhaloalkyl, $OC_{1-6}$ alkyl, perhaloalkyl halogen, thioalkyl, CN, OH, SH, $(CH_2)_nOSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)NR_8R_9$, $NR_8R_9$, C(=O)$R_{12}$, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl, alkynyl, and NHCOR$_6$, wherein any of said alkyl, Oalkyl, aryl, heterocyclo, C(=O)aryl, C(=O)heterocyclo, O—C(=O)aryl, O—C(=O)heterocyclo, O-aryl, O-heterocyclo, arylalkyl, C(=O)arylalkyl, O—C(=O) arylalkyl O-arylalkyl, alkenyl or alkynyl can optionally be substituted with to three substituents selected from the group consisting of halogen, $C_{1-6}$ alkyl, $OC_{1-6}$ alkyl and CN;

each $R_6$ and $R_7$ is independently selected from the group consisting of hydrogen and $C_{1-6}$ alkyl that is optionally substituted with up to three substituents selected from the group consisting of OH, $CF_3$, SH and halogen;

each $R_5$, $R_6$ and $R_9$ is independently selected from the group consisting of hydrogen, $C_{1-6}$ alkyl, $C_{1-6}$ haloalkyl, thioalkyl, OH, $(CH_2)_lOSO_3H$, $(CH_2)_lSO_3R_{10}$, $(CH_2)_nCO_2R_{10}$, $SO_3R_{10}$, $PO_3R_{10}R_{11}$, $(CH_2)_nSO_2(CH_2)_nNR_{10}R_{11}$, $(CH_2)_nCONR_{10}R_{11}$, $COR_{10}$, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl, and alkynyl, wherein any of said alkyl, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl or alkynyl can optionally be substituted with up to three substituents selected from the group consisting of halogen, $C_{1-6}$ alkyl, $OC_{1-6}$ alkyl and CN;

each n is an independently selected integer from 0 to 6;
each l is an independently selected integer from 1 to 6;

each $R_{10}$ and $R_{11}$ is independently selected from the group consisting of hydrogen and $C_{1-6}$ alkyl that is optionally substituted with up to three substituents selected from the group consisting of OH, $CF_3$, SH and halogen;

each $R_{12}$ is independently selected from the group consisting of hydrogen, $C_{1-6}$ alkyl, $C_{1-6}$ perhaloalkyl, $OC_{1-6}$ alkyl, $OC_{1-6}$ perhaloalkyl, thioalkyl, OH, $(CH_2)_lOSO_3H$, $(CH_2)_lSO_3H$, $(CH_2)_lCO_2R_6$, $(CH_2)_lSO_2NR_8R_9$, $(CH_2)_lC(=O)NR_8R_9$, $NR_8R_9$, alkenyl, alkynyl, or NHCOR$_8$, wherein any of said alkyl, Oalkyl, alkenyl or alkynyl can optionally be substituted with up to three substituents selected from the group consisting of halogen, $C_{1-6}$ alkyl, $OC_{1-6}$ alkyl and CN;

each $R_{13}$ is selected from hydrogen, C(=O)$R_{14}$, $SO_2R_{14}$, $C_{1-6}$ alkyl, $C_{1-6}$ haloalkyl, thioalkyl, OH, $(CH_2)_lOSO_3H$, $(CH_2)_lSO_3R_{10}$, $(CH_2)_nCO_2R_{10}$, $SO_3R_{10}$, $PO_3R_{10}R_{11}$, $(CH_2)_nSO_2(CH_2)_nNR_{10}R_{11}$, $(CH_2)_nCONR_{10}R_{11}$, $COR_{10}$, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl, and alkynyl, wherein any of said alkyl, aryl, heterocyclo, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl or alkynyl can optionally be substituted with up to three substituents selected from the group consisting of halogen, $C_{1-6}$ alkyl, $OC_{1-6}$ alkyl and CN;

$R_{14}$ is independently selected from the group consisting of $C_{1-10}$ alkyl, $OC_{1-10}$ alkyl and $NR_6R_7$;

Z is aryl, arylalkyl, heteroaryl or heterocycle, wherein each of said aryl, arylalkyl, heteroaryl and heterocyclo is optionally substituted; and which comprises one of the following:
a) reacting a compound of formula $$\text{III}$$

[Structure: quinoline with L at 4-position, $R_1$, X at 3-position, $(Y)_{n'}$—Z at 2-position, $Q_3$, $Q_2$, $Q_1$, $(Q)_k$, bonds a and b]

with compound of formula:

[Structure: AcO—CH$_2$—C(=O)—$(Y)_{n'}$—Z]

wherein Ac is acetyl to give a corresponding compound of formula III wherein L is CO$_2$H in the 4 position and X is OH in the 3 position; and
b) converting a compound of formula III to a pharmaceutically acceptable salt thereof or vice versa; and
c) converting a compound of formula III having a reactive substituent group or site to a different compound of formula III.

2. A compound of Formula III:

$$\text{III}$$

[Structure: quinoline with L at 4-position, $R_1$, X at 3-position, $(Y)_{n'}$—Z at 2-position, $Q_3$, $Q_2$, $Q_1$, $(Q)_k$, bonds a and b]

or a pharmaceutically acceptable salt thereof,
wherein: bond a and bond b can each independently be a single bond or a double bond;
k is 0 or 1;
$Q_1$, $Q_2$, and $Q_3$ are each independently $CR_{2'}$, N or $NR_{13}$;
Q is N;
L is CO$_2$H or an ester thereof;
Y is O, $(CR_3R_4)_p$ or $NR_5$;
n' is 0 or 1;
p is 1 to 3;
X is OH, OR$_3$, OC$_{1-6}$ alkyl, OC(=O)aryl, OC(=O)C$_{1-6}$ alkyl, OC(=O)OC$_{1-6}$ alkyl, or $NR_3R_{3'}$;
each $R_1$, $R_3$, $R_{3'}$ and $R_4$ is independently selected from the group consisting of hydrogen, C$_{1-6}$ alkyl, C$_{1-6}$ perhaloalkyl, OC$_{1-6}$ alkyl, OC$_{1-6}$ perhaloalkyl, halogen, thioalkyl, CN, OH, SH, (CH$_2$)$_n$OSO$_3$H, (CH$_2$)$_n$SO$_3$H, (CH$_2$)$_n$CO$_2$R$_6$, OSO$_3$R$_6$, SO$_3$R$_6$, PO$_3$R$_6$R$_7$, (CH$_2$)$_n$SO$_2$NR$_8$R$_9$, (CH$_2$)$_n$C(=O)NR$_8$R$_9$, NR$_6$R$_9$, C(=O)R$_{12}$, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl, alkynyl, and NHCOR$_8$, wherein any of said alkyl, Oalkyl, aryl, heterocyclo, C(=O)aryl, C(=O)heterocyclo, O—C(=O)aryl, O—C(=O)heterocyclo, O-aryl, O-heterocyclo, arylalkyl, C(=O)arylalkyl, O—C(=O)arylalkyl, alkenyl or alkynyl can optionally be substituted with up to three substituents selected from the group consisting of halogen, C$_{1-6}$ alkyl, OC$_{1-6}$ alkyl and CN;
each $R_{2'}$ is independently selected from the group consisting of hydrogen, C$_{1-6}$ alkyl, C$_{1-6}$ perhaloalkyl, OC$_{1-6}$ alkyl, OC$_{1-6}$ perhaloalkyl, halogen, thioalkyl, CN, OH, SH, (CH$_2$)$_n$OSO$_3$H, (CH$_2$)$_n$SO$_3$H, (CH$_2$)$_n$CO$_2$R$_6$, OSO$_3$R$_6$, SO$_3$R$_6$, PO$_3$R$_6$R$_7$, (CH$_2$)$_n$SO$_2$NR$_8$R$_9$, (CH$_2$)$_n$C(=O)NR$_8$R$_9$, NR$_8$R$_9$, C(=O)R$_{12}$, aryl, heterocyclo, C(=O)aryl, C(=O)heterocyclo, OC(=O)aryl, OC(=O)heterocyclo, Oaryl, Oheterocyclo, arylalkyl, OC(=O)arylalkyl, OC(=O)arylalkyl, Oarylalkyl, alkenyl, alkynyl, and NHCOR$_6$, wherein any of said alkyl, Oalkyl, aryl, heterocyclo, C(=O)aryl, C(=O)heterocyclo, O—C(=O)aryl, O—C(=O)heterocyclo, O-aryl, O-heterocyclo, arylalkyl, C(=O)arylalkyl, O—C(=O)arylalkyl, O-arylalkyl, alkenyl or alkynyl can optionally be substituted with up to three substituents selected from the group consisting of halogen, C$_{1-6}$ alkyl, OC$_{1-6}$ alkyl and CN;
each $R_6$ and $R_7$ is independently selected from the group consisting of hydrogen and C$_{1-6}$ alkyl that is optionally substituted with up to three substituents selected from the group consisting of OH, CF$_3$, SH and halogen;
each $R_5$, $R_8$ and $R_9$ is independently selected from the group consisting of hydrogen, C$_{1-6}$ alkyl, C$_{1-6}$ haloalkyl, thioalkyl, OH, (CH$_2$)$_l$OSO$_3$H, (CH$_2$)$_l$SO$_3$R$_{10}$, (CH$_2$)$_n$CO$_2$R$_{10}$, SO$_3$R$_{10}$, PO$_3$R$_{10}$R$_{11}$, (CH$_2$)$_n$SO$_2$(CH$_2$)$_n$NR$_{10}$R$_{11}$, (CH$_2$)$_n$CONR$_{10}$R$_{11}$, COR$_{10}$, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl, and alkynyl, wherein any of said alkyl, aryl, heterocyclo, C(=O)aryl, C(=O)heterocyclo, OC(=O)aryl, OC(=O)heterocyclo, Oaryl, Oheterocyclo, arylalkyl, C(=O)arylalkyl, OC(=O)arylalkyl, Oarylalkyl, alkenyl or alkynyl can optionally be substituted with up to three substituents selected from the group consisting of halogen, C$_{1-6}$ alkyl, OC$_{1-6}$ alkyl and CN;
each $R_{10}$ and $R_{11}$ is independently selected from the group consisting of hydrogen and C$_{1-6}$ alkyl that is optionally substituted with up to three substituents selected from the group consisting of OH, CF$_3$, SH and halogen;
each $R_{12}$ is independently selected from the group consisting of hydrogen, C$_{1-6}$ alkyl, C$_{1-6}$ perhaloalkyl, OC$_{1-6}$ alkyl, OC$_{1-6}$ perhaloalkyl, thioalkyl, OH, (CH$_2$)$_l$OSO$_3$H, (CH$_2$)$_l$SO$_3$H, (CH$_2$)$_l$CO$_2$R$_6$, (CH$_2$)$_l$SO$_2$NR$_8$R$_9$, (CH$_2$)$_l$C(=O)NR$_8$R$_9$, NR$_8$R$_9$, alkenyl, alkynyl, or NHCOR$_8$, wherein any of said alkyl, Oalkyl, alkenyl or alkynyl can optionally be substituted with up to three substituents selected from the group consisting of halogen, C$_{1-6}$ alkyl, OC$_{1-6}$ alkyl and CN;
each $R_{13}$ is selected from hydrogen, C(=O)R$_{14}$, SO$_2$R$_{14}$, C$_{1-6}$ alkyl, C$_{1-6}$ haloalkyl, thioalkyl, OH, (CH$_2$)$_l$OSO$_3$H, (CH$_2$)$_l$SO$_3$R$_{10}$, (CH$_2$)$_n$CO$_2$R$_{10}$, SO$_3$R$_{10}$, PO$_3$R$_{10}$R$_{11}$, (CH$_2$)$_n$SO$_2$(CH$_2$)$_n$NR$_{10}$R$_{11}$, (CH$_2$)$_n$CONR$_{10}$R$_{11}$, COR$_{10}$, aryl, heterocyclo, C(=O)aryl, C(=O)heterocyclo, OC(=O)aryl, C(=O)heterocyclo, Oaryl, Oheterocyclo, arylalkyl, C(=O)arylalkyl, OC(=O)arylalkyl, Oarylalkyl, alkenyl, and alkynyl, wherein any of said alkyl, aryl, heterocyclo, C(=O)aryl, C(=O)heterocyclo, OC(=O)aryl, OC(=O)heterocyclo, (Daryl, Oheterocyclo, arylalkyl, C(=O)arylalkyl, OC(=O)arylalkyl, Oarylalkyl, alkenyl or alkynyl can optionally be substituted with up to three substituents selected from the group consisting of halogen, $C_{1-6}$ alkyl, $OC_{1-6}$ alkyl and CN;

$R_{14}$ is independently selected from the group consisting of $C_{1-10}$ alkyl, $OC_{1-10}$ alkyl and $NR_6R_7$ each n is an independently selected integer from 0 to 6;

each l is an independently selected integer from 1 to 6; and

Z is aryl, arylalkyl, heteroaryl or heterocyclo, wherein each of said aryl, arylalkyl, heteroaryl and heterocyclo is optionally substituted.

3. The compound of claim 2 wherein k is 0, bond a is a single bond, and $Q_1$ is $NR_{13}$.

4. The compound of claim 2 wherein k is 0, bond a is a single bond, and $Q_1$ is NH.

5. The compound of claim 2 wherein $Q_1$, $Q_2$ and $Q_3$ are $CH_2$; k is 1, and Q is $NR_{13}$.

6. The compound of claim 2 wherein the compound is selected from the group consisting of:
- d) 2-(4-chloro-benzyl)-3-hydroxy-7,8,9,10-tetrahydro-[1,9]phenanthroline-4-carboxylic acid;
- e) 2-(4-chloro-benzyl)-3-hydroxy-9-isopropyl-7,8,9,10-tetrahydro-[1,9]phenanthroline-4-carboxylic acid;
- f) 9-benzyl-2-(4-chloro-benzyl)-3-hydroxy-7,8,9,10-tetrahydro-[1,9]phenanthroline-4-carboxylic acid;
- g) 2-(4-chloro-benzyl)-9-ethyl-3-hydroxy-7,8,9,10-tetrahydro-[1,9]phenanthroline-4-carboxylic acid;
- h) 9-acetyl-2-(4-chloro-benzyl-hydroxy-7,8,9,10-tetrahydro-[1,9]phenanthroline-4-carboxylic acid;
- i) 9-carbamoyl-2-(4-chloro-benzyl)-3-hydroxy-7,8,9,10-tetrahydro-[1,9]phenanthroline-4-carboxylic acid;
- j) 9-benzoyl-2-(4-chloro-benzyl)-3-hydroxy-7,8,9,10-tetrahydro-[1,9]phenanthroline-4-carboxylic acid;
- k) 9-benzoyl-3-benzoyloxy-2-(4-chloro-benzyl)-7,8,9,10-tetrahydro-[1,9]phenanthroline-4-carboxylic acid;
- l) 2-(4-chloro-benzyl)-3-hydroxy-9-methanesulfonyl-7,8,9,10-tetrahydro-[1,9]phenanthroline-4-carboxylic acid;
- m) 2-(4-chloro-benzyl)-3-hydroxy-7,10-dihydro-8H-[1,9]phenanthroline-4,9-dicarboxylic acid 9-ethyl ester;
- n) 2-(4-chloro-benzyl)-3-ethoxycarbonyloxy-7,10-dihydro-8H-[1,9]phenanthroline-4,9-dicarboxylic acid 9-ethyl ester;
- o) 2-(4-chloro-benzyl)-3-hydroxy-9-phenylacetyl-7,8,9,10-tetrahydro-[1,9]-phenanthroline-4-carboxylic acid; and
- p) 2-(4-chloro-benzyl)-3-hydroxy-9-(propane-2-sulfonyl)-7,8,9,10-tetrahydro-[1,9]phenanthroline-4-carboxylic acid; or pharmaceutically acceptable salts thereof.

* * * * *